United States Patent [19]
Donovan et al.

[11] Patent Number: 5,616,319
[45] Date of Patent: Apr. 1, 1997

[54] BACILLUS THURINGIENSIS CRYET5 GENE AND RELATED PLASMIDS, BACTERIA AND INSECTICIDES

[75] Inventors: William P. Donovan, Levittown; Yuping Tan, Falls Township; Christine S. Jany, Doylestown, all of Pa.; José M. González, Jr., Ewing Township, N.J.

[73] Assignee: Monsanto Company, St. Louis, Mo.

[21] Appl. No.: 176,865

[22] Filed: Dec. 30, 1993

Related U.S. Application Data

[62] Division of Ser. No. 100,709, Jul. 29, 1993, Pat. No. 5,322,687.
[51] Int. Cl.$^6$ .......................... A01N 63/00; C12N 15/32; C12N 1/21; C12N 15/63
[52] U.S. Cl. .................. 424/93.2; 435/69.1; 435/71.3; 435/112.3; 435/252.3; 435/252.31; 435/320.1; 536/23.71; 536/23.1; 536/24.32; 424/93.461; 935/11; 935/29; 935/74
[58] Field of Search .......................... 435/69.1, 71.3, 435/172.3, 252.3, 252.31, 320.1; 536/23.71, 23.1, 24.32; 424/93.2, 93.461; 935/11, 29, 74

[56] References Cited

U.S. PATENT DOCUMENTS

| | | | |
|---|---|---|---|
| 5,087,897 | 1/1992 | Gonzalez, Jr. | 424/93 |
| 5,204,237 | 4/1993 | Gaertner et al. | 435/6 |

FOREIGN PATENT DOCUMENTS

| | | |
|---|---|---|
| 289479 | 11/1988 | European Pat. Off. . |
| 295156 | 12/1988 | European Pat. Off. . |
| 358557 | 3/1990 | European Pat. Off. . |
| 367474 | 5/1990 | European Pat. Off. . |
| 401979 | 12/1990 | European Pat. Off. . |
| 405810 | 1/1991 | European Pat. Off. . |
| 462721 | 12/1991 | European Pat. Off. . |
| 90/13651 | 11/1990 | WIPO . |
| 91/16434 | 10/1991 | WIPO . |

OTHER PUBLICATIONS

Gleave et al, *J. Gen. Microbiol.* 138: 55–62 (1992) "Identification of an insecticidal crystal protein from *Bacillus thuringiensis* DSIR517 with significant sequence differences from previously described toxins".

Turner et al., *Appl. Environ. Microbiology.* 57: 3522–3528 (1991) "Stability of the δ–Endotoxin Gene from *Bacillus thuringiensis* subsp. kurstaki in a Recombinant Strain of *Clavibacter xyli* subsp. cynodontis".

Smulevitch et al., *FEBS Lett* 293:25–28 (1991) "Nucleotide sequence of a novel δ–endotoxin gene cryIg of *Bacillus thuringiensis* ssp. galleriae".

Chambers et al., *J. Bacteriol.* 173: 3966–3976 (1991) "Isolation and Characterization of a Novel Insecticidal Crystal Protein Gene from *Bacillus thuringiensis* subsp. aizawai".

Perlak et al., *Proc. Natl. Acad. Sci. USA* 88: 3324–3328 (1991) "Modification of the coding sequence enhances plant expression of insect control protein genes".

Macaluso et al., *J. Bacteriol.* 173: 1353–1356 (1991) "Efficient Transformation of *Bacillus thuringiensis* Requires Nonmethylated Plasmid DNA".

Von Tersch et al., *Appl. Environ. Microbiology* 57: 349–358 (1991) "Insecticidal Toxins from *Bacillus thuringiensis* subsp. kenvae: Gene Cloning and Characterization and Comparison with *B. thuringiensis* subsp. kurstaki CryIA(c) Toxins".

Visser et al., *J. Bacteriol.* 172: 6738–6788 (1990) "A Novel *Bacillus thuringiensis* Gene Encoding a *Spodoptera exigua*–Specific Crystal Protein".

Mettus et al., *Appl. Environ. Microbiology.* 56: 1128–1134 (1990) "Expression of *Bacillus thuringiensis* δ–Endotoxin Genes during Vegetative Growth".

Hodgman et al., *J. DNA Sequencing and Mapping* 1: 97–106 (1990) "Models for the structure and function of the *Bacillus thuringiensis* δ–endotoxins determined by compilational analysis".

Höfte et al., *Microbiol. Rev.* 53: 242–255 (1989) "Insecticidal Crystal Proteins of *Bacillus thuringiensis*".

Sanchis et al., *Molecular Microbiol.* 3: 229–238 (1989) "Nucleotide sequence and analysis of the N–terminal coding region of the Spodoptera–active δ–endotoxin gene of *Bacillus thuringiensis* aizawai 7.29".

Masson, et al., *Nucl. Acids Res.* 17: 446 (1989) "Nucleotide sequence of a gene cloned from *Bacillus thuringiensis* subspecies entomocidus coding for an insecticidal protein toxic for *Bombyx mori*".

Haider et al., *Nucl. Acids Res* 16: 10927 (1988) "Nucleotide sequence of a *Bacillus thuringiensis* aizawa IC1 entomocidal crystal protein gene".

Honée et al., *Nucl. Acids Res.* 16: 6240 (1988) "Nucleotide sequence of crystal protein gene isolated from *B. thuringiensis* subspecies entomocidus 60.5 coding for a toxin highly active against Spodoptera species".

Brizzard et al., *Nucl. Acids Res.* 16:2723–2724 (1988) "Nucleotide sequence of an additional crystal protein gene cloned from *Bacillus thuringiensis*".

(List continued on next page.)

Primary Examiner—Robert A. Wax
Assistant Examiner—Rebecca Prouty
Attorney, Agent, or Firm—Panitch Schwarze Jacobs & Nadel, P.C.

[57] ABSTRACT

A *Bacillus thuringiensis* strain isolate, designated B.t. strain EG5847, exhibits insecticidal activity against lepidopteran insects. Two novel toxin genes from *B.t.* strain EG5847 designated cryET4 and cryET5 produce insecticidal proteins with activity against a broad spectrum of insects of the order Lepidoptera. The cryET4 gene has a nucleotide base sequence shown in FIG. 1 and listed in SEQ ID NO:1 and produces a CryET4 gene product having the deduced amino acid sequence shown in FIG. 1 and listed in SEQ ID NO:2. The cryET5 gene has a nucleotide base sequence shown in FIG. 2 and listed in SEQ ID NO:3 and produces a CryET5 gene product having the deduced amino acid sequence shown in FIG. 2 and listed in SEQ ID NO:4.

7 Claims, 25 Drawing Sheets

OTHER PUBLICATIONS

Shimizu et al., *Agric. Biol. Chem.* 52: 1565–1573 (1988) "Cloning and Expression in *Escherichia coli* of the 135–kDa Insecticidal Protein Gene from *Bacillus thuringiensis* subsp. aizawai IPL7".

Visser et al., Mol. *Mol. Gen. Genet.* 212: 219–224 (1988) "Genes from *Bacillus thuringiensis* entomocidus 60.5 coding for insect–specific crystal proteins".

Fischoff et al., *Bio/Technology* 5: 807–813 (1987) "Insect Tolerant Transgenic Tomato Plants".

Oeda et al., *Gene* 53: 113–119 (1987) "Nucleotide sequence of the insecticidal protein gene of *Bacillus thuringiensis* strain aizawai IPL7 and its high–level expression in *Escherichia coli*".

Hefford et al., *J. Biotechnology* 6: 307–322 (1987) "Sequence of a lepidopteran toxin gene of *Bacillus thuringiensis* subsp kurstaki NRD–12".

Kondo et al., *Agric. Biol. Chem.* 51: 455–463 (1987) "Cloning and Nucleotide Sequencing of Two Insecticidal δ–Endotoxin Genes from *Bacillus thuringiensis* var. kurstaki HD–1 DNA".

Geiser et al., *Gene* 48: 109–118 (1986) "The hypervariable region of the genes coding for entomopathogenic crystal proteins of *Bacillus thuringiensis*: nucleotide sequence of the kurhd1 gene of subsp. kurstaki HD1".

Obukowicz et al., "Integration of the delta–endotoxin gene of *Bacillus thuringiensis* into the chromosome of root–colonizing strains of pseudomonads using Tn5", *Gene* 45: 327–331 (1986).

Wabiko et al., *DNA* 5:305–314 (1986) "*Bacillus thuringiensis* Entomocidal Protoxin Gene Sequence and Gene Product Analysis".

Höfte et al., *Eur. J. Biochem.* 161:273–280 (1986) "Structural and functional analysis of a cloned delta endotoxin of *Bacillus thuringiensis* berliner 1715".

Schnepf et al., *J. Biol. Chem.* 260:6264–6272 (1985) "The Amino Acid Sequence of a Crystal Protein From *Bacillus thuringiensis* Deduced from the DNA Base Sequence*".

Adang et al., *Gene* 36:289–300 (1985) "Characterized full-–length and truncated plasmid clones of the crystal protein of *Bacillus thuringiensis* subsp kurstaki HD–73 and their toxicity to *Manduca sexta*".

Shibano et al., *Gene* 34:243–251 (1985) "Nucleotide sequence coding for the insecticidal fragment of the *Bacillus thuringiensis* crystal protein".

Carlton et al., "Plasmids and Delta–Endotoxin Production in Different Subspecies of *Bacillus thuringiensis*", pp. 246–252, in *Molecular Biology of Microbial Differentiation*, J. A. Hoch and P. Setlow, ed., American Society for Microbiology, Washington, D.C. (1985).

King et al., "*Heliothis Virescens*", in *Handbook of Insect Rearing*, vol. II, P. Singh and R.F. Moore (eds.), pp. 323–328, Elsevier Science, Amsterdam, (1985).

Kaiser et al., *Science* 223: 249–255 (1984) "Amphiphilic Secondary Structure: Design of Peptide Hormones".

Gonzalez, Jr. et al., "Transfer of *Bacillus thuringiensis* plasmids coding for δ–endotoxin among strains of *B. thuringiensis* and *B. cereus*", *Proc. Natl. Acad. Sci. USA*, 79: 6951–6955 (1982).

FIGURE 1A

```
AAATTCATAA TATGAATCAT ACGTTTAAA GTGTTGTGAA GAAAAGAGAA TTGATCTTTA              60

GAATTTTTT ATTTAACCA AAGAGAAAGG GTAACTT ATG GAG ATA AAT AAT                   113
                                      Met Glu Ile Asn Asn
                                       1               5

CAG AAG CAA TGC ATA CCA TAT AAT TGC TTA AGT AAT CCT GAG GAA GTA              161
Gln Lys Gln Cys Ile Pro Tyr Asn Cys Leu Ser Asn Pro Glu Glu Val
             10                  15                  20

CTT TTG GAT GGG GAG AGG ATA TTA CCT GAT ATC GAT CCA CTC GAA GTT              209
Leu Leu Asp Gly Glu Arg Ile Leu Pro Asp Ile Asp Pro Leu Glu Val
         25                  30                  35

TCT TTG TCG CTT TTG CAA TTT CTT TTG AAT AAC TTT GTT CCA GGG GGA              257
Ser Leu Ser Leu Leu Gln Phe Leu Leu Asn Asn Phe Val Pro Gly Gly
     40                  45                  50

GGC TTT ATT TCA GGA TTA GTT GAT AAA ATA TGG GGG GCT TTG AGA CCA              305
Gly Phe Ile Ser Gly Leu Val Asp Lys Ile Trp Gly Ala Leu Arg Pro
 55                  60                  65

TCT GAA TGG GAC TTA TTT CTT GCA CAG ATT GAA CGG TTG ATT GAT CAA              353
Ser Glu Trp Asp Leu Phe Leu Ala Gln Ile Glu Arg Leu Ile Asp Gln
             70                  75                  80             85

AGA ATA GAA GCA ACA GTA AGA GCA AAA GCA ATC ACT GAA TTA GAA GGA              401
Arg Ile Glu Ala Thr Val Arg Ala Lys Ala Ile Thr Glu Leu Glu Gly
             90                  95                 100

TTA GGG AGA AAT TAT CAA ATA TAC GCT GAA GCA TTT AAA GAA TGG GAA              449
Leu Gly Arg Asn Tyr Gln Ile Tyr Ala Glu Ala Phe Lys Glu Trp Glu
            105                 110                 115
```

FIGURE 1B

```
TCA GAT CCT GAT AAC GAA GCG GCT AAA AGT AGA GTA ATT GAT CGC TTT    497
Ser Asp Pro Asp Asn Glu Ala Ala Lys Ser Arg Val Ile Asp Arg Phe
120                     125                 130

CGT ATA CTT GAT GGT CTA ATT GAA GCA AAT ATC CCT TCA TTT CGG ATA    545
Arg Ile Leu Asp Gly Leu Ile Glu Ala Asn Ile Pro Ser Phe Arg Ile
    135                 140                 145

ATT GGA TTT GAA GTG CCA CTT TTA TCG GTT TAT GTT CAA GCA GCT AAT    593
Ile Gly Phe Glu Val Pro Leu Leu Ser Val Tyr Val Gln Ala Ala Asn
150                 155                 160                 165

CTA CAT CTC GCT CTA TTG AGA GAT TCT GTT ATT TTT GGA GAG AGA TGG    641
Leu His Leu Ala Leu Leu Arg Asp Ser Val Ile Phe Gly Glu Arg Trp
        170                 175                     180

GGA TTG ACG ACA AAA AAT GTC AAT GAT ATC TAT AAT AGA CAA ATT AGA    689
Gly Leu Thr Thr Lys Asn Val Asn Asp Ile Tyr Asn Arg Gln Ile Arg
            185                 190                 195

GAA ATT CAT GAA TAT AGC AAT CAT TGC GTA GAT ACG TAT AAC ACA GAA    737
Glu Ile His Glu Tyr Ser Asn His Cys Val Asp Thr Tyr Asn Thr Glu
        200                 205                 210

CTA GAA CGT CTA GGG TTT AGA TCT ATA GCG CAG TGG AGA ATA TAT AAT    785
Leu Glu Arg Leu Gly Phe Arg Ser Ile Ala Gln Trp Arg Ile Tyr Asn
215                 220                 225

CAG TTT AGA AGA GAA CTA ACA CTA ACT GTA TTA GAT ATT GTC GCT CTT    833
Gln Phe Arg Arg Glu Leu Thr Leu Thr Val Leu Asp Ile Val Ala Leu
230                 235                 240                 245
```

FIGURE 1C

```
TTC CCG AAC TAT GAC AGT AGA CTG TAT CCG ATC CAA ACT TTT TCT CAA    881
Phe Pro Asn Tyr Asp Ser Arg Leu Tyr Pro Ile Gln Thr Phe Ser Gln
                250                 255                 260

TTG ACA AGA GAA ATT GTT ACA TCC CCA GTA AGC GAA TTT TAT TAT GGT    929
Leu Thr Arg Glu Ile Val Thr Ser Pro Val Ser Glu Phe Tyr Tyr Gly
            265                 270                 275

GTT ATT AAT AGT GGT AAT ATA ATT ATT GGT ACT CTT ACT GAA CAG CAG ATA    977
Val Ile Asn Ser Gly Asn Ile Ile Ile Gly Thr Leu Thr Glu Gln Gln Ile
            280                     285                 290

AGG CGA CCA CAT CTT ATG GAC TTC TTT AAC TCC ATG ATC ATG TAT ACA   1025
Arg Arg Pro His Leu Met Asp Phe Phe Asn Ser Met Ile Met Tyr Thr
        295                 300                 305

TCA GAT AAT AGA CGG GAA CAT TAT TGG TCA GGA GCT CTT GAA ATG ACG GCT   1073
Ser Asp Asn Arg Arg Glu His Tyr Trp Ser Gly Ala Leu Glu Met Thr Ala
        310                 315                 320                 325

TAT TTT ACA GGA TTT GCA GGA GCT CAA GTG TCA TTC CCT TTA GTC GGG   1121
Tyr Phe Thr Gly Phe Ala Gly Ala Gln Val Ser Phe Pro Leu Val Gly
            330                 335                 340

ACT AGA GGG GAG TCA GCT CCA CCA TTA ACT GTT AGA AGT GTT AAT GAT   1169
Thr Arg Gly Glu Ser Ala Pro Pro Leu Thr Val Arg Ser Val Asn Asp
        345                 350                 355

GGA ATT TAT AGA ATA TTA TCG GCA CCG TTT TAT TCA GCG CCT TTT CTA   1217
Gly Ile Tyr Arg Ile Leu Ser Ala Pro Phe Tyr Ser Ala Pro Phe Leu
        360                 365                 370
```

FIGURE 1D

```
GGC ACC ATT GTA TTG GGA AGT CGT GGA GAA AAA TTT GAT TTT GCG CTT    1265
Gly Thr Ile Val Leu Gly Ser Arg Gly Glu Lys Phe Asp Phe Ala Leu
            375                 380                 385

AAT AAT ATT TCA CCT CCG CCA TCT ACA ATA TAC AGA CAT CCT GGA ACA    1313
Asn Asn Ile Ser Pro Pro Pro Ser Thr Ile Tyr Arg His Pro Gly Thr
        390                 395                 400             405

GTA GAT TCA CTA GTC AGT ATA CCG CCA CAG GAT AAT AGC GTA CCA CCG    1361
Val Asp Ser Leu Val Ser Ile Pro Pro Gln Asp Asn Ser Val Pro Pro
            410                 415                         420

CAC AGG GGA TCT AGT CAT CGA TTA AGT CAT GTT ACA ATG CGC GCA AGT    1409
His Arg Gly Ser Ser His Arg Leu Ser His Val Thr Met Arg Ala Ser
        425                 430                 435

TCC CCT ATA TTC CAT TGG ACG CAT CGC AGC GCA ACC ACT AAT ACA        1457
Ser Pro Ile Phe His Trp Thr His Arg Ser Ala Thr Thr Thr Asn Thr
        440                 445                 450

ATT AAT CCA AAT GCT ATT ATC CAA ATA CCA CTA GTA AAA GCA TTT AAC    1505
Ile Asn Pro Asn Ala Ile Ile Gln Ile Pro Leu Val Lys Ala Phe Asn
    455                 460                 465

CTT CAT TCA GGT GCC ACT GTT AGA GGA CCA GGG TTT ACA GGT GGT        1553
Leu His Ser Gly Ala Thr Val Arg Gly Pro Gly Phe Thr Gly Gly
        470                 475                 480             485

GAT ATC CTT CGA AGA ACG AAT ACT GGC ACA TTT GCA GAT ATG AGA GTA    1601
Asp Ile Leu Arg Arg Thr Asn Thr Gly Thr Phe Ala Asp Met Arg Val
        490                 495                         500
```

FIGURE 1E

```
AAT ATT ACT GGG CCA TTA TCC CAA AGA TAT CGT GTA AGA ATT CGC TAT    1649
Asn Ile Thr Gly Pro Leu Ser Gln Arg Tyr Arg Val Arg Ile Arg Tyr
            505                     510                 515

GCT TCT ACG ACA GAT TTA CAA TTT TTC ACG AGA ATC AAT GGA ACT TCT    1697
Ala Ser Thr Thr Asp Leu Gln Phe Phe Thr Arg Ile Asn Gly Thr Ser
            520                     525                 530

GTA AAT CAA GGT AAT TTC CAA AGA ACT ATG AAT AGA GGG GAT AAT TTA    1745
Val Asn Gln Gly Asn Phe Gln Arg Thr Met Asn Arg Gly Asp Asn Leu
            535                     540                 545

GAA TCT GGA AAC TTT AGG ACT GCA GGA TTT AGT ACG CCT TTT AGT TTT    1793
Glu Ser Gly Asn Phe Arg Thr Ala Gly Phe Ser Thr Pro Phe Ser Phe
            550                     555             560     565

TCA AAT GCG CAA AGT ACA TTC ACA TTG GGT ACT CAG GCT TTT TCA AAT    1841
Ser Asn Ala Gln Ser Thr Phe Thr Leu Gly Thr Gln Ala Phe Ser Asn
            570                     575                 580

CAG GAA GTT TAT ATA GAT CGA ATT GAA TTT GTC CCG GCA GAA GTA ACA    1889
Gln Glu Val Tyr Ile Asp Arg Ile Glu Phe Val Pro Ala Glu Val Thr
            585                     590                 595

TTC GAG GCA GAA TCT GAT TTA GAA GAA AGA GCG CAA AAG GCG GTG AAT GCC    1937
Phe Glu Ala Glu Ser Asp Leu Glu Glu Arg Ala Gln Lys Ala Val Asn Ala
            600                     605                 610

CTG TTT ACT TCT ACA AAC CAA CTA GGG CTA AAA ACA GAT GTG ACG GAT    1985
Leu Phe Thr Ser Thr Asn Gln Leu Gly Leu Lys Thr Asp Val Thr Asp
            615                     620                 625
```

FIGURE 1F

```
TAT CAG ATT GAT CAA GTG TCC AAT TTA GTA GAA TGT TTA TCA GAT GAA      2033
Tyr Gln Ile Asp Gln Val Ser Asn Leu Val Glu Cys Leu Ser Asp Glu
630                 635                 640                 645

TTT TGT CTG GAT GAA AAG AGA GAA TTG TCC GAG AAA GTC AAA CAT GCA      2081
Phe Cys Leu Asp Glu Lys Arg Glu Leu Ser Glu Lys Val Lys His Ala
            650                 655                 660

AAG CGA CTT AGT GAT AAG CGG AAC CTA CTT CAA GAT CCA AAC TTC ACA      2129
Lys Arg Leu Ser Asp Lys Arg Asn Leu Leu Gln Asp Pro Asn Phe Thr
        665                 670                 675

TCT ATC AAT AGA CAA CTA GAC CGT GGA TGG AGA GGA AGT ACG GAT ATT      2177
Ser Ile Asn Arg Gln Leu Asp Arg Gly Trp Arg Gly Ser Thr Asp Ile
    680                 685                 690                 725

ACC ATC CAA GGA AAT GAC GTA TTC AAA GAG AAT TAC GTC ACA CTA          2225
Thr Ile Gln Gly Asn Asp Val Phe Lys Glu Asn Tyr Val Thr Leu
695                 700                 705

CCA GGT ACC TTT GAT GAG GAG TGT TAT CCA ACG TAT TTG TAT CAA AAA ATA  2273
Pro Gly Thr Phe Asp Glu Glu Cys Tyr Pro Thr Tyr Leu Tyr Gln Lys Ile
710                 715                 720                 725

GAT GAG TCA AAA TTA CTT AAA GCC TAT ACT CGC TAT GAA TTA AGA GGG TAT  2321
Asp Glu Ser Lys Leu Leu Lys Ala Tyr Thr Arg Tyr Glu Leu Arg Gly Tyr
        730                 735                 740

ATT GAA GAT AGT CAA GAT TTA GAA GTC TAT TTG ATT CGT TAC AAT GCG      2369
Ile Glu Asp Ser Gln Asp Leu Glu Val Tyr Leu Ile Arg Tyr Asn Ala
745                 750                 755
```

FIGURE 1G

```
AAA CAT GAA ACA GTA AAT GTT CCC GGT ACA GGG TCC TTA TGG CCG CTT      2417
Lys His Glu Thr Val Asn Val Pro Gly Thr Gly Ser Leu Trp Pro Leu
            760             765             770

TCA GTC GAA AGC CCA ATC GGA AGG TGC GGA GAA CCG AAT CGA TGT GTG      2465
Ser Val Glu Ser Pro Ile Gly Arg Cys Gly Glu Pro Asn Arg Cys Val
            775             780             785

CCA CAT ATT GAA TGG AAT CCT GAT TTA GAT TGT TCG TGT AGG GAT GGG      2513
Pro His Ile Glu Trp Asn Pro Asp Leu Asp Cys Ser Cys Arg Asp Gly
            790             795             800             805

GAG AAG TGT GCC CAT CAT TCG CAT TTC TCT CTA GAT ATT GAT GTT          2561
Glu Lys Cys Ala His His Ser His Phe Ser Leu Asp Ile Asp Val
            810             815             820

GGA TGT ACA GAC AAT GAG GAC CTA GGT GTA TGG GTG ATC TTT AAG          2609
Gly Cys Thr Asp Asn Glu Asp Leu Gly Val Trp Val Ile Phe Lys
            825             830             835

ATT AAA ACG CAG GAT GGC CAT GCA AGA TTA GGA AAT CTA GAG TTT CTC      2657
Ile Lys Thr Gln Asp Gly His Ala Arg Leu Gly Asn Leu Glu Phe Leu
            840             845             850

GAA GAG GAA CCA TTG TTA GGA GAA GCG TTA GCT CGT GTG AAA AGA GCG      2705
Glu Glu Glu Pro Leu Leu Gly Glu Ala Leu Ala Arg Val Lys Arg Ala
            855             860             865

GAG AAA TGG AGA GAC CGC GAA CAA TTG CAG TTT GAA ACG AAT              2753
Glu Lys Trp Arg Asp Arg Lys Arg Glu Gln Leu Gln Phe Glu Thr Asn
    870             875             880             885
```

FIGURE 1H

```
ATC GTT TAC AAA GAG GCA AAA GAA TCT GTA GAT GCT TTA TTC GTA GAT    2801
Ile Val Tyr Lys Glu Ala Lys Glu Ser Val Asp Ala Leu Phe Val Asp
            890                 895                 900

TCT CAC TAT AAT AGA TTA CAA GCG GAT ACG AAC ATT ACG ATG ATT CAT    2849
Ser His Tyr Asn Arg Leu Gln Ala Asp Thr Asn Ile Thr Met Ile His
        905                 910                 915

GCG GCA GAT AAA CGC GTT CAT CGA ATC CGA GAG GCT TAT CTT CCG GAA    2897
Ala Ala Asp Lys Arg Val His Arg Ile Arg Glu Ala Tyr Leu Pro Glu
    920                 925                 930

TTA TCC GTT ATC CCA GGT GTA AAT GCG GAC ATT TTT GAA GAA TTA GAA    2945
Leu Ser Val Ile Pro Gly Val Asn Ala Asp Ile Phe Glu Glu Leu Glu
935                 940                 945

GGT CTT ATT TTC ACT GCA TTC TCC CTA TAT GAT CGT TCT GCG AGA AAT ATC ATT    2993
Gly Leu Ile Phe Thr Ala Phe Ser Leu Tyr Asp Arg Ser Ala Arg Asn Ile Ile
950                 955                 960                 965

AAA AAC GGT GAT TTC AAT AAT GGT TTA TCG TGT TGG AAC GTG AAA GGG    3041
Lys Asn Gly Asp Phe Asn Asn Gly Leu Ser Cys Trp Asn Val Lys Gly
        970                 975                 980

CAT GTA GAT ATA CAA CAG AAT CAT CGT TCT GTC CTC GTT CCG    3089
His Val Asp Ile Gln Gln Asn His Arg Ser Val Leu Val Pro
    985                 990                 995

GAA TGG GAA TCA GAG GTA TCA CAA GAA GTC CGC GTA TGT CCA GGT CGT    3137
Glu Trp Glu Ser Glu Val Ser Gln Glu Val Arg Val Cys Pro Gly Arg
1000                1005                1010
```

FIGURE 1I

```
GGC TAT ATT CTT CGT GTC ACA GCG TAC AAA GAG GGC TAC GGA GAA GGA    3185
Gly Tyr Ile Leu Arg Val Thr Ala Tyr Lys Glu Gly Tyr Gly Glu Gly
1015                    1020                    1025

TGC GTA ACG ATC CAT GAG ATC GAA GAC AAT ACA GAC GAA TTG AAG TTT    3233
Cys Val Thr Ile His Glu Ile Glu Asp Asn Thr Asp Glu Leu Lys Phe
1030                    1035                    1040            1045

AGT AAC TGC ATA GAG GAA GTC TAT CCA ACG GAT ACA GGT AAT GAT        3281
Ser Asn Cys Ile Glu Glu Val Tyr Pro Thr Asp Thr Gly Asn Asp
1045             1050                    1055                1060

TAT ACT GCA CAC CAA GGT ACA ACA GGA TGC GCA GAT GCA TGT AAT TCC    3329
Tyr Thr Ala His Gln Gly Thr Thr Gly Cys Ala Asp Ala Cys Asn Ser
1065                    1070                    1075

CGT AAT GTT GGA TAT GAG GAT GGA TAT GAA ATA AAT ACT ACA GCA TCT    3377
Arg Asn Val Gly Tyr Glu Asp Gly Tyr Glu Ile Asn Thr Thr Ala Ser
1080                    1085                    1090

GTT AAT TAC AAA CCG ACT TAT GAA GAA GAA ATG TAT GAC GAT GTA CGA    3425
Val Asn Tyr Lys Pro Thr Tyr Glu Glu Glu Met Tyr Thr Asp Val Arg
1095                    1100                    1105

AGA GAT AAT CAT TGT GAA TAT GAC AGA GGA TAT GGG AAC CAT ACA CCG    3473
Arg Asp Asn His Cys Glu Tyr Asp Arg Gly Tyr Gly Asn His Thr Pro
1110                    1115                    1120            1125

TTA CCA GCT GGT TAT GTA ACA AAA GAA TTA GAG TAC TTC CCT GAA ACA    3521
Leu Pro Ala Gly Tyr Val Thr Lys Glu Leu Glu Tyr Phe Pro Glu Thr
1130                    1135                    1140
```

FIGURE 1J

```
GAT ACA GTA TGG ATA GAG ATT GGA GAA ACG GAA GGA ACA TTC ATC GTA                3569
Asp Thr Val Trp Ile Glu Ile Gly Glu Thr Glu Gly Thr Phe Ile Val
                1145                    1150                   1155

GAT AGT GTG GAA TTA CTC CTC ATG GAG GAA TAAGATTGTA CGAAATCGAC                   3619
Asp Ser Val Glu Leu Leu Leu Met Glu Glu
                1160                    1165

TTTAAATGGC TCATTCTAAA CAAAAAGTAG TCGTCTAATC TCTGTAACAA ATAGAAAAGT              3679

AAATATTTGT AGAAAAAAGA AAAGGACAT TACT                                            3713
```

FIGURE 2A

```
AAACTATTCA ATGGAGAAAA ATTGAATAGT TGTAATGTAA GCACACCGAA AAAAGGAGGA                    60

GTTATA TTG ACT TCA AAT AGG AAA AAT GAG AAT GAA ATT ATA ATT AAT GCT                  108
       Leu Thr Ser Asn Arg Lys Asn Glu Asn Glu Ile Ile Ile Asn Ala
       1               5                       10

TTA TCG ATT CCA ACG GTA TCG AAT CCT TCC ACG CAA ATG AAT CTA TCA                     156
Leu Ser Ile Pro Thr Val Ser Asn Pro Ser Thr Gln Met Asn Leu Ser
15                  20                  25                  30

CCA GAT GCT CGT ATT GAA GAT AGC TTG TGT GTA GCC GAG GTG AAC AAT                     204
Pro Asp Ala Arg Ile Glu Asp Ser Leu Cys Val Ala Glu Val Asn Asn
                35                  40                  45

ATT GAT CCA TTT GTT AGC GCA TCA ACA GTC CAA ACG GGT ATA AAC ATA                     252
Ile Asp Pro Phe Val Ser Ala Ser Thr Val Gln Thr Gly Ile Asn Ile
            50                  55                  60

GCT GGT AGA ATA TTG GGC GTA TTA GGT GTG CCG TTT GCT GGA CAA CTA                     300
Ala Gly Arg Ile Leu Gly Val Leu Gly Val Pro Phe Ala Gly Gln Leu
65                  70                  75

GCT AGT TTT TAT AGT TTT CTT GTT GGG GAA TTA TGG CCT AGT GGC AGA                     348
Ala Ser Phe Tyr Ser Phe Leu Val Gly Glu Leu Trp Pro Ser Gly Arg
        80                  85                  90

GAT CCA TGG GAA ATT TTC CTG GAA CAT GTA GAA CAA CTT ATA AGA CAA                     396
Asp Pro Trp Glu Ile Phe Leu Glu His Val Glu Gln Leu Ile Arg Gln
            95                 100                 105                 110

CAA GTA ACA GAA AAT ACT AGG AAT ACG GCT ATT GCT CGA TTA GAA GGT                     444
Gln Val Thr Glu Asn Thr Arg Asn Thr Ala Ile Ala Arg Leu Glu Gly
            115                 120                 125
```

FIGURE 2B

```
CTA GGA AGA GGC TAT AGA TCT TAC CAG CAG GCT CTT GAA ACT TGG TTA    492
Leu Gly Arg Gly Tyr Arg Ser Tyr Gln Gln Ala Leu Glu Thr Trp Leu
            130                 135                 140

GAT AAC CGA AAT GAT GCA AGA TCA AGA AGC ATT ATT CTT GAG CGC TAT    540
Asp Asn Arg Asn Asp Ala Arg Ser Arg Ser Ile Ile Leu Glu Arg Tyr
            145                 150                 155

GTT GCT TTA GAA CTT GAC ATT ACT ACT GCT ATA CCG CTT TTC AGA ATA    588
Val Ala Leu Glu Leu Asp Ile Thr Thr Ala Ile Pro Leu Phe Arg Ile
            160                 165                 170

CGA AAT GAA GAA GTT CCA TTA ATG GTA TAT GCT CAA GCT GCA AAT        636
Arg Asn Glu Glu Val Pro Leu Met Val Tyr Ala Gln Ala Ala Asn
            175                 180                 185         190

TTA CAC CTA TTA TTG AGA GAC GCA TCC CTT TTT GGT AGT GAA TGG        684
Leu His Leu Leu Leu Arg Asp Ala Ser Leu Phe Gly Ser Glu Trp
            195                 200                 205

GGG ATG GCA TCT TCC GAT GTT AAC CAA TAT TAC CAA GAA CAA ATC AGA    732
Gly Met Ala Ser Ser Asp Val Asn Gln Tyr Tyr Gln Glu Gln Ile Arg
            210                 215                 220

TAT ACA GAG GAA TAT TCT AAC CAT TGC GTA CAA TGG TAT ACA GGG        780
Tyr Thr Glu Glu Tyr Ser Asn His Cys Val Gln Trp Tyr Thr Gly
            225                 230                 235

CTA AAT AAC TTA AGA GGG ACA AAT GCT GAA AGT TGG TTG CGG TAT AAT    828
Leu Asn Asn Leu Arg Gly Thr Asn Ala Glu Ser Trp Leu Arg Tyr Asn
            240                 245                 250
```

FIGURE 2C

```
CAA TTC CGT AGA GAC CTA ACG TTA GGG GTA TTA GAT TTA GTA GCC CTA         876
Gln Phe Arg Arg Asp Leu Thr Leu Gly Val Leu Asp Leu Val Ala Leu
255                 260                 265                 270

TTC CCA AGC TAT GAT ACT CGC ACT TAT CCA ATC AAT ACG AGT GCT CAG         924
Phe Pro Ser Tyr Asp Thr Arg Thr Tyr Pro Ile Asn Thr Ser Ala Gln
            275                 280                 285

TTA ACA AGA GAA ATT TAT ACA GAT CCA ATT GGG AGA ACA AAT GCA CCT         972
Leu Thr Arg Glu Ile Tyr Thr Asp Pro Ile Gly Arg Thr Asn Ala Pro
        290                 295                 300

TCA GGA TTT GCA AGT ACG AAT TGG TTT AAT AAT AAT GCA CCA TCG TTT        1020
Ser Gly Phe Ala Ser Thr Asn Trp Phe Asn Asn Asn Ala Pro Ser Phe
305                 310                 315

TCT GCC ATA GAG GCT GCC ATT TTC AGG CCT CAT CTA CTT GAT TTT            1068
Ser Ala Ile Glu Ala Ala Ile Phe Arg Pro His Pro Leu Leu Asp Phe
320                 325                 330

CCA GAA CAA CTT ACA ATT TAC AGT GCA TCA AGC CGT TGG AGT AGC ACT        1116
Pro Glu Gln Leu Thr Ile Tyr Ser Ala Ser Arg Trp Ser Ser Thr
335                 340                 345                 350

CAA CAT ATG AAT TAT TGG GTG GGA CAT AGG CTT AAC TTC CGC CCA ATA        1164
Gln His Met Asn Tyr Trp Val Gly His Arg Leu Asn Phe Arg Pro Ile
            355                 360                 365

GGA GGG ACA TTA AAT ACC TCA ACA CAA GGA CTT ACT AAT AAT ACT TCA        1212
Gly Gly Thr Leu Thr Asn Thr Ser Thr Gln Gly Leu Thr Asn Asn Thr Ser
        370                 375                 380
```

FIGURE 2D

```
ATT AAT CCT GTA ACA TTA CAG TTT ACG TCT CGA GAC GTT TAT AGA ACA    1260
Ile Asn Pro Val Thr Leu Gln Phe Thr Ser Arg Asp Val Tyr Arg Thr
385                 390                 395

GAA TCA AAT GCA GGG ACA AAT ATA CTA TTT ACT ACT CCT GTG AAT GGA    1308
Glu Ser Asn Ala Gly Thr Asn Ile Leu Phe Thr Thr Pro Val Asn Gly
    400                 405                 410

GTA CCT TGG GCT AGA TTT AAT TTT ATA AAC CCT CAG AAT ATT TAT GAA    1356
Val Pro Trp Ala Arg Phe Asn Phe Ile Asn Pro Gln Asn Ile Tyr Glu
415                 420                 425                 430

AGA GGC GCC ACT ACC TAC AGT CAA CCG TAT CAG GGA GTT GGG ATT CAA    1404
Arg Gly Ala Thr Thr Tyr Ser Gln Pro Tyr Gln Gly Val Gly Ile Gln
        435                 440                 445

TTA TTT GAT TCA GAA ACT TTA CCA GAA TTA CCA GAA ACA GAA ACA CGA CCA    1452
Leu Phe Asp Ser Glu Thr Leu Pro Pro Glu Thr Glu Arg Pro
        450                 455                 460

AAT TAT GAA TCA TAT AGT CAT AGA TTA TCT CAT ATA GGA CTA ATC ATA    1500
Asn Tyr Glu Ser Tyr Ser His Arg Leu Ser His Ile Gly Leu Ile Ile
    465                 470                 475

GGA AAC ACT TTG AGA GCA CCA GTC TAT TCT TGG ACG CAT CGT AGT GCA    1548
Gly Asn Thr Leu Arg Ala Pro Val Tyr Ser Trp Thr His Arg Ser Ala
    480                 485                 490

GAT CGT ACG AAT ACG ATT GGA CCA AAT AGA ATT ACA CAA ATA CCA TTG    1596
Asp Arg Thr Asn Thr Ile Gly Pro Asn Arg Ile Thr Gln Ile Pro Leu
495                 500                 505                 510
```

FIGURE 2E

```
GTA AAA GCA CTG AAT CTT CAT TCA GGT GTT ACT GTT GGA GGG CCA         1644
Val Lys Ala Leu Asn Leu His Ser Gly Val Thr Val Gly Gly Pro
        515                      520                  525

GGA TTT ACA GGT GGG GAT ATC CTT CGT AGA ACA AAT ACG GGT ACA TTT     1692
Gly Phe Thr Gly Gly Asp Ile Leu Arg Arg Thr Asn Thr Gly Thr Phe
        530                      535                  540

GGA GAT ATA CGA TTA AAT ATT AAT GTG CCA TTA TCC CAA AGA TAT CGC     1740
Gly Asp Ile Arg Leu Asn Ile Asn Val Pro Leu Ser Gln Arg Tyr Arg
        545                      550                  555

GTA AGG ATT CGT TAT GCT TCT ACT ACA GAT TTA CAA TTT TTC ACG AGA     1788
Val Arg Ile Arg Tyr Ala Ser Thr Thr Asp Leu Gln Phe Phe Thr Arg
        560                      565                  570

ATT AAT GGA ACC ACT GTT AAT ATT GGT AAT TTC TCA AGA ACT ATG AAT     1836
Ile Asn Gly Thr Thr Val Asn Ile Gly Asn Phe Ser Arg Thr Met Asn
        575                      580                  585                  590

AGG GGG GAT AAT TTA GAA TAT AGA AGT TTT AGA ACT GCA GGA TTT AGT     1884
Arg Gly Asp Asn Leu Glu Tyr Arg Ser Phe Arg Thr Ala Gly Phe Ser
        595                      600                  605

ACT CCT TTT AAT TTT TTA AAT GCC CAA AGC ACA TTC ACA TTG GGT GCT     1932
Thr Pro Phe Asn Phe Leu Asn Ala Gln Ser Thr Phe Thr Leu Gly Ala
        610                      615                  620

CAG AGT TTT TCA AAT CAG GAA GTT TAT ATA GAT AGA GTC GAA TTT GTT     1980
Gln Ser Phe Ser Asn Gln Glu Val Tyr Ile Asp Arg Val Glu Phe Val
        625                      630                  635
```

FIGURE 2F

```
CCA GAG GTA ACA TTT GAG GCA GAA TAT GAT TTA GAA AGA GCA CAA    2028
Pro Glu Val Thr Phe Glu Ala Glu Tyr Asp Leu Glu Arg Ala Gln
640                 645                 650

AAG GCG GTG AAT GCT CTG TTT ACT TCT ACA AAT CCA AGA AGA TTG AAA    2076
Lys Ala Val Asn Ala Leu Phe Thr Ser Thr Asn Pro Arg Arg Leu Lys
    655                 660                 665                 670

ACA GAT GTG ACA GAT CAT ATT GAC CAA GTG TCC AAT ATG GTG GCA    2124
Thr Asp Val Thr Asp His Ile Asp Gln Val Ser Asn Met Val Ala
675                 680                 685

TGT TTA TCA GAT GAA TTT TGC TTG GAT GAG AAG CGA GAA TTA TTT GAG    2172
Cys Leu Ser Asp Glu Phe Cys Leu Asp Glu Lys Arg Glu Leu Phe Glu
    690                 695                 700

AAA GTG AAA TAT GCG AAG CGA CTC AGT GAT GAA AGA AAC TTA CTC CAA    2220
Lys Val Lys Tyr Ala Lys Arg Leu Ser Asp Glu Arg Asn Leu Leu Gln
705                 710                 715

GAT CCA AAC TTC ACA TTC ATC TTC ATC AGT GGG CAA TTA CTT TTC GCA TCC ATC    2268
Asp Pro Asn Phe Thr Phe Ile Ser Gly Gln Leu Ser Phe Ala Ser Ile
    720                 725                 730

GAT GGA CAA TCA AAC TTC CCC TCT ATT AAT GAG CTA TCT GAA CAT GGA    2316
Asp Gly Gln Ser Asn Phe Pro Ser Ile Asn Glu Leu Ser Glu His Gly
735                 740                 745                 750

TGG TGG GGA AGT GCG AAT GTT ACC ATT CAG GAA GGG AAT GAC GTA TTT    2364
Trp Trp Gly Ser Ala Asn Val Thr Ile Gln Glu Gly Asn Asp Val Phe
    755                 760                 765
```

FIGURE 2G

```
AAA GAG AAT TAC GTC ACA CTA CCG GGT ACT TTT AAT GAG TGT TAT CCA    2412
Lys Glu Asn Tyr Val Thr Leu Pro Gly Thr Phe Asn Glu Cys Tyr Pro
770                             775                      780

AAT TAT TTA TAT CAA AAA ATA GGA GAG TCA GAA TTA AAA GCT TAT ACG    2460
Asn Tyr Leu Tyr Gln Lys Ile Gly Glu Ser Glu Leu Lys Ala Tyr Thr
        785                     790                  795

CGC TAT CAA TTA AGA GGG TAT ATT GAA GAT AGT CAA GAT CTA GAG ATT    2508
Arg Tyr Gln Leu Arg Gly Tyr Ile Glu Asp Ser Gln Asp Leu Glu Ile
800                     805                     810

TAT TTA ATT CGT TAC AAT GCA AAG CAT GAA ACA TTG GAT GTT CCA GGT    2556
Tyr Leu Ile Arg Tyr Asn Ala Lys His Glu Thr Leu Asp Val Pro Gly
815                     820                     825            830

ACC GAT TCC CTA TGG CCG CTT TCA GTT GAA AGC CCA ATC GGA AGG TGC    2604
Thr Asp Ser Leu Trp Pro Leu Ser Val Glu Ser Pro Ile Gly Arg Cys
               835                     840                  845

GGA GAA CCA AAT CGA TGC GCA CCA CAT TTT GAA TGG AAT CCT GAT CTA    2652
Gly Glu Pro Asn Arg Cys Ala Pro His Phe Glu Trp Asn Pro Asp Leu
               850                     855                  860

GAT TGT TCC TGC AGA GAT GGA GAA AGA TGT GCG CAT TCC CAT CAT CAT    2700
Asp Cys Ser Cys Arg Asp Gly Glu Arg Cys Ala His Ser His His His
865                     870                     875

TTC ACT TTG GAT ATT GAT GTT GGG TGC ACA GAC TTG CAT GAG AAC CTA    2748
Phe Thr Leu Asp Ile Asp Val Gly Cys Thr Asp Leu His Glu Asn Leu
880                     885                     890
```

FIGURE 2H

```
GGC GTG TGG GTG GTA TTC AAG ATT AAG ACG CAG GAA GGT TAT GCA AGA    2796
Gly Val Trp Val Val Phe Lys Ile Lys Thr Gln Glu Gly Tyr Ala Arg
895                 900                 905                 910

TTA GGA AAT CTG GAA TTT ATC GAA GAG AAA CCA TTA ATT GGA GAA GCA    2844
Leu Gly Asn Leu Glu Phe Ile Glu Glu Lys Pro Leu Ile Gly Glu Ala
            915                 920                 925

CTG TCT CGT GTG AAG AGA GCG GAA AAA TGG AGA GAC AAA CGG GAA        2892
Leu Ser Arg Val Lys Arg Ala Glu Lys Trp Arg Asp Lys Arg Glu
930                 935                 940

AAA CTA CAA TTG GAA ACA AAA CGA TAT ACA GAG GCA AAA GAA GCT        2940
Lys Leu Gln Leu Glu Thr Lys Arg Tyr Thr Glu Ala Lys Glu Ala
945                 950                 955

GTG GAT GCT TTA TTC GTA GAT TCT CAA TAT GAT CAA TTA CAA GCG GAT    2988
Val Asp Ala Leu Phe Val Asp Ser Gln Tyr Asp Gln Leu Gln Ala Asp
960                 965                 970

ACA AAC ATT GGC ATG ATT CAT GCG GCA GAT AAA CTT GTT CAT CGA ATT    3036
Thr Asn Ile Gly Met Ile His Ala Ala Asp Lys Leu Val His Arg Ile
975                 980                 985                 990

CGA GAG GCG TAT CTT TCA GAA TTA CCT GTT ATC CCA GGT GTA AAT GCG    3084
Arg Glu Ala Tyr Leu Ser Glu Leu Pro Val Ile Pro Gly Val Asn Ala
            995                 1000                1005

GAA ATT TTT GAA GAA TTA GAA GGT CAC ATT ATC ACT GCA ATG TCC TTA    3132
Glu Ile Phe Glu Glu Leu Glu Gly His Ile Ile Thr Ala Met Ser Leu
1010                1015                1020
```

FIGURE 21

```
TAC GAT GCG AGA AAT GTC GTT AAA AAT GGT GAT TTT AAT AAT GGA TTA        3180
Tyr Asp Ala Arg Asn Val Val Lys Asn Gly Asp Phe Asn Asn Gly Leu
            1025                    1030                    1035

ACA TGT TGG AAT GTA AAA GGG CAT GTA GAT CAA CAG AGC CAT CAT            3228
Thr Cys Trp Asn Val Lys Gly His Val Asp Val Gln Gln Ser His His
        1040                    1045                    1050

CGT TCT GAC CTT GTT ATC CCA GAA TGG GAA GCA GAA GTG TCA CAA GCA        3276
Arg Ser Asp Leu Val Ile Pro Glu Trp Glu Ala Glu Val Ser Gln Ala
1055                    1060                    1065                    1070

GTT CGC GTC TGT CCG GGG CGT GGC TAT ATC CTT CGT GTC ACA GCG TAC        3324
Val Arg Val Cys Pro Gly Arg Gly Tyr Ile Leu Arg Val Thr Ala Tyr
            1075                    1080                    1085

AAA GAG GGA TAT GGA GAG GGC TGC GTA ACG ATC CAT GAA ATC GAG AAC        3372
Lys Glu Gly Tyr Gly Glu Gly Cys Val Thr Ile His Glu Ile Glu Asn
        1090                    1095                    1100

AAT ACA GAC GAA CTA AAA TTT AAA AAC TGT GAA GAG GAA GTG TAT            3420
Asn Thr Asp Glu Leu Lys Phe Lys Asn Cys Glu Glu Glu Val Tyr
1105                    1110                    1115

CCA ACG GAT ACA GGA ACG TGT AAT GAT TAT ACT GCA CAC CAA GGT ACA        3468
Pro Thr Asp Thr Gly Thr Cys Asn Asp Tyr Thr Ala His Gln Gly Thr
            1120                    1125                    1130

GCA GCA TGT AAT TCC CGT AAT GCT GGA TAT GAG GAT GCA TAT GAA GTT        3516
Ala Ala Cys Asn Ser Arg Asn Ala Gly Tyr Glu Asp Ala Tyr Glu Val
1135                    1140                    1145                    1150
```

FIGURE 2J

```
GAT ACT ACA GCA TCT GTT AAT TAC AAA CCG ACT TAT GAA GAA ACG   3564
Asp Thr Thr Ala Ser Val Asn Tyr Lys Pro Thr Tyr Glu Glu Thr
            1155                     1160                1165

TAT ACA GAT GTA CGA AGA GAT AAT CAT TGT GAA TAT GAC AGA GGG TAT   3612
Tyr Thr Asp Val Arg Arg Asp Asn His Cys Glu Tyr Asp Arg Gly Tyr
            1170                     1175                     1180

GTG AAT TAT CCA CCA GTA CCA GCT GGT TAT GTG ACA AAA GAA TTA GAA   3660
Val Asn Tyr Pro Pro Val Pro Ala Gly Tyr Val Thr Lys Glu Leu Glu
            1185                     1190                     1195

TAC TTC CCA GAA ACA GAT ACA GTA TGG ATT GAG ATT GGA GAA ACG GAA   3708
Tyr Phe Pro Glu Thr Asp Thr Val Trp Ile Glu Ile Gly Glu Thr Glu
            1200                     1205                     1210

GGA AAG TTT ATT GTA GAT AGC GTG GAA CTA CTC CTC ATG GAA GAA TAGGATCATG   3763
Gly Lys Phe Ile Val Asp Ser Val Glu Leu Leu Leu Met Glu Glu
            1215                     1220                     1225

CAAGTATAGC AGTTTAATAA ATATTAATTA AAATAGTAGT CTAACTTCCG TTCCAATTAA   3823

ATAAGTAAAT TACAGTTGTA AAAGAAAAC GGACATCACT CTTCAGAGAG CGATGTCCGT   3883

TTTTTATATG GTGTGTGCTA ATGATAAATG TGCACGAAAT TATATTGTCA A   3934
```

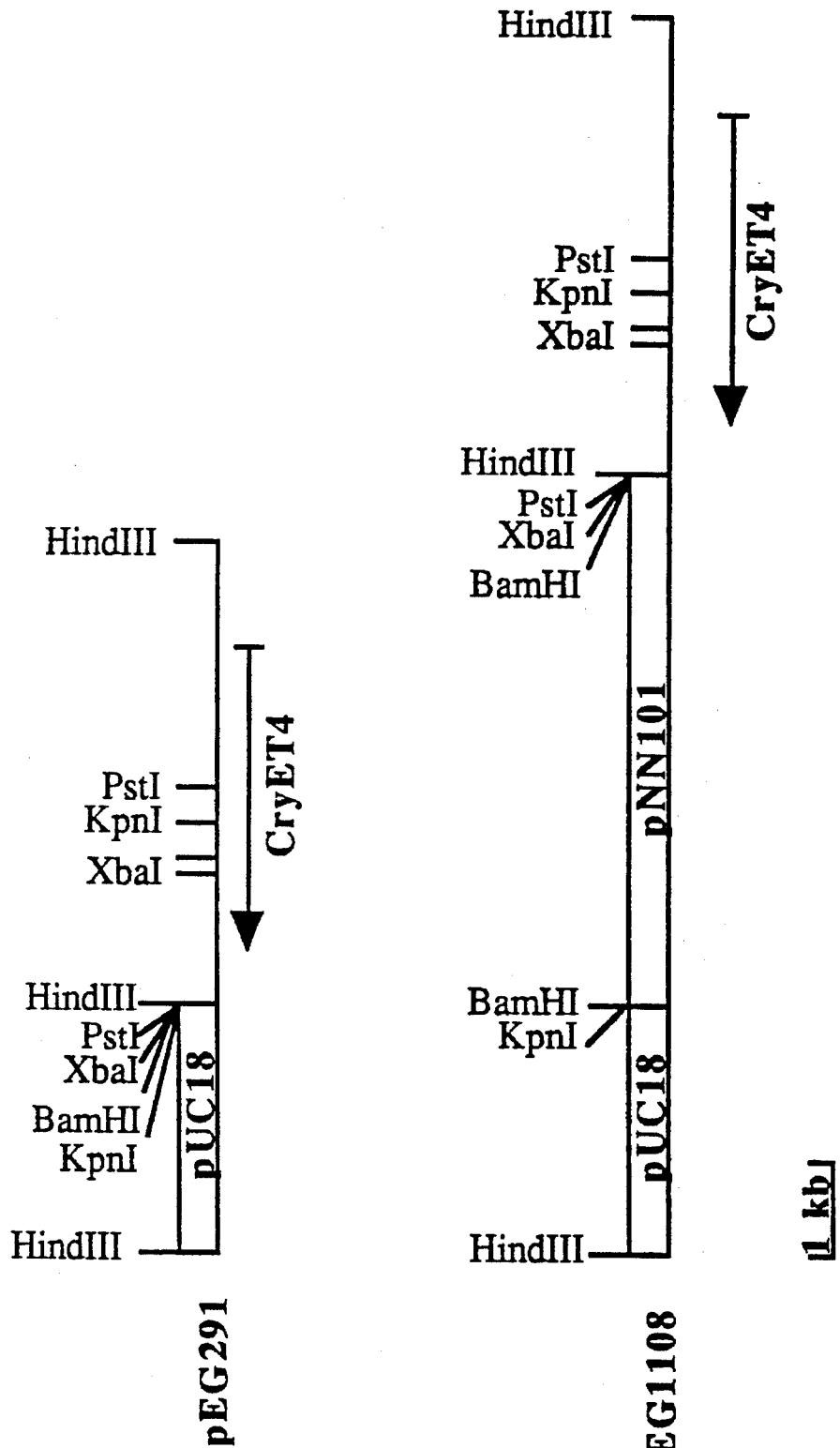
Figure 5A  pEG291
Figure 5B  pEG1108

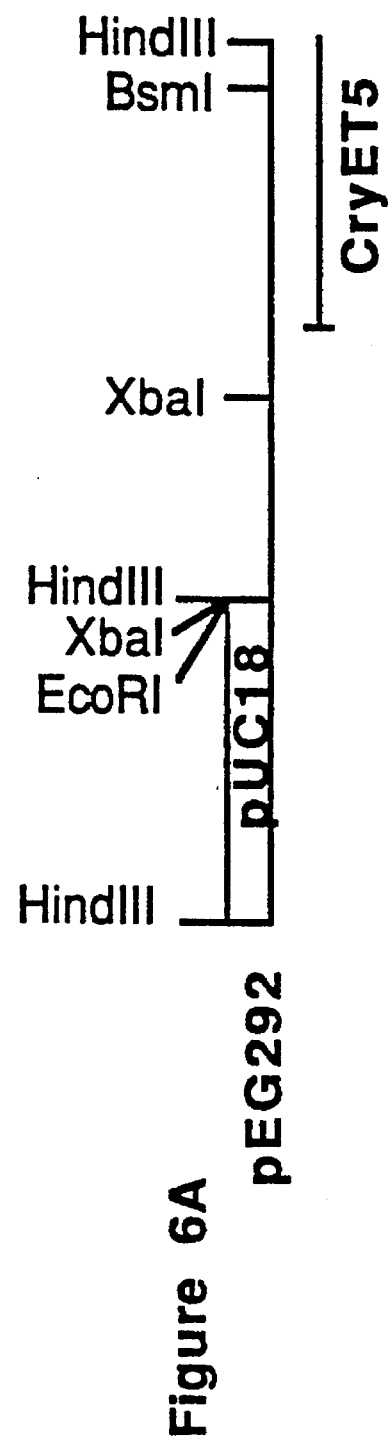
Figure 6A pEG292
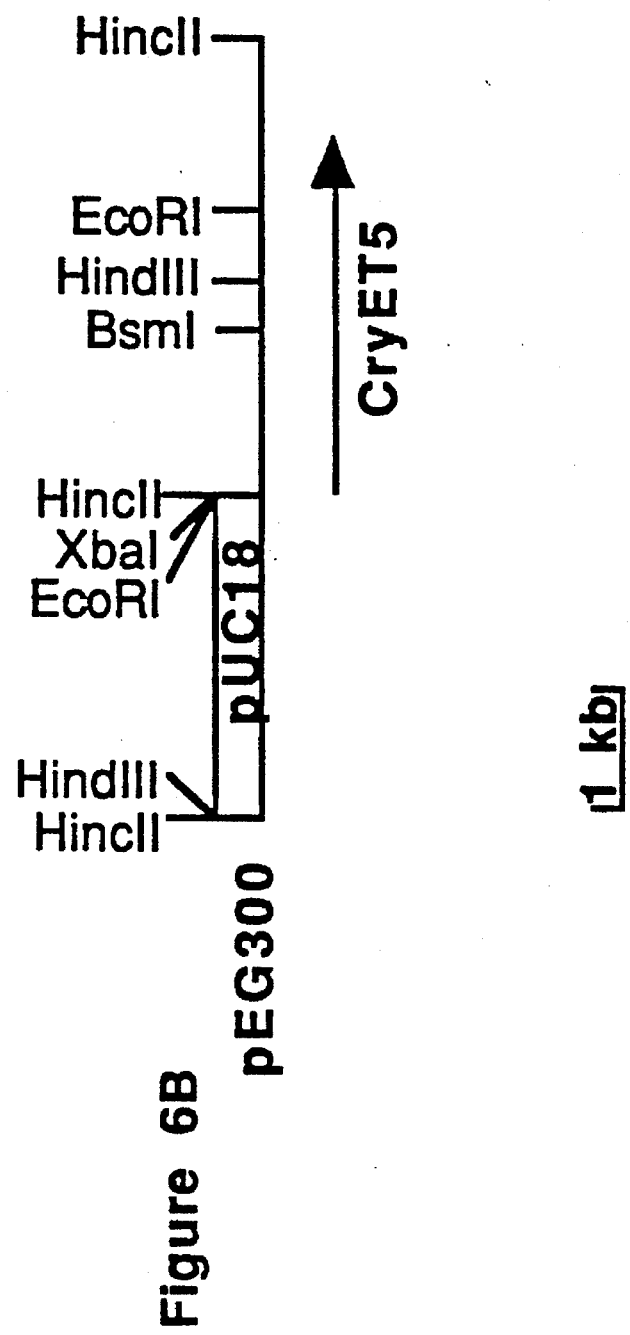
Figure 6B pEG300

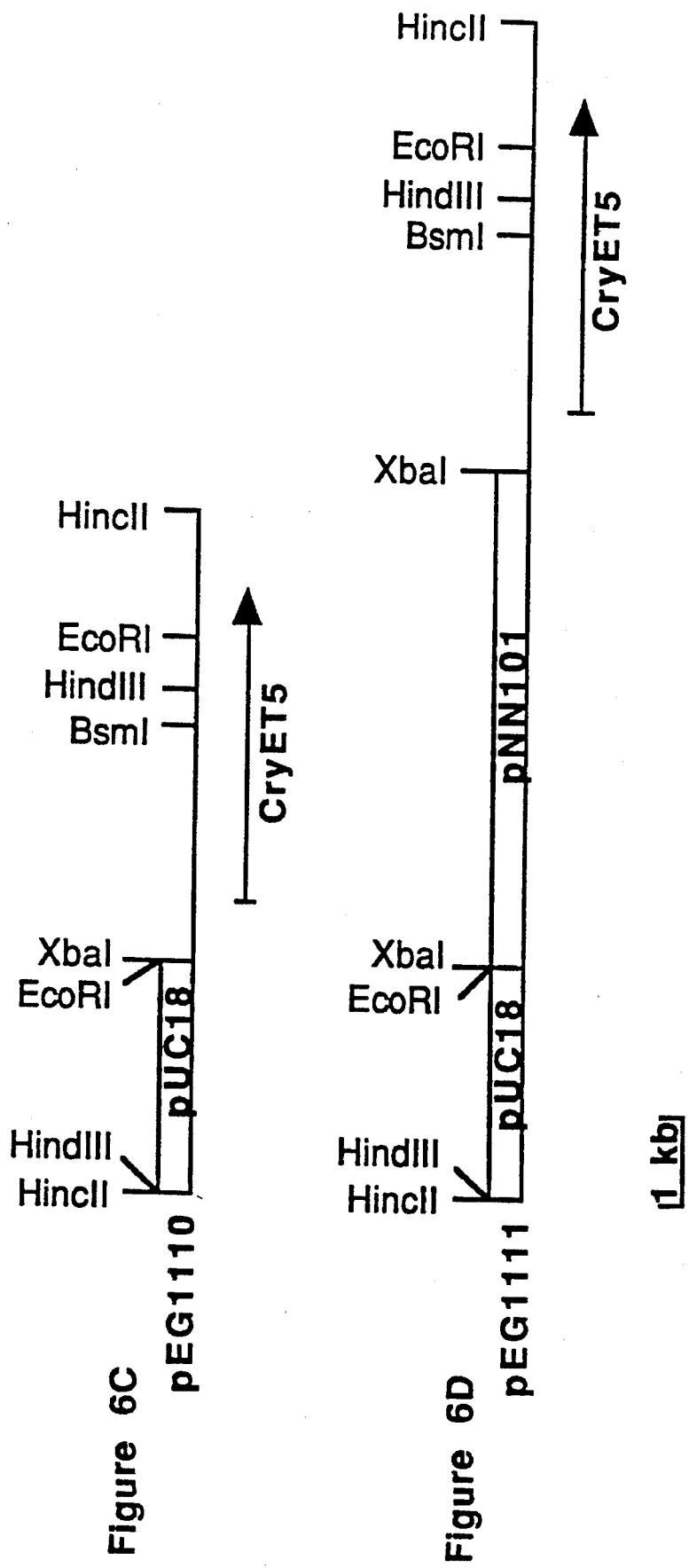

BACILLUS THURINGIENSIS CRYET5 GENE AND RELATED PLASMIDS, BACTERIA AND INSECTICIDES

CROSS-REFERENCE TO A RELATED APPLICATION

This application is a division of U.S. patent application Ser. No. 08/100,709, filed Jul. 29, 1993, now U.S. Pat. No. 5,322,687.

FIELD OF THE INVENTION

The present invention relates to lepidopteran-toxic proteins and the genes coding therefor. In particular, the present invention is directed to genes designated as cryET4 (SEQ ID NO:1) and cryET5 (SEQ ID NO:3) and their proteins designated respectively as CryET4 (SEQ ID NO:2) and CryET5 (SEQ ID NO:4).

BACKGROUND OF THE INVENTION

*Bacillus thuringiensis* (commonly known as *B.t.*) is a gram-positive soil bacterium that often produces cellular inclusions during sporulation which are specifically toxic to certain orders and species of insects. Many different strains of *B.t.* have been shown to produce these inclusions of insecticidal crystal protein (ICP). Compositions including *B.t.* strains which produce insecticidal proteins have been commercially available and used as environmentally acceptable insecticides because they are quite toxic to the specific target insect, but are harmless to plants and other non-targeted organisms.

*B.t.* ICP toxins are active in the insect only after ingestion. After ingestion by an insect, the alkaline pH and proteolytic enzymes in the mid-gut solubilize the crystal allowing the release of the toxic components. These toxic components disrupt the mid-gut cells resulting in cessation of feeding and, eventually, death of the insect. *B.t.* has proven to be an effective and environmentally safe insecticide in dealing with various insect pests.

A number of genes encoding crystal proteins have been cloned from many strains of *B.t.* A good overview is set forth in H. Höfte and H. R. Whiteley, *Microbiol. Rev.*, 53, pp. 242–255 (1989), hereinafter "Höfte and Whiteley (1989)." This reference provides a good overview of the genes and proteins obtained from *B.t.* and their uses, adopts a nomenclature and classification scheme for *B.t.* genes and proteins, and has an extensive bibliography.

The nucleotide sequences of ICP genes responsible for a given crystal phenotype and active against the same insect order are generally more related, i.e., more homologous, than are the nucleotide sequences of *B.t.* genes encoding delta-endotoxin proteins active against different orders of insects. Höfte and Whiteley (1989) defines an ordered classification of genes encoding *B.t.* delta-endotoxin proteins based on homology of delta-endotoxin amino acid sequences, as well as similarities in insecticidal activity; a subranking has also been established based upon further refinement of sequence relationship. As noted by Höfte and Whiteley (1989), the majority of insecticidal *B.t.* strains are active against insects of the order Lepidoptera, i.e., caterpillar insects. Insecticidal crystal proteins specifically active against Lepidoptera have been designated CryI proteins. These ICPs are encoded by cryI genes. Other *B.t.* strains produce different classes of crystal proteins, e.g., CryII proteins are active against lepidopteran and (for CryIIA) dipteran insects; CryIII proteins are insecticidal to insects of the order Coleoptera, i.e., beetles; and CryIV proteins are active against insects of the order Diptera, i.e., flies and mosquitoes. A compilation of the amino acid identities for several CryI proteins as well as CryII, CryIII and CryIV proteins has been determined in Hodgman and Ellar, *J. DNA Sequencing and Mapping*, 1, pp. 97–106 (1990).

The CryI family of ICPs contains the largest number of known toxin genes derived from *B.t.*, as evidenced by the survey in Höfte and Whiteley (1989) and by subsequent reports of CryI-type ICPs.

Schnepf et al., *J. Biol. Chem.*, 260, pp. 6264–6272 (1985), reported the complete nucleotide sequence for a toxin gene from *B.t. kurstaki* HD-1. This gene was subsequently classified as cryIA(a) by Höfte and Whiteley (1989). The published open reading frame extends 1176 amino acids and encodes a protein with a calculated molecular mass of 133,500 Daltons (Da). Another gene, also classified as cryIA(a), was isolated from *B.t.* subsp. *kurstaki* HD-1 Dipel® by Shibano et al., *Gene* 34, pp. 243–251 (1985). As detailed in Table 2 of Höfte and Whiteley (1989), this gene is highly related, especially in the N terminal moiety, to cryIA(a) reported by Schnepf et al. (1985). CryIA(a) protein is broadly active against Lepidoptera; Höfte and Whiteley (1989) reports that four of five tested lepidopteran insects were sensitive to this toxin.

Other ICP genes subsequently identified as cryIA(a) that are greater than 99% identical to the holotype cryIA(a) gene have been identified in *B. thuringiensis* subspecies *aizawai*, (Shimizu et al., *Agric. Biol. Chem.*, 52, pp. 1565–1573 (1988)), subspecies *kurstaki*, (Kondo et al., *Agric. Biol. Chem.*, 51, pp. 455–463 (1987)), and subspecies *entomocidus* (Masson et al., *Nucleic Acids Res.* 17, p. 446 (1989)). The cryI-type nucleotide sequence disclosed in European Patent Application Publication No. 0 367 474, published May 9, 1990, of Mycogen Corporation, reveals a DNA sequence related to the cryIA(a) gene and its encoded protein that is 92% positionally identical to the holotype CryIA(a) ICP.

Wabiko et al., *DNA*, 5, pp. 305–314 (1986), describe the DNA sequence of an insecticidal toxin gene from *B.t.* subsp. *berliner* 1715, subsequently classified as cryIA(b) by Höfte and Whiteley (1989). The molecular mass of the protein encoded is 130,615 Da and sequential deletions indicate that the $NH_2$-terminal 612 amino acid polypeptide is toxic to lepidopteran insects. Höfte et al., *Eur. J. Biochem.*, 161, pp. 273–280 (1986), describe the cloning and nucleotide sequencing of a variant crystal protein gene from *B.t.* subsp. *berliner* 1715, subsequently also classified as cryIA(b). The cloned gene produces an approximately 130,000 Da protein which coincides with the mass of the major protein observed in the strain. The gene has an open reading frame of 3465 bases which would encode a protein 1155 amino acids in length having a mass of 130,533 Da. Similarities of this sequence to the previously reported sequences for the cloned crystal genes from *B.t. kurstaki* HD-1, *B.t. kurstaki* HD-73 and *B.t. sotto* are discussed in the Höfte et al. (1986) paper. Data identifying a minimal toxic fragment required for insecticidal activity are also presented. The cryIA(b) gene discussed in Höfte et al. (1986) differs in its deduced amino acid sequence by only two amino acids from the CryIA(b) protein reported by Wabiko et al.

Other cryIA(b) genes have been disclosed in Geiser et al., *Gene*, 48, pp. 109–118 (1986), Hefford et al., *J. Biotechnol.*, 6, pp. 307–322 (1987), Oeda et al., *Gene*, 53, pp. 113–119 (1987), Kondo et al., supra, Fischhoff et al., *Bio/Technology*, 5, pp. 807–813 (1987) and Haider and Ellar, *Nucl. Acids Res.*, 16, p. 10927 (1988). Each of these six CryIA(b) ICPs is greater than 99% positionally identical to the holotype CryIA(b) toxin.

Adang et al., *Gene*, 36, pp. 289–300 (1985), report the cloning and complete nucleotide sequence of a crystal protein gene harbored on the 75 kilobase (kb) plasmid of strain *B.t.* subsp. *kurstaki* HD-73. The restriction map in the article identified this gene as holotype cryIA(c) under the current classification system of Höfte and Whiteley (1989). The complete sequence of the gene, spanning 3537 nucleotide base pairs (bp), coding for 1178 amino acids and potentially encoding a protein of 133,330 Da, is shown in the article. Toxicity data against *Manduca sexta* for the protein made by the cryIA(c) gene are also presented. CryIA(c) toxins have been isolated from several strains of *B.t.* subsp. *kenyae* that are highly related to the above-noted CryIA(c) toxin from *B.t.* subsp. *kurstaki* (greater than 99% positionally identical in deduced amino acid sequence) but whose protein products, although broadly active against lepidopteran insects, nonetheless show quantitatively different toxicities for individual insect species (Von Tersch et al., *Appl. Environ. Microbiol.*, 57, pp. 349–358 (1991)).

Brizzard et al., *Nucleic Acids Res.*, 16, pp. 2723–2724 (1988), describe the nucleotide sequence of crystal protein gene cryA4 (subsequently classified as cryIB by Höfte and Whiteley (1989)) isolated from *B.t.* subsp. *thuringiensis* HD-2. Höfte and Whiteley (1989) report an insecticidal specificity of CryIB toxin for *Pieris brassicae*.

Honee et al., *Nucleic Acids Res.*, 16, p. 6240 (1988), describe the complete DNA sequence for the BTVI crystal protein gene isolated from *B.t.* subsp. *entomocidus* 60.5 (holotype cryIC by Höfte and Whiteley (1989)). This protein is reported to exhibit enhanced insecticidal activities against *Spodoptera* species.

Sanchis et al., *Mol. Microbiol.*, 3, pp. 229–238 (1989) report the nucleotide sequence for the N-terminal coding region (2470 nucleotides) and 5' flanking region of a gene from *B.t.* subsp. *aizawai* 7.29 now classified as the cryIC gene under the classification system of Höfte and Whiteley (1989). Sanchis et al. disclose similar information about the cryIC gene in European Patent Application Publication No. 0 295 156, published Dec. 14, 1988. The open reading frame encodes a truncated polypeptide 824 amino acids long with a calculated mass of 92,906 Da.

A gene isolated from *B.t.* subspecies *aizawai* and now classified as holotype cryID under the Höfte and Whiteley (1989) system is disclosed in European Patent Application Publication No. 0 358 557, published Mar. 14, 1990 of Plant Genetic Systems, N.V. Höfte and Whiteley (1989) report selective lepidopteran toxicity against *Manduca sexta* for the CryID protein, the CryID toxin being largely inactive against other lepidopteran insects tested.

The holotype cryIE gene, found in a *B.t.* subspecies *darmstadiensis* strain, is disclosed in European Patent Application Publication No. 0 358 557, supra. A highly related cryIE gene from *B.t.* subsp. *kenyae* is disclosed by Visser et al., *J. Bacteriol.*, 172, pp. 6783–6788 (1990).

Visser, *Mol. Gen. Genet.*, 212, pp. 219–224 (1988) report the isolation and analysis of five toxin genes belonging to four different gene families from *B.t. entomocidus* 60.5, one of which is reported by Honee et al. (1988), supra. Two of these genes, BTIV and BTVIII, are cryIA(a)-type genes according to the Höfte and Whiteley (1989) classification scheme. The BTVI gene, also reported by Honee et al. (1988) supra, is a cryIC gene according to the Höfte and Whiteley (1989) classification scheme. The authors state that the restriction map for another gene, designated BTV, closely resembles that identified for the cryID gene isolated from *B.t.* strain HD68 subsp. *aizawai*, and disclosed in European Patent Application Publication No. 0 358 557, supra. A fifth gene, designated BTVII, is also identified and its restriction map differs significantly from the other four genes described. Toxicity data against several lepidopteran insects, *S. exigua*, *S. littoralis*, *H. virescens* and *P. brassicae*, are presented for each of the isolates. The BTV gene product was inactive against all insects tested. The BTVI protein is highly active against *Spodoptera* larvae, and the BTVII protein is toxic to *P. brassicae*.

Additional genes within the cryI family have been reported in the literature. A gene found in *B.t.* subsp. *aizawai* and described as cryIF is disclosed by Chambers et al. in *J. Bacteriol.*, 173, pp. 3966–3976 (1991) and in PCT International Publication No. WO91/16434, published Oct. 31, 1991. A gene described as cryIG from *B.t.* subsp. *galleria* is disclosed by Smulevitch et al., *FEBS Lett.*, 293, pp. 25–28 (1991). A gene that is highly related to the cryIG gene has been isolated from *B.t.* DSIR 517 by Gleave et al., *J. Gen. Microbiol.*, 138, pp. 55–62 (1992).

A novel gene related to cryI-type genes is disclosed in PCT International Publication No. WO 90/13651, published Nov. 15, 1990, of Imperial Chemical Industries PLC. This gene encodes an 81 kDa polypeptide (Cry pJH11) that is broadly insecticidal and more distantly related to the family of cryI sequences than are most other reported cryI-type sequences. Four cryI-type sequences are disclosed in European Patent Application Publication No. 0 405 810, published Jan. 2, 1991, of Mycogen Corporation. Inspection of the cryI-type sequences revealed that one of the disclosed genes (cry 81IB2) belongs to the cryIC class, one (cry 81IB) belongs to the cryID class, and one (cry 81IA) belongs to the cryIF class. The fourth disclosed cryI sequence (cry 81IA2) appears to belong to a new class. Two cryI sequences are disclosed in European Patent Application Publication No. 0 401 979, published Dec. 12, 1990, of Mycogen Corporation. One of the disclosed sequences (PS82A2) appears to encode a novel gene, the other sequence (PS82RR) is highly related to the novel sequence cry 81IA2 disclosed in European Patent Application Publication No. 0 405 810.

Five novel cry sequences are disclosed in European Patent Application Publication No. 0 462 721, published Dec. 27, 1991, of Mycogen Corporation. These Cry proteins are reported to be nematocidal.

SUMMARY OF THE INVENTION

Briefly stated, one aspect of the present invention relates to a purified, isolated cryET4 gene having a nucleotide base sequence coding for the amino acid sequence shown in FIG. 1 and listed in SEQ ID NO:2.

The isolated cryET4 gene has a coding region extending from nucleotide bases 99 to 3602 (including the stop codon) in the nucleotide base sequence shown in FIG. 1 and listed in SEQ ID NO:1.

The present invention also relates to the isolated CryET4 protein which is obtainable from the cryET4 gene, and which has the amino acid sequence shown in FIG. 1 (SEQ ID NO:2), and which is insecticidal to lepidopteran insects.

Another aspect of the present invention relates to a purified, isolated cryET5 gene having a nucleotide base sequence coding for the amino acid sequence shown in FIG. 2 and listed in SEQ ID NO:4.

The isolated cryET5 gene has a coding region extending from nucleotide bases 67 to 3756 (including the stop codon) in the nucleotide base sequence shown in FIG. 2 and listed in SEQ ID NO:3.

The present invention also relates to the isolated CryET5 protein which is obtainable from the cryET5 gene, and which has the amino acid sequence shown in FIG. 2 (SEQ ID NO:4), and which is insecticidal to lepidopteran insects.

Additionally, the present invention relates to biologically pure cultures of a *Bacillus thuringiensis* bacterium designated as strain EG7279 transformed with a cryET4 gene having a coding region listed in SEQ ID NO:1 and strain EG7283 transformed with a cryET5 gene having a coding region listed in SEQ ID NO:3 or mutants thereof having insecticidal activity against lepidopteran insects susceptible to the CryET4 and CryET5 proteins, respectively.

The invention also relates to a biologically pure culture of a *Bacillus thuringiensis* bacterium designated as strain EG5847 or mutants thereof having insecticidal activity against lepidopteran insects susceptible to *B.t.* strain EG5847. *B.t.* strain EG5847 is a wild type isolate and is the *B.t.* strain from which the cryET4 and cryET5 genes were isolated.

Additional aspects of the present invention relate to recombinant plasmids containing the cryET4 and cryET5 genes; bacteria transformed with the recombinant plasmids and capable of expressing the cryET4 and/or cryET5 genes; insecticide compositions comprising the proteins and/or one or both of the transformed bacteria and/or other bacteria containing the CryET4 or CryET5 protein, with an agriculturally acceptable carrier; a method of controlling lepidopteran insects using the insecticides; plants transformed with and capable of expressing the cryET4 and/or cryET5 genes; and hybridization probes containing the cryET4 or cryET5 gene wherein the gene or at least an oligonucleotide portion of it is labeled for such use.

BRIEF DESCRIPTION OF THE DRAWINGS

FIG. 1 comprises FIGS. 1A through 1J and shows the nucleotide sequence of the cryET4 gene (SEQ ID NO:1) and the deduced amino acid sequence of the CryET4 protein (SEQ ID NO:2).

FIG. 2 comprises FIGS. 2A through 2J and shows the nucleotide sequence of the cryET5 gene (SEQ ID NO:3) and the deduced amino acid sequence of the CryET5 protein (SEQ ID NO:4).

FIG. 5 comprises FIGS. 5A and 5B and is a restriction map of the recombinant plasmids pEG291 (5A) and pEG1108 (5B), both of which contain the cloned cryET4 gene. The location and orientation of the cryET4 gene are indicated by the arrow.

FIG. 6 comprises FIGS. 6A, 6B, 6C and 6D and is a restriction map of the recombinant plasmids pEG292 (6A), pEG300 (6B), pEG1110 (6C) and pEG1111 (6D). Plasmids pEG292 and pEG300 contain 5' and 3' portions of the cryET5 gene, respectively. Plasmids pEG1110 and pEG1111 contain the entire cloned cryET5 gene. The location and direction of transcription of the cryET5 gene are indicated by the arrows.

DETAILED DESCRIPTION OF THE PREFERRED EMBODIMENTS

Figure 3:
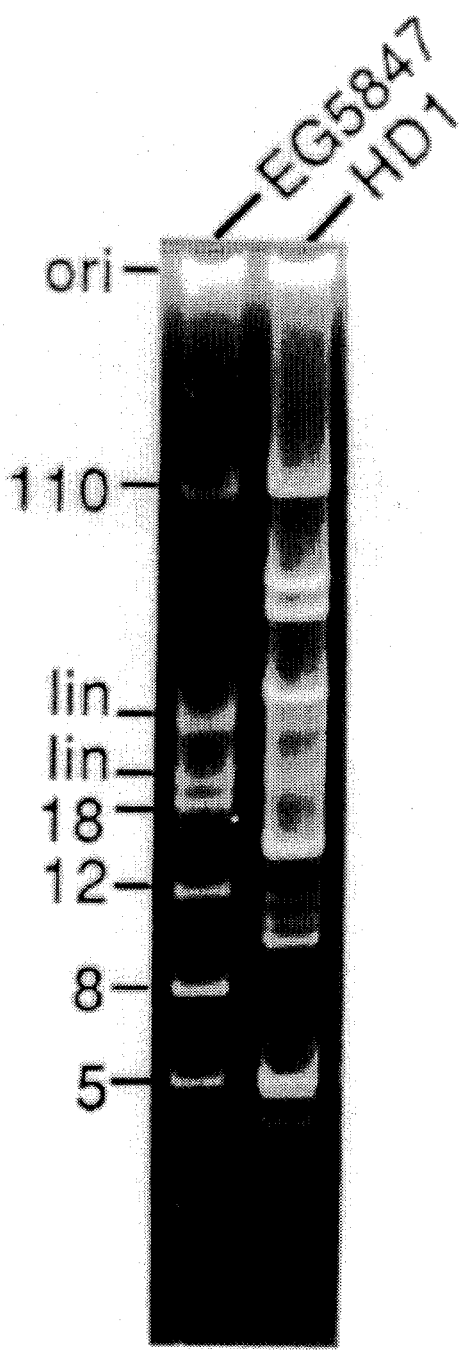
FIG. 3 is a photograph of an ethidium bromide stained agarose gel containing size-fractionated plasmids of *B.t.* strains EG5847 and HD-1, with plasmid sizes in megadaltons (MDa) being shown. The abbreviations in FIG. 3 are as follows: "ori" indicates the loading site and "lin" means linear DNA.

Two novel *Bacillus thuringiensis* (*B.t.*) toxin genes, designated cryET4 (SEQ ID NO:1) and cryET5 (SEQ ID NO:3), were obtained from a novel *B.t.* isolate designated EG5847. Isolation of *B.t.* strain EG5847, isolation of the novel toxin genes cryET4 and cryET5, construction of Bacillus/*E. coli* shuttle vectors containing cryET4 (pEG1108) and cryET5 (pEG1111), and transformation of pEG1108 and pEG1111 into a *B.t.* host (*B.t.* strain EG10368) to produce recombinant *B.t.* strains EG7279 and EG7283 expressing respectively the CryET4 (SEQ ID NO:2) and CryET5 (SEQ ID NO:4) toxin protein gene products, are described generally in the Examples.

Subcultures of *B.t.* strains EG5847, EG10368, EG7279 and EG7283 were deposited in the permanent collection of the Agricultural Research Service Culture Collection, Northern Regional Research Laboratory (NRRL), U.S. Department of Agriculture, 1815 North University Street, Peoria, Ill. 61604, U.S.A. The accession numbers and deposit dates are as follows:

| Subculture | Accession No. | Deposit Date |
| --- | --- | --- |
| B.t. EG5847 | NRRL B-21110 | June 9, 1993 |
| B.t. EG10368 | NRRL B-21125 | July 20, 1993 |
| B.t. EG7279 | NRRL B-21112 | June 9, 1993 |
| B.t. EG7283 | NRRL B-21111 | June 9, 1993 |

These microorganism deposits were made under the provisions of the "Budapest Treaty on the International Recognition of the Deposit of Microorganism for the Purposes of Patent Procedure." All restrictions on the availability to the public of these deposited microorganisms will be irrevocably removed upon issuance of a U.S. patent based on this application.

The present invention is intended to cover mutants and recombinant or genetically engineered derivatives, e.g., truncated versions, of the cryET4 gene listed in SEQ ID NO:1 and the cryET5 gene listed in SEQ ID NO:3 that yield a protein with insecticidal properties essentially the same as those of the CryET4 protein listed in SEQ ID NO:2 and the CryET5 protein listed in SEQ ID NO:4. Likewise, the present invention covers those gene nucleotide base sequences that encode the amino acid sequences of the CryET4 protein (SEQ ID NO:2) and the CryET5 protein (SEQ ID NO:4). Variations may be made in the cryET4 and cryET5 gene nucleotide base sequences shown in FIGS. 1 and 2, respectively, and listed in SEQ ID NO:1 and SEQ ID NO:3, respectively, which do not affect the amino acid sequence of the gene product, since the degeneracy of the genetic code is well known to those skilled in the art. Moreover, there may be some variations or truncations in the coding regions of the cryET4 and cryET5 nucleotide base sequences which allow expression of the gene and production of functionally equivalent forms of the CryET4 and CryET5 insecticidal proteins. These variations or truncations, which can be determined without undue experimentation by those of ordinary skill in the art with reference to the present specification, are to be considered within the scope of the appended claims, since they are fully equivalent to the specifically claimed subject matter.

It has been shown that proteins of identical structure and function may be constructed by changing the amino acid sequence, if such changes do not alter the protein secondary structure (Kaiser and Kezdy, *Science*, 223, pp. 249–255 (1984)). Single amino acid substitutions have been introduced by site-directed mutagenesis at various positions of CryIA(a) toxin protein without altering the insecticidal properties of the parent toxin (Ge et al., *Proc. Natl. Acad. Sci. USA*, 86, pp. 4037–4041 (1989)). The present invention includes mutants of the amino acid sequences disclosed herein which have an unaltered protein secondary structure or, if the structure is altered, where the mutant has retained substantially equivalent biological activity compared to the unaltered protein.

The cryET4 gene (SEQ ID NO:1) and cryET5 (SEQ ID NO:3) gene are also useful as DNA hybridization probes, for discovering similar or closely related cryET4-type and cryET5-type genes in other *B.t.* strains. The cryET4 gene (SEQ ID NO:1) and cryET5 gene (SEQ ID NO:3), or unique portions or derivatives thereof capable of hybridizing selectively to a target nucleic acid, e.g., homologous oligonucleotides of 12 or more nucleotides, or larger portions of the genes, that contain nucleotide sequences unique to the cryET4 gene or cryET5 gene and that are different from similar sized nucleotide segments in known, prior art *B.t.* toxin genes, can be labeled for use as hybridization probes using conventional procedures. An exemplary label is a radioactive label.

Both the cryET4 gene (SEQ ID NO:1), its corresponding insecticidal CryET4 protein (SEQ ID NO:2) and the cryET5 gene (SEQ ID NO:2) and its corresponding insecticidal CryET5 protein (SEQ ID NO:4) were first identified in *B.t.* strain EG5847, a novel *B.t.* isolate. The characteristics of *B.t.* strain EG5847 are more fully described in the Examples.

The Bacillus strains described herein may be cultured using conventional growth media and standard fermentation techniques. The *B.t.* strains harboring the cryET4 gene (SEQ ID NO:1) or the cryET5 gene (SEQ ID NO:3), or both genes, may be fermented, as described in Example 1, until the cultured *B.t.* cells reach the stage of their growth cycle when the CryET4 crystal protein (SEQ ID NO:2) or the CryET5 crystal protein (SEQ ID NO:4) is formed. For sporogenous *B.t.* strains, fermentation is typically continued through the sporulation stage when the crystal protein is formed along with spores. The *B.t.* fermentation culture is then typically harvested by centrifugation, filtration or the like to separate fermentation culture solids containing the crystal protein from the culture medium.

The separated fermentation solids are primarily CryET4 crystal protein (SEQ ID NO:2) or CryET5 crystal protein (SEQ ID NO:4) and *B.t.* spores (if a sporulating host is employed), along with some cell debris, some intact cells and residual fermentation medium solids. If desired, the crystal protein may be separated from the other recovered solids via conventional methods, e.g., density gradient fractionation.

The *B.t.* strains exemplified in this disclosure are sporulating varieties (spore forming or sporogenous strains) but the cryET4 gene (SEQ ID NO:1) and cryET5 gene (SEQ ID NO:3) also have utility in asporogenous Bacillus strains, i.e., strains that produce the crystal protein without production of spores. It should be understood that references to "fermentation cultures" of *B.t.* strains containing the cryET4 gene (SEQ ID NO:1) or the cryET5 gene (SEQ ID NO:3) in this disclosure are intended to cover sporulated *B.t.* cultures, i.e., *B.t.* cultures containing the CryET1 crystal protein and spores, and sporogenous Bacillus strains that have produced crystal proteins during the vegetative stage, as well as asporogenous Bacillus strains containing the cryET4 gene (SEQ ID NO:1) or cryET5 (SEQ ID NO:3) gene in which the culture has reached the growth stage where the crystal protein is actually produced.

Mutants of *B.t.* strains harboring the cryET4 gene (SEQ ID NO:1) or cryET5 gene (SEQ ID NO:3) can be made by procedures well known in the art. For example, an asporogenous mutant can be obtained through ethylmethane sulfonate mutagenesis. Mutants can also be made using ultraviolet light and nitrosoguanidine by procedures that are well known to those skilled in the art. References in this specification to "mutants" of wild-type or recombinant *B.t.* strains harboring the cryET4 gene or cryET5 gene refer to those derivatives which are capable of producing toxin protein exhibiting insecticidal activity against lepidopteran insects, at least equivalent to the insecticidal activity of the parent strain.

The CryET4 protein (SEQ ID NO:2) is an insecticidal compound active against a large number of lepidopteran insects, particularly those described in Example 4. The CryET4 protein (SEQ ID NO:2) may be used as the active ingredient in insecticidal formulations useful for controlling lepidopteran insects.

The CryET5 protein (SEQ ID NO:4) is an insecticidal compound active against a large number of lepidopteran insects, particularly those described in Example 4. The CryET5 protein (SEQ ID NO:4) may be used as the active ingredient in insecticidal formulations useful for controlling lepidopteran insects.

Such insecticidal formulations or compositions typically contain agriculturally acceptable carriers or adjuvants in addition to the active ingredient and are prepared and used in a manner well known to those skilled in the art.

The CryET4 protein (SEQ ID NO:2) or CryET5 protein (SEQ ID NO:4) may be employed in insecticidal formulations in isolated or purified form, e.g., as the crystal protein itself. Alternatively, the CryET4 protein (SEQ ID NO:2) or CryET5 protein (SEQ ID NO:4) may be present in the recovered fermentation solids, obtained from culturing of a Bacillus strain, e.g., *Bacillus thuringiensis* or other microorganism host carrying the cryET4 gene (SEQ ID NO:1) or cryET5 gene (SEQ ID NO:3) and capable of producing the CryET4 or CryET5 protein. The CryET4 protein or CryET5 protein is thus associated with the *B.t.* bacterium which produced the protein, as an intimate mixture of crystal protein, cell debris and spores, if any, in the recovered fermentation solids. The recovered fermentation solids containing the CryET4 or CryET5 protein may be dried, if desired, prior to incorporation in the insecticidal formulation. Genetically engineered or transformed *B.t.* strains or other host microorganisms containing a recombinant plasmid that expresses the cloned cryET4 gene (SEQ ID NO:1) or cryET5 gene (SEQ ID NO:3), obtained by recombinant DNA procedures, may also be used. For construction of recombinant *B.t.* strains containing either the cryET4 gene or cryET5 gene, *B.t.* var. *kurstaki* strain EG10368 is a preferred host, and this *B.t.* strain is utilized in Example 2. *B.t.* strain EG10368 is a crystal-negative, toxin plasmid-free, naturally occurring mutant of *B.t.* strain HD73-26 (described in U.S. Pat. No. 5,080,897, issued to Gonzalez, Jr. et al. on Jan. 14, 1992) that is highly transformable with recombinant plasmids, particularly those isolated from *E. coli* strains, e.g., DH5α.

The formulations or compositions of this invention containing the insecticidal CryET4 protein (SEQ ID NO:2) or CryET5 protein (SEQ ID NO:4) as the active component are applied at an insecticidally effective amount which will vary depending on such factors as, for example, the specific lepidopteran insects to be controlled, the specific plant or crop to be treated and the method of applying the insecticidally active compositions.

The insecticide compositions are made by formulating the insecticidally active component with the desired agriculturally acceptable carrier. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally acceptable carrier" covers all adjuvants, e.g., inert components, dispersants, surfactants, tackifiers, binders, etc. that are ordinarily used in insecticide formulation technology; these are well known to those skilled in insecticide formulation.

The formulations containing the CryET4 protein (SEQ ID NO:2) or CryET5 protein (SEQ ID NO:4) and one or more solid or liquid adjuvants are prepared in known manners, e.g., by homogeneously mixing, blending and/or grinding the insecticidally active CryET4 or CryET5 protein component with suitable adjuvants using conventional formulation techniques.

The insecticidal compositions of this invention are applied to the environment of the target lepidopteran insect, typically onto the foliage of the plant or crop to be protected, by conventional methods, preferably by spraying. Other application techniques, e.g., dusting, sprinkling, soaking, soil injection, seed coating, seedling coating or spraying, or the like, are also feasible and may be required for insects that cause root or stalk infestation. These application procedures are well known in the art.

The cryET4 gene (SEQ ID NO:1) or cryET5 gene (SEQ ID NO:3) may be introduced into a variety of microorganism hosts without undue experimentation, using procedures well known to those skilled in the art for transforming suitable hosts under conditions which allow for stable maintenance and expression of the cloned genes. Maniatis et al., *Molecular Cloning: A Laboratory Manual*, Cold Spring Harbor Laboratory Press, Cold Spring Harbor, N.Y. (1982). Suitable hosts that allow the cryET4 gene (SEQ ID NO:1) or cryET5 gene (SEQ ID NO:3) gene to be expressed and the CryET4 protein (SEQ ID NO:2) or CryET5 protein (SEQ ID NO:4) to be produced include *B.t.* and other *Bacillus* species such as *B. subtilis* or *B. megaterium*. A general method for the transformation of Bacillus strains is provided by Macaluso et al. in *J. Bacteriol.*, 173, pp. 1353–1356 (1991) and Mettus et al. in *Appl. Environ. Microbiol.*, 56, pp. 1128–1134 (1990). Genetically altered or engineered microorganisms containing the cryET4 gene (SEQ ID NO:1) or cryET5 gene (SEQ ID NO:3) can also contain other toxin genes present in the same microorganism; these genes could concurrently produce ICPs different from the CryET4 protein or CryET5 protein.

Plant-colonizing or root-colonizing microorganisms may also be employed as the host for the cryET4 gene (SEQ ID NO:1) or cryET5 gene (SEQ ID NO:3). Exemplary microorganism hosts for *B.t.* toxin genes include the plant-colonizing microbe *Clavibacter xyli* subsp. *cynodontis*, as described by Turner et al. in *Appl. Environ. Microbiol.*, 57, pp. 3522–3528, and root-colonizing pseudomonad strains, as described by Obukowicz et al. in *Gene*, 45, pp. 327–331 (1986). Procedures such as those described by Turner et al. (1991) supra, and Obukowicz et al. (1986), supra, are well known to those skilled in the art and available for introducing the cryET4 gene (SEQ ID NO:1) or cryET5 gene (SEQ ID NO:3) into such microorganism hosts under conditions which allow for stable maintenance and expression of the gene in the resulting transformants.

The transformants, i.e., host microorganisms that harbor a cloned gene in a recombinant plasmid, can be isolated in accordance with conventional methods, usually employing a selection technique, which allows growth of only those host microorganisms that contain a recombinant plasmid. The transformants then can be tested for insecticidal activity. These techniques are standard procedures well known to those skilled in the art.

Characteristics of particular interest in selecting a host cell for purposes of production include ease of introducing the gene into the host, availability of expression systems, efficiency of expression, stability of the CryET4 or CryET5 insecticidal protein in the host, and the presence of auxiliary genetic capabilities. The cellular host containing the insecticidal cryET4 gene (SEQ ID NO:1) or cryET5 gene (SEQ ID NO:3) may be grown in any convenient nutrient medium, where expression of the cryET4 gene or cryET5 gene is obtained and CryET4 protein (SEQ ID NO:2) or CryET5 protein (SEQ ID NO:4) produced, typically to sporulation. The sporulated cells containing the crystal protein may then be harvested in accordance with conventional methods, e.g., centrifugation or filtration.

The cryET4 gene (SEQ ID NO:1) or cryET5 gene (SEQ ID NO:3), particularly the toxin portion (N-terminal moiety) thereof, may also be incorporated into a plant which is capable of expressing the gene and producing CryET4 protein (SEQ ID NO:2) or CryET5 protein (SEQ ID NO:4), rendering the plant more resistant to insect attack. Genetic engineering of plants with the cryET4 gene (SEQ ID NO:1) or cryET5 gene (SEQ ID NO:3) may be accomplished by introducing the desired DNA containing the gene into plant tissues or cells, using DNA molecules of a variety of forms and origins that are well known to those skilled in plant genetic engineering. Examples of techniques for introducing DNA into plant tissue are disclosed in European Patent Application Publication No. 0 289 479, published Nov. 1, 1988, of Monsanto Company and by Perlak et al. in "Modification of the Coding Sequence Enhances Plant Expression of Insect Control Protein Genes," *Proc. Natl. Acad. Sci. USA*, 88, pp. 3324–3328 (1991).

DNA containing the cryET4 gene (SEQ ID NO:1) or cryET5 gene (SEQ ID NO:3) or a modified gene, operatively associated with a suitable plant promoter, e.g., CaMV35S, capable of effecting production of the CryET4 protein (SEQ ID NO:2) or CryET5 protein (SEQ ID NO:4), may be delivered into the plant cells or tissues directly by infectious plasmids, such as Ti, the plasmid from *Agrobacterium tumefaciens*, viruses or microorganisms like *A. tumefaciens*. Additionally, the use of lysosomes or liposomes, microinjection by mechanical methods and by other techniques familiar to those skilled in plant genetic engineering may be used.

The basic methods employed in the construction and evaluation of the recombinant plasmids and recombinant microorganism hosts described in this specification are generally well know to those proficient in the art of molecular cloning. Descriptions of these general laboratory procedures and definitions of nomenclature may be found in Maniatis et al., *Molecular Cloning: A Laboratory Manual*, Cold Spring Harbor Laboratory Press, Cold Spring Harbor, N.Y. (1982) and in a subsequent edition by Sambrook et al. (1989).

The characteristics of the CryET4 protein (SEQ ID NO:2) and CryET5 protein (SEQ ID NO:4), sequencing of the cryET4 gene (SEQ ID NO:1) and cryET5 gene (SEQ ID NO:3), comparison of sequence data to known *B.t.* toxin genes and insecticidal activity of the CryET4 and CryET5 proteins are described in the following specific, non-limiting examples.

EXAMPLE 1

Characterization of *B.t.* EG5847

*B.t.* strain EG5847 is a wild-type isolate, identified by visual examination of the colony as exhibiting a unique crystal morphology, and was isolated as a colony from maize dust. The colony contained endospores and bipyramidal and flat, diamond-shaped crystalline inclusions. Subsequent insect bioassay of this wild-type *B.t.* strain confirmed its insecticidal activity towards lepidopteran insects.

The complement of native plasmids contained within isolated *B.t.* EG5847 was determined by modified Eckhardt agarose gel electrophoresis as described by González, Jr. et al., in *Proc. Natl. Acad. Sci. USA*, 79, pp. 6951–6955 (1982). The results, as shown in FIG. 3, revealed the presence of 5, 8, 12, 18 and 110 MDa plasmids. This pattern of native plasmids did not correspond to patterns typical of known serovars (Carlton and González, pp. 246–252, in *Molecular Biology of Microbial Differentiation*, J. A. Hoch and P. Setlow, ed., American Society for Microbiology, Washington, D.C. (1985)).

Wild-type *B.t.* strain EG5847 was grown for five days at 25° C. in DSM medium (described by Donovan et al. in *Appl. Environm. Microbiol.*, 58, pp. 3921–3927 (1992)) until sporulation and cell lysis had occurred. Recombinant *B.t.* strains EG7279 (Example 2), containing the cryET4 gene, and EG7283 (Example 2), containing the cryET5 gene, were grown in DSM medium containing 3 µg of chloramphenicol per ml in a similar manner. Fermentation solids containing spores and crystal proteins were isolated by centrifugation. Crystal proteins were purified from the spores and cell debris by sucrose density gradient centrifugation (described by Koller et al. in *Biochem. Biophys. Res. Communic.*, 184, pp. 692–699 (1992)). Aliquots of the washed crystals were solubilized by heating in Laemmli buffer (10% (w/w) glycerol, 5% (w/w) 2-mercaptoethanol, 1% (w/v) SDS, 0.188M Tris HCl pH 6.8, 0.01% (v/v) bromphenol blue) at 100° C. for 5 minutes. The solubilized crystal proteins were size fractionated by SDS-polyacrylamide gel electrophoresis. After size fractionation, the proteins were visualized by staining with Coomassie Blue R-250 dye.

Figure 4:
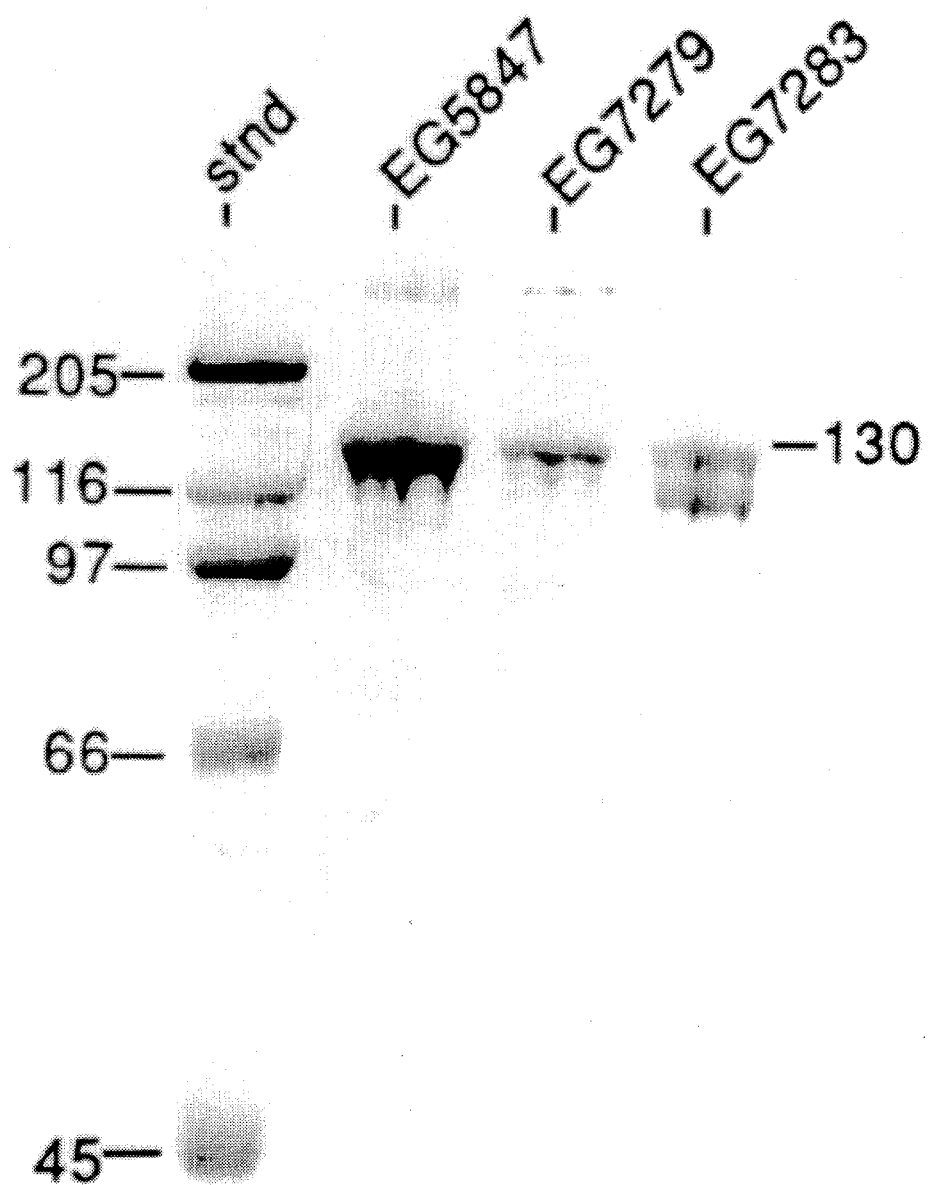
FIG. 4 is a photograph of a Coomassie blue stained gel containing size-fractionated proteins from *B.t.* strains EG5847, EG7279 and EG7283, obtained by sodium dodecyl sulfate polyacrylamide gel electrophoresis (SDS-PAGE).

FIG. 4 shows the results of these protein size fractionation analyses where lane 1 is a molecular mass size standard, lane 2 is *B.t.* strain EG5847, lane 3 is *B.t.* strain EG2729 and lane 4 is *B.t.* strain EG7283. The numbers on the left side indicate the apparent molecular masses, in kilodaltons (kDa), of the crystal proteins synthesized by the *B.t.* strains. As shown in lane 3, a crystal protein having a mass of approximately 130 kDa was observed from EG7279. As shown in lane 4 for EG7283, a crystal protein having a mass of approximately 130 kDa was produced. The wild type strain EG5847 exhibited a large protein band of approximately 130 kDa. The observed masses of the crystal proteins are in agreement with the masses predicted from the DNA sequences obtained in Example 3.

EXAMPLE 2

Cloning of the cryET4 and cryET5 Genes

Genomic DNA was isolated from *B.t.* strain EG5847 and then digested with HindIII. cryI-like genes were identified by Southern blotting (described by Southern, *J. Mol. Biol.* 98, pp. 503–517 (1975)). A radiolabelled 700 bp EcoR1 fragment of the cryIA(a) gene (described by Schnepf et al., *J. Biol. Chem.*, 260, pp. 6264–6272 (1985)) was used as a hybridization probe to identify cryI-like genes containing HindIII restriction fragments of EG5847 DNA. The 700 bp cryIA(a) fragment hybridized to several HindIII restriction fragments of EG5847 DNA including fragments of approximately 5.0 kb and 4.7 kb.

The 5.0 kb and 4.7 kb cryIA(a)-hybridizing HindIII restriction fragments of *B.t.* strain EG5847 were cloned as follows. DNA fragments of approximately 4–8 kb from HindIII digests of EG5847 genomic DNA were purified by agarose gel electrophoresis and electroelution. These fragments were ligated to the *E. coli* plasmid vector pUC18 and the ligation mixture was then used to transform *E. coli*. Ampicillin-resistant *E. coli* colonies were blotted to nitrocellulose filters (Grunstein et al., *Proc. Natl. Acad. Sci. USA* 72, pp. 3961–3965 (1975)). The filters were probed with the radiolabelled 700 bp cryIA(a) gene fragment. Two positive colonies, designated as *E. coli* strains EG7286 and EG7287, were identified and were selected for further analysis.

HindIII digestion of a plasmid, designated pEG291, isolated from *E. coli* strain EG7286 revealed a HindIII insert fragment 5.0 kb in size in pUC18. The restriction map of plasmid pEG291 is shown in FIG. 5A.

An *E. coli/B. thuringiensis* shuttle vector containing the 5.0 kb HindIII fragment was constructed by ligating BamHI digested Bacillus plasmid pNN101 (Norton et al., *Plasmid*, 13, pp. 211–214 (1985)) into the unique BamHI site of pEG291 (FIG. 5B). The resulting plasmid, designated pEG1108 (FIG. 5B), contains a full length open reading frame which has been designated as the cryET4 gene (SEQ ID NO:1).

*E. coli* strain EG7287 contained a plasmid, designated pEG292, which had a 4.7 kb HindIII insert in pUC18. DNA sequencing as described in Example 3 indicated that an open reading frame present in the 4.7 kb insert was truncated at its 3'-end (FIG. 6A). The truncated portion was isolated using a synthetic oligonucleotide having the sequence 5'-AAGTTTCGCATCCATCGATG-3' (SEQ ID NO:5). The oligonucleotide, designated WD162, was homologous to nucleotides 2253 to 2272 of the open reading frame identified in plasmid pEG292. Southern blot analyses as described above indicated that WD162 (SEQ ID NO:5) hybridized to a 3.2 kb HincII restriction fragment of EG5847 DNA. Radiolabelled WD162 was then used in colony blot experiments as described above to probe *E. coli* cells that contained a plasmid library consisting of size-selected HincII restriction fragments of EG5847 DNA. Several *E. coli* colonies hybridized with WD162 and one colony, designated *E. coli* strain EG7288, was selected for further analysis.

HincII restriction analysis of a recombinant plasmid, designated pEG300, isolated from *E. coli* EG7288, indicated that a 3.9 kb HincII fragment was present in pUC18. DNA sequencing as described below showed that pEG300 contained an open reading frame truncated at its 5'-end by the HincII cleavage site (FIG. 6B).

The full length open reading frame was constructed by excising a 2.6 kb XbaI-BsmI fragment containing the 5' portion of the open reading frame from plasmid pEG292 and inserting the fragment into the XbaI-BsmI restriction sites of plasmid pEG300 (FIG. 6A and 6B). The resulting plasmid, designated pEG1110 (FIG. 6C), contains a full length open reading frame which has been designated as the cryET5 gene (SEQ ID NO:3).

An *E. coli/B. thuringiensis* expression vector containing the full length open reading frame of the cryET5 gene was constructed by ligating XbaI digested Bacillus plasmid pNN101 (Norton, supra) into the unique XbaI site of plasmid pEG1110 (FIG. 6D). The resulting construct was designated plasmid pEG1111.

Plasmids pEG1108 and pEG1111 are capable of replicating in both *E. coli* and *B.t.* The plasmids were transformed by electroporation (Macaluso et al., *J. Bacteriol.*, 173, pp. 1353–1356 (1991)) into the acrystalliferous *B.t.* strain EG10368 resulting in *B.t.* strains EG7279 (pEG1108) and EG7283 (pEG1111), respectively containing the cryET4 and cryET5 genes. Both of these *B.t.* strains are capable of expressing their respective protein toxin genes, as described in Example 4.

EXAMPLE 3

Sequencing of the cryET4 and cryET5 Genes

The complete DNA sequence of the cryET4 gene was determined using plasmid pEG291 (Example 2). Plasmid pEG291 was sequenced by standard methods (Sanger et al., *Proc. Natl. Acad. Sci. USA*, 74, pp. 5463–5467 (1977)). The DNA sequences of the appropriate subclones of the 5.0 kb HindIII fragment were joined to give a continuous sequence of 3713 nucleotides which is shown in FIG. 1 and is designated as SEQ ID NO:1. Inspection of the sequence revealed an open reading frame beginning at position 99 and extending to position 3602 (including the stop codon). The gene has been designated cryET4. The deduced 1167 amino acid sequence of the gene product is shown in FIG. 1 and is designated as SEQ ID NO:2. The mass of the CryET4 protein (SEQ ID NO:2) encoded by the cryET4 gene (SEQ ID NO:1), as deduced from the open reading frame, is 132,774 Da. Among CryI-type protein toxins reported in the literature, the CryIA(a) protein appears to be most closely related to the CryET4 protein. CryET4 exhibits a 69% amino acid homology with CryIA(a).

The complete DNA sequence of the cryET5 gene (SEQ ID NO:3) was determined by the Sanger method as described above. Subcloned gene fragments from pEG292, pEG300 and pEG1110 were sequenced. The DNA sequences of the subcloned fragments were joined to give a continuous sequence of 3,934 nucleotides which is shown in FIG. 2 and is designated as SEQ ID NO:3. Inspection of the sequence revealed an open reading frame beginning at position 67 and extending to position 3756 (including the stop codon). The gene has been designated cryET5. The deduced 1229 amino acid sequence of the gene product encoded by the cryET5 gene (SEQ ID NO:3) is shown in FIG. 2 and is designated as SEQ ID NO:4. The mass of the CryET5 protein (SEQ ID NO:4) encoded by the cryET5 gene (SEQ ID NO:3), as deduced from the open reading frame, is 139,783 Da. Among CryI-type proteins reported in the literature, the CryIB protein appears to be most closely related to the CryET5 protein. CryET5 exhibits 83% amino acid homology with CryIB.

EXAMPLE 4

Insecticidal Activity of Recombinant Strains Harboring cryET4 and cryET5 Genes $PLC_{50}$ values of purified CryET4 and CryET5 crystal proteins were determined against lepidopteran insects, and these are listed in Tables 1 and 2, respectively. The $PLC_{50}$ dose is that amount of insecticidal crystal protein (ICP) which killed half of the insects tested, i.e., the median lethal concentration. CryET4 and CryET5 crystal proteins were isolated from *B.t.* strains EG7279 and EG7283, respectively, (described in Example 2) by sucrose density gradient centrifugation as described above. The amount of crystal protein recovered from the gradients was quantified by the Bradford protein assay (Bradford, *Anal. Biochem.*, 72, p. 248 (1976)) after solubilization of the recovered crystal proteins with base and a reducing agent. Known amounts of purified crystals were diluted in 0.005% Triton® X-100 (v/v). Aliquots of eight two-fold serial dilutions (50 μl) were applied to the surfaces of 32 wells (1.8 cm² surface area) containing insect diet and dried for 1 hour at 30° C. A general purpose Noctuidae artificial diet (E. G. King et al., *Handbook of Insect Rearing*, Vol. 2, P. Singh and R. F. Moore (eds.), pp. 323–328, Elsevier Science Publishers B.V., Amsterdam (1985)) was used for *Trichoplusia ni, Ostrinia nubilalis* and *Heliothis virescens*. Other standard diets were used for the other lepidopteran insects tested. One neonate larva (third-instar larva in the case of *P. xylostella*) was added to each well, and the wells were incubated at 30° C. Mortality was recorded after seven days.

The insecticidal activity of CryET4 protein was compared with the activity of CryIA(a) protein (Schnepf et al., *J. Biol. Chem.*, 260, pp. 6264–6272 (1985)). CryET4 exhibits a 69% amino acid sequence homology with CryIA(a). The results are presented in Table 1.

TABLE 1

| | $PLC_{50}$ Bioassay Activity of Purified CryET4 | |
|---|---|---|
| | $PLC_{50}$ (ng ICP/well) | |
| Insect Species | CryET4 | CryIA(a) |
| *Heliothis virescens* | 593 (493–711)** | 94 (76–113) |
| *Helicoverpa zea* | 1,290 (1,046–1,599) | 3,725 (3,004–4,551) |
| *Lymantria dispar* | 9,929 (5,767–26,039) | 185 (138–243) |
| *Ostrinia nubilalis* | 197 (121–299) | 34 (27–42) |
| *Pseudoplusia includens* | 33 (29–37) | 14 (12–16) |
| *Plutella xylostella* | 30 (22–41) | 12 (10–14) |
| Javelin ® *-resistant | | |
| *P. xylostella* | 4,758 (3,135–6,897) | >50,000 |
| *Spodoptera exigua* | 1,748 (1,286–2,591) | >20,000 |
| *Spodoptera frugiperda* | 1,161 (555–2,115) | >10,000 |
| *Trichoplusia ni* | 62 (53–74) | 80 (54–113) |

*Javelin is a commercial B.t. bioinsecticide.
**Range in parentheses indicates 95% confidence level.

The $PLC_{50}$ results in Table 1 indicate that the CryET4 protein (SEQ ID NO:2) exhibits good insecticidal activity to a broad spectrum of lepidopteran insects.

The results show that the CryET4 protein is more toxic than CryIA(a) against *Helicoverpa zea* (corn earworm/ bollworm), Javelin®-resistant *Plutella xylostella* (diamondback moth), *Spodoptera exigua* (beet armyworm) and *Spodoptera frugiperda* (fall armyworm).

Particularly noteworthy is the very good activity against *Spodoptera exigua* (beet armyworm), an insect pest that not only is not susceptible to CryIA(a), but also is recalcitrant to most *B.t.* toxin proteins, and very good activity against *Spodoptera frugiperda* (fall armyworm), another recalcitrant insect pest. Activity against *Pseudoplusia includens* (soybean looper), *Plutella xylostella* (diamondback moth) and *Trichoplusia ni* (cabbage looper) was also good, comparable to that exhibited by CryIA(a).

Insect bioassay tests with CryET4 protein were also carried out against another lepidopteran insect, *Agrotis ipsilon* (black cutworm), which was found not to be susceptible to control with CryET4.

The insecticidal activity of CryET5 protein was compared with the activity of CryIB protein (Brizzard et al., *Nucleic Acids Res.* 16, 2723–2724 (1988)). CryET5 exhibits an 83% amino acid sequence homology with CryIB. Dilutions of purified CryET5 crystals were prepared in 0.005% Triton® X-100. Aliquots of appropriate dilutions (50 μl) were applied to the surfaces of 32 wells and assayed as indicated above. The results are presented in Table 2.

TABLE 2

$PLC_{50}$ Bioassay Activity of Purified CryET5

| | $PLC_{50}$ (ng ICP/well) | |
|---|---|---|
| Insect Species | CryET5 | CryIB |
| *Lymantria dispar* | 880 (555–1,397)** | 3,580 (1,293–20,123) |
| *Ostrinia nubilalis* | 32 (29–37) | 83 (51–123) |
| *Pseudoplusia includens* | 555 (437–646) | 52 (44–61) |

TABLE 2-continued $PLC_{50}$ Bioassay Activity of Purified CryET5

| | $PLC_{50}$ (ng ICP/well) | |
|---|---|---|
| Insect Species | CryET5 | CryIB |
| *Plutella xylostella* Javelin® *-resistant | 157 (127–193) | 27 (23–32) |
| *P. xylostella* | 47 (23–80) | 43 (35–55) |
| *Spodoptera frugiperda* | 2,812 (1,831–4,514) | >10,000 |
| *Trichoplusia ni* | 22 (19–27) | 205 (176–241) |

*Javelin is a commercial B.t. bioinsecticide.
**Range in parentheses indicates 95% confidence level.

The $PLC_{50}$ results in Table 2 indicate that the CryET5 protein (SEQ ID NO:4) exhibits good insecticidal activity to a broad spectrum of lepidopteran insects.

The results show that the CryET5 protein is more toxic than CryIB against *Spodoptera frugiperda* (fall armyworm) and *Trichoplusia ni* (cabbage looper). The CryET5 protein and CryIB protein both exhibited excellent insecticidal activity against Javelin®-resistant *Plutella xylostella* (diamondback moth), a *B.t.*-resistant insect pest that is not susceptible to CryIA-type toxin proteins, and to *Ostrinia nubilalis* (European corn borer).

Insect bioassay tests with CryET5 protein were also carried out against a few other lepidopteran insects, but these were found not to be susceptible to control with CryET5: *Agrotis ipsilon* (black cutworm), *Heliothis virescens* (tobacco budworm), *Helicoverpa zea* (corn earworm/bollworm) and *Spodoptera exigua* (beet armyworm).

The present invention may be embodied in other specific forms without departing from the spirit or essential attributes thereof and, accordingly, reference should be made to the appended claims, rather than to the foregoing specification as indicating the scope of the invention.

We claim:

1. An isolated cryET5 gene having a nucleotide base sequence coding for the amino acid sequence shown in FIG. 2 and listed in SEQ ID NO:4.

2. An isolated cryET5 gene according to claim 1 wherein the gene has a coding region extending from nucleotide bases 67 to 3756 in the nucleotide base sequence shown in FIG. 2 and listed in SEQ ID NO:3.

3. A recombinant plasmid containing the gene of claim 1 or 2.

4. A biologically pure culture of a bacterium transformed with and capable of expressing the recombinant plasmid of claim 3.

5. The bacterium of claim 4 wherein the bacterium is *Bacillus thuringiensis*.

6. The *Bacillus thuringiensis* bacterium of claim 5 deposited with the NRRL having accession number NRRL B-21111 and being designated as strain EG7283, or mutants thereof having insecticidal activity against lepidopteran insects at least equivalent to that of *B.t.* strain EG7283.

7. An insecticide composition comprising the bacterium of claim 4, a lepidopteran-toxic protein produced by such bacterium, and an agriculturally acceptable carrier.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 3713 base pairs
      ( B ) TYPE: nucleic acid
      ( C ) STRANDEDNESS: double
      ( D ) TOPOLOGY: circular ( i i ) MOLECULE TYPE: DNA (genomic)

( i x ) FEATURE:
      ( A ) NAME/KEY: CDS
      ( B ) LOCATION: 99..3602

( x i ) SEQUENCE DESCRIPTION: SEQ ID NO:1:

```
AAATTCATAA  TATGAATCAT  ACGTTTTAAA  GTGTTGTGAA  GAAAAGAGAA  TTGATCTTTA         60

GAATTTTTTT  ATTTTAACCA  AAGAGAAAGG  GGTAACTT  ATG  GAG  ATA  AAT  AAT         113
                                              Met  Glu  Ile  Asn  Asn
                                               1                    5

CAG  AAG  CAA  TGC  ATA  CCA  TAT  AAT  TGC  TTA  AGT  AAT  CCT  GAG  GAA  GTA    161
Gln  Lys  Gln  Cys  Ile  Pro  Tyr  Asn  Cys  Leu  Ser  Asn  Pro  Glu  Glu  Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 10  |     |     |     |     | 15  |     |     |     |     | 20  |     |      |
| CTT | TTG | GAT | GGG | GAG | AGG | ATA | TTA | CCT | GAT | ATC | GAT | CCA | CTC | GAA | GTT | 209  |
| Leu | Leu | Asp | Gly | Glu | Arg | Ile | Leu | Pro | Asp | Ile | Asp | Pro | Leu | Glu | Val |      |
|     |     |     | 25  |     |     |     |     | 30  |     |     |     |     | 35  |     |     |      |
| TCT | TTG | TCG | CTT | TTG | CAA | TTT | CTT | TTG | AAT | AAC | TTT | GTT | CCA | GGG | GGA | 257  |
| Ser | Leu | Ser | Leu | Leu | Gln | Phe | Leu | Leu | Asn | Asn | Phe | Val | Pro | Gly | Gly |      |
|     |     | 40  |     |     |     |     | 45  |     |     |     |     | 50  |     |     |     |      |
| GGC | TTT | ATT | TCA | GGA | TTA | GTT | GAT | AAA | ATA | TGG | GGG | GCT | TTG | AGA | CCA | 305  |
| Gly | Phe | Ile | Ser | Gly | Leu | Val | Asp | Lys | Ile | Trp | Gly | Ala | Leu | Arg | Pro |      |
|     | 55  |     |     |     |     | 60  |     |     |     |     | 65  |     |     |     |     |      |
| TCT | GAA | TGG | GAC | TTA | TTT | CTT | GCA | CAG | ATT | GAA | CGG | TTG | ATT | GAT | CAA | 353  |
| Ser | Glu | Trp | Asp | Leu | Phe | Leu | Ala | Gln | Ile | Glu | Arg | Leu | Ile | Asp | Gln |      |
| 70  |     |     |     |     | 75  |     |     |     |     | 80  |     |     |     |     | 85  |      |
| AGA | ATA | GAA | GCA | ACA | GTA | AGA | GCA | AAA | GCA | ATC | ACT | GAA | TTA | GAA | GGA | 401  |
| Arg | Ile | Glu | Ala | Thr | Val | Arg | Ala | Lys | Ala | Ile | Thr | Glu | Leu | Glu | Gly |      |
|     |     |     |     | 90  |     |     |     |     | 95  |     |     |     |     | 100 |     |      |
| TTA | GGG | AGA | AAT | TAT | CAA | ATA | TAC | GCT | GAA | GCA | TTT | AAA | GAA | TGG | GAA | 449  |
| Leu | Gly | Arg | Asn | Tyr | Gln | Ile | Tyr | Ala | Glu | Ala | Phe | Lys | Glu | Trp | Glu |      |
|     |     |     | 105 |     |     |     |     | 110 |     |     |     |     | 115 |     |     |      |
| TCA | GAT | CCT | GAT | AAC | GAA | GCG | GCT | AAA | AGT | AGA | GTA | ATT | GAT | CGC | TTT | 497  |
| Ser | Asp | Pro | Asp | Asn | Glu | Ala | Ala | Lys | Ser | Arg | Val | Ile | Asp | Arg | Phe |      |
|     |     | 120 |     |     |     |     | 125 |     |     |     |     | 130 |     |     |     |      |
| CGT | ATA | CTT | GAT | GGT | CTA | ATT | GAA | GCA | AAT | ATC | CCT | TCA | TTT | CGG | ATA | 545  |
| Arg | Ile | Leu | Asp | Gly | Leu | Ile | Glu | Ala | Asn | Ile | Pro | Ser | Phe | Arg | Ile |      |
| 135 |     |     |     |     | 140 |     |     |     |     | 145 |     |     |     |     |     |      |
| ATT | GGA | TTT | GAA | GTG | CCA | CTT | TTA | TCG | GTT | TAT | GTT | CAA | GCA | GCT | AAT | 593  |
| Ile | Gly | Phe | Glu | Val | Pro | Leu | Leu | Ser | Val | Tyr | Val | Gln | Ala | Ala | Asn |      |
| 150 |     |     |     |     | 155 |     |     |     |     | 160 |     |     |     |     | 165 |      |
| CTA | CAT | CTC | GCT | CTA | TTG | AGA | GAT | TCT | GTT | ATT | TTT | GGA | GAG | AGA | TGG | 641  |
| Leu | His | Leu | Ala | Leu | Leu | Arg | Asp | Ser | Val | Ile | Phe | Gly | Glu | Arg | Trp |      |
|     |     |     |     | 170 |     |     |     |     | 175 |     |     |     |     | 180 |     |      |
| GGA | TTG | ACG | ACA | AAA | AAT | GTC | AAT | GAT | ATC | TAT | AAT | AGA | CAA | ATT | AGA | 689  |
| Gly | Leu | Thr | Thr | Lys | Asn | Val | Asn | Asp | Ile | Tyr | Asn | Arg | Gln | Ile | Arg |      |
|     |     |     | 185 |     |     |     |     | 190 |     |     |     |     | 195 |     |     |      |
| GAA | ATT | CAT | GAA | TAT | AGC | AAT | CAT | TGC | GTA | GAT | ACG | TAT | AAC | ACA | GAA | 737  |
| Glu | Ile | His | Glu | Tyr | Ser | Asn | His | Cys | Val | Asp | Thr | Tyr | Asn | Thr | Glu |      |
|     |     | 200 |     |     |     |     | 205 |     |     |     |     | 210 |     |     |     |      |
| CTA | GAA | CGT | CTA | GGG | TTT | AGA | TCT | ATA | GCG | CAG | TGG | AGA | ATA | TAT | AAT | 785  |
| Leu | Glu | Arg | Leu | Gly | Phe | Arg | Ser | Ile | Ala | Gln | Trp | Arg | Ile | Tyr | Asn |      |
|     | 215 |     |     |     |     | 220 |     |     |     |     | 225 |     |     |     |     |      |
| CAG | TTT | AGA | AGA | GAA | CTA | ACA | CTA | ACT | GTA | TTA | GAT | ATT | GTC | GCT | CTT | 833  |
| Gln | Phe | Arg | Arg | Glu | Leu | Thr | Leu | Thr | Val | Leu | Asp | Ile | Val | Ala | Leu |      |
| 230 |     |     |     |     | 235 |     |     |     |     | 240 |     |     |     |     | 245 |      |
| TTC | CCG | AAC | TAT | GAC | AGT | AGA | CTG | TAT | CCG | ATC | CAA | ACT | TTT | TCT | CAA | 881  |
| Phe | Pro | Asn | Tyr | Asp | Ser | Arg | Leu | Tyr | Pro | Ile | Gln | Thr | Phe | Ser | Gln |      |
|     |     |     |     | 250 |     |     |     |     | 255 |     |     |     |     | 260 |     |      |
| TTG | ACA | AGA | GAA | ATT | GTT | ACA | TCC | CCA | GTA | AGC | GAA | TTT | TAT | TAT | GGT | 929  |
| Leu | Thr | Arg | Glu | Ile | Val | Thr | Ser | Pro | Val | Ser | Glu | Phe | Tyr | Tyr | Gly |      |
|     |     |     | 265 |     |     |     |     | 270 |     |     |     |     | 275 |     |     |      |
| GTT | ATT | AAT | AGT | GGT | AAT | ATA | ATT | GGT | ACT | CTT | ACT | GAA | CAG | CAG | ATA | 977  |
| Val | Ile | Asn | Ser | Gly | Asn | Ile | Ile | Gly | Thr | Leu | Thr | Glu | Gln | Gln | Ile |      |
|     |     | 280 |     |     |     |     | 285 |     |     |     |     | 290 |     |     |     |      |
| AGG | CGA | CCA | CAT | CTT | ATG | GAC | TTC | TTT | AAC | TCC | ATG | ATC | ATG | TAT | ACA | 1025 |
| Arg | Arg | Pro | His | Leu | Met | Asp | Phe | Phe | Asn | Ser | Met | Ile | Met | Tyr | Thr |      |
|     | 295 |     |     |     |     | 300 |     |     |     |     | 305 |     |     |     |     |      |
| TCA | GAT | AAT | AGA | CGG | GAA | CAT | TAT | TGG | TCA | GGA | CTT | GAA | ATG | ACG | GCT | 1073 |
| Ser | Asp | Asn | Arg | Arg | Glu | His | Tyr | Trp | Ser | Gly | Leu | Glu | Met | Thr | Ala |      |
| 310 |     |     |     |     | 315 |     |     |     |     | 320 |     |     |     |     | 325 |      |
| TAT | TTT | ACA | GGA | TTT | GCA | GGA | GCT | CAA | GTG | TCA | TTC | CCT | TTA | GTC | GGG | 1121 |
| Tyr | Phe | Thr | Gly | Phe | Ala | Gly | Ala | Gln | Val | Ser | Phe | Pro | Leu | Val | Gly |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 330 |     |     |     |     |     | 335 |     |     |     |     | 340 |      |
| ACT | AGA | GGG | GAG | TCA | GCT | CCA | CCA | TTA | ACT | GTT | AGA | AGT | GTT | AAT | GAT | 1169 |
| Thr | Arg | Gly | Glu | Ser | Ala | Pro | Pro | Leu | Thr | Val | Arg | Ser | Val | Asn | Asp |      |
|     |     |     |     | 345 |     |     |     |     |     | 350 |     |     |     |     | 355 |      |
| GGA | ATT | TAT | AGA | ATA | TTA | TCG | GCA | CCG | TTT | TAT | TCA | GCG | CCT | TTT | CTA | 1217 |
| Gly | Ile | Tyr | Arg | Ile | Leu | Ser | Ala | Pro | Phe | Tyr | Ser | Ala | Pro | Phe | Leu |      |
|     |     |     |     | 360 |     |     |     |     |     | 365 |     |     |     |     | 370 |      |
| GGC | ACC | ATT | GTA | TTG | GGA | AGT | CGT | GGA | GAA | AAA | TTT | GAT | TTT | GCG | CTT | 1265 |
| Gly | Thr | Ile | Val | Leu | Gly | Ser | Arg | Gly | Glu | Lys | Phe | Asp | Phe | Ala | Leu |      |
|     |     |     |     | 375 |     |     |     |     |     | 380 |     |     |     |     | 385 |      |
| AAT | AAT | ATT | TCA | CCT | CCG | CCA | TCT | ACA | ATA | TAC | AGA | CAT | CCT | GGA | ACA | 1313 |
| Asn | Asn | Ile | Ser | Pro | Pro | Pro | Ser | Thr | Ile | Tyr | Arg | His | Pro | Gly | Thr |      |
|     |     |     |     | 390 |     |     |     |     |     | 395 |     |     |     |     | 400 |     | 405 |
| GTA | GAT | TCA | CTA | GTC | AGT | ATA | CCG | CCA | CAG | GAT | AAT | AGC | GTA | CCA | CCG | 1361 |
| Val | Asp | Ser | Leu | Val | Ser | Ile | Pro | Pro | Gln | Asp | Asn | Ser | Val | Pro | Pro |      |
|     |     |     |     |     |     | 410 |     |     |     |     |     | 415 |     |     |     | 420 |
| CAC | AGG | GGA | TCT | AGT | CAT | CGA | TTA | AGT | CAT | GTT | ACA | ATG | CGC | GCA | AGT | 1409 |
| His | Arg | Gly | Ser | Ser | His | Arg | Leu | Ser | His | Val | Thr | Met | Arg | Ala | Ser |      |
|     |     |     |     | 425 |     |     |     |     |     | 430 |     |     |     |     | 435 |      |
| TCC | CCT | ATA | TTC | CAT | TGG | ACG | CAT | CGC | AGC | GCA | ACC | ACT | ACA | AAT | ACA | 1457 |
| Ser | Pro | Ile | Phe | His | Trp | Thr | His | Arg | Ser | Ala | Thr | Thr | Thr | Asn | Thr |      |
|     |     |     |     | 440 |     |     |     |     |     | 445 |     |     |     |     | 450 |      |
| ATT | AAT | CCA | AAT | GCT | ATT | ATC | CAA | ATA | CCA | CTA | GTA | AAA | GCA | TTT | AAC | 1505 |
| Ile | Asn | Pro | Asn | Ala | Ile | Ile | Gln | Ile | Pro | Leu | Val | Lys | Ala | Phe | Asn |      |
|     |     |     |     | 455 |     |     |     |     |     | 460 |     |     |     |     | 465 |      |
| CTT | CAT | TCA | GGT | GCC | ACT | GTT | GTT | AGA | GGA | CCA | GGG | TTT | ACA | GGT | GGT | 1553 |
| Leu | His | Ser | Gly | Ala | Thr | Val | Val | Arg | Gly | Pro | Gly | Phe | Thr | Gly | Gly |      |
| 470 |     |     |     |     |     | 475 |     |     |     |     |     | 480 |     |     |     | 485 |
| GAT | ATC | CTT | CGA | AGA | ACG | AAT | ACT | GGC | ACA | TTT | GCA | GAT | ATG | AGA | GTA | 1601 |
| Asp | Ile | Leu | Arg | Arg | Thr | Asn | Thr | Gly | Thr | Phe | Ala | Asp | Met | Arg | Val |      |
|     |     |     |     |     |     | 490 |     |     |     |     |     | 495 |     |     |     | 500 |
| AAT | ATT | ACT | GGG | CCA | TTA | TCC | CAA | AGA | TAT | CGT | GTA | AGA | ATT | CGC | TAT | 1649 |
| Asn | Ile | Thr | Gly | Pro | Leu | Ser | Gln | Arg | Tyr | Arg | Val | Arg | Ile | Arg | Tyr |      |
|     |     |     |     | 505 |     |     |     |     |     | 510 |     |     |     |     | 515 |      |
| GCT | TCT | ACG | ACA | GAT | TTA | CAA | TTT | TTC | ACG | AGA | ATC | AAT | GGA | ACT | TCT | 1697 |
| Ala | Ser | Thr | Thr | Asp | Leu | Gln | Phe | Phe | Thr | Arg | Ile | Asn | Gly | Thr | Ser |      |
|     |     |     |     | 520 |     |     |     |     |     | 525 |     |     |     |     | 530 |      |
| GTA | AAT | CAA | GGT | AAT | TTC | CAA | AGA | ACT | ATG | AAT | AGA | GGG | GAT | AAT | TTA | 1745 |
| Val | Asn | Gln | Gly | Asn | Phe | Gln | Arg | Thr | Met | Asn | Arg | Gly | Asp | Asn | Leu |      |
|     |     |     |     | 535 |     |     |     |     |     | 540 |     |     |     |     | 545 |      |
| GAA | TCT | GGA | AAC | TTT | AGG | ACT | GCA | GGA | TTT | AGT | ACG | CCT | TTT | AGT | TTT | 1793 |
| Glu | Ser | Gly | Asn | Phe | Arg | Thr | Ala | Gly | Phe | Ser | Thr | Pro | Phe | Ser | Phe |      |
| 550 |     |     |     |     |     | 555 |     |     |     |     |     | 560 |     |     |     | 565 |
| TCA | AAT | GCG | CAA | AGT | ACA | TTC | ACA | TTG | GGT | ACT | CAG | GCT | TTT | TCA | AAT | 1841 |
| Ser | Asn | Ala | Gln | Ser | Thr | Phe | Thr | Leu | Gly | Thr | Gln | Ala | Phe | Ser | Asn |      |
|     |     |     |     | 570 |     |     |     |     |     | 575 |     |     |     |     | 580 |      |
| CAG | GAA | GTT | TAT | ATA | GAT | CGA | ATT | GAA | TTT | GTC | CCG | GCA | GAA | GTA | ACA | 1889 |
| Gln | Glu | Val | Tyr | Ile | Asp | Arg | Ile | Glu | Phe | Val | Pro | Ala | Glu | Val | Thr |      |
|     |     |     |     | 585 |     |     |     |     |     | 590 |     |     |     |     | 595 |      |
| TTC | GAG | GCA | GAA | TCT | GAT | TTA | GAA | AGA | GCG | CAA | AAG | GCG | GTG | AAT | GCC | 1937 |
| Phe | Glu | Ala | Glu | Ser | Asp | Leu | Glu | Arg | Ala | Gln | Lys | Ala | Val | Asn | Ala |      |
|     |     |     |     |     |     | 600 |     |     |     |     |     | 605 |     |     |     | 610 |
| CTG | TTT | ACT | TCT | ACA | AAC | CAA | CTA | GGG | CTA | AAA | ACA | GAT | GTG | ACG | GAT | 1985 |
| Leu | Phe | Thr | Ser | Thr | Asn | Gln | Leu | Gly | Leu | Lys | Thr | Asp | Val | Thr | Asp |      |
|     |     |     |     | 615 |     |     |     |     |     | 620 |     |     |     |     | 625 |      |
| TAT | CAG | ATT | GAT | CAA | GTG | TCC | AAT | TTA | GTA | GAA | TGT | TTA | TCA | GAT | GAA | 2033 |
| Tyr | Gln | Ile | Asp | Gln | Val | Ser | Asn | Leu | Val | Glu | Cys | Leu | Ser | Asp | Glu |      |
| 630 |     |     |     |     |     | 635 |     |     |     |     |     | 640 |     |     |     | 645 |
| TTT | TGT | CTG | GAT | GAA | AAG | AGA | GAA | TTG | TCC | GAG | AAA | GTC | AAA | CAT | GCA | 2081 |
| Phe | Cys | Leu | Asp | Glu | Lys | Arg | Glu | Leu | Ser | Glu | Lys | Val | Lys | His | Ala |      |

| | | | | | | | | | | | | | | | | |
|---|---|---|---|---|---|---|---|---|---|---|---|---|---|---|---|---|
| AAG | CGA | CTT | AGT | GAT | AAG | CGG | AAC | CTA | CTT | CAA | GAT | CCA | AAC | TTC | ACA | 2129 |
| Lys | Arg | Leu | Ser | Asp | Lys | Arg | Asn | Leu | Leu | Gln | Asp | Pro | Asn | Phe | Thr | |
| | | | 665 | | | | 670 | | | | | 675 | | | | |
| TCT | ATC | AAT | AGA | CAA | CTA | GAC | CGT | GGA | TGG | AGA | GGA | AGT | ACG | GAT | ATT | 2177 |
| Ser | Ile | Asn | Arg | Gln | Leu | Asp | Arg | Gly | Trp | Arg | Gly | Ser | Thr | Asp | Ile | |
| | | 680 | | | | | 685 | | | | | 690 | | | | |
| ACC | ATC | CAA | GGA | GGA | AAT | GAC | GTA | TTC | AAA | GAG | AAT | TAC | GTC | ACA | CTA | 2225 |
| Thr | Ile | Gln | Gly | Gly | Asn | Asp | Val | Phe | Lys | Glu | Asn | Tyr | Val | Thr | Leu | |
| | 695 | | | | | 700 | | | | | 705 | | | | | |
| CCA | GGT | ACC | TTT | GAT | GAG | TGT | TAT | CCA | ACG | TAT | TTG | TAT | CAA | AAA | ATA | 2273 |
| Pro | Gly | Thr | Phe | Asp | Glu | Cys | Tyr | Pro | Thr | Tyr | Leu | Tyr | Gln | Lys | Ile | |
| 710 | | | | | 715 | | | | | 720 | | | | | 725 | |
| GAT | GAG | TCA | AAA | TTA | AAA | GCC | TAT | ACT | CGC | TAT | GAA | TTA | AGA | GGG | TAT | 2321 |
| Asp | Glu | Ser | Lys | Leu | Lys | Ala | Tyr | Thr | Arg | Tyr | Glu | Leu | Arg | Gly | Tyr | |
| | | | | 730 | | | | | 735 | | | | | 740 | | |
| ATT | GAA | GAT | AGT | CAA | GAT | TTA | GAA | GTC | TAT | TTG | ATT | CGT | TAC | AAT | GCG | 2369 |
| Ile | Glu | Asp | Ser | Gln | Asp | Leu | Glu | Val | Tyr | Leu | Ile | Arg | Tyr | Asn | Ala | |
| | | | 745 | | | | | 750 | | | | | 755 | | | |
| AAA | CAT | GAA | ACA | GTA | AAT | GTT | CCC | GGT | ACA | GGG | TCC | TTA | TGG | CCG | CTT | 2417 |
| Lys | His | Glu | Thr | Val | Asn | Val | Pro | Gly | Thr | Gly | Ser | Leu | Trp | Pro | Leu | |
| | | 760 | | | | | 765 | | | | | 770 | | | | |
| TCA | GTC | GAA | AGC | CCA | ATC | GGA | AGG | TGC | GGA | GAA | CCG | AAT | CGA | TGT | GTG | 2465 |
| Ser | Val | Glu | Ser | Pro | Ile | Gly | Arg | Cys | Gly | Glu | Pro | Asn | Arg | Cys | Val | |
| | 775 | | | | | 780 | | | | | 785 | | | | | |
| CCA | CAT | ATT | GAA | TGG | AAT | CCT | GAT | TTA | GAT | TGT | TCG | TGT | AGG | GAT | GGG | 2513 |
| Pro | His | Ile | Glu | Trp | Asn | Pro | Asp | Leu | Asp | Cys | Ser | Cys | Arg | Asp | Gly | |
| 790 | | | | | 795 | | | | | 800 | | | | | 805 | |
| GAG | AAG | TGT | GCC | CAT | CAT | TCG | CAT | CAT | TTC | TCT | CTA | GAT | ATT | GAT | GTT | 2561 |
| Glu | Lys | Cys | Ala | His | His | Ser | His | His | Phe | Ser | Leu | Asp | Ile | Asp | Val | |
| | | | | 810 | | | | | 815 | | | | | 820 | | |
| GGA | TGT | ACA | GAC | CTA | AAT | GAG | GAC | CTA | GGT | GTA | TGG | GTG | ATC | TTT | AAG | 2609 |
| Gly | Cys | Thr | Asp | Leu | Asn | Glu | Asp | Leu | Gly | Val | Trp | Val | Ile | Phe | Lys | |
| | | | 825 | | | | | 830 | | | | | 835 | | | |
| ATT | AAA | ACG | CAG | GAT | GGC | CAT | GCA | AGA | TTA | GGA | AAT | CTA | GAG | TTT | CTC | 2657 |
| Ile | Lys | Thr | Gln | Asp | Gly | His | Ala | Arg | Leu | Gly | Asn | Leu | Glu | Phe | Leu | |
| | | 840 | | | | | 845 | | | | | 850 | | | | |
| GAA | GAG | AAA | CCA | TTG | TTA | GGA | GAA | GCG | TTA | GCT | CGT | GTG | AAA | AGA | GCG | 2705 |
| Glu | Glu | Lys | Pro | Leu | Leu | Gly | Glu | Ala | Leu | Ala | Arg | Val | Lys | Arg | Ala | |
| | 855 | | | | | 860 | | | | | 865 | | | | | |
| GAG | AAA | AAA | TGG | AGA | GAC | AAA | CGC | GAA | CAA | TTG | CAG | TTT | GAA | ACG | AAT | 2753 |
| Glu | Lys | Lys | Trp | Arg | Asp | Lys | Arg | Glu | Gln | Leu | Gln | Phe | Glu | Thr | Asn | |
| 870 | | | | | 875 | | | | | 880 | | | | | 885 | |
| ATC | GTT | TAC | AAA | GAG | GCA | AAA | GAA | TCT | GTA | GAT | GCT | TTA | TTC | GTA | GAT | 2801 |
| Ile | Val | Tyr | Lys | Glu | Ala | Lys | Glu | Ser | Val | Asp | Ala | Leu | Phe | Val | Asp | |
| | | | | 890 | | | | | 895 | | | | | 900 | | |
| TCT | CAC | TAT | AAT | AGA | TTA | CAA | GCG | GAT | ACG | AAC | ATT | ACG | ATG | ATT | CAT | 2849 |
| Ser | His | Tyr | Asn | Arg | Leu | Gln | Ala | Asp | Thr | Asn | Ile | Thr | Met | Ile | His | |
| | | | 905 | | | | | 910 | | | | | 915 | | | |
| GCG | GCA | GAT | AAA | CGC | GTT | CAT | CGA | ATC | CGA | GAG | GCT | TAT | CTT | CCG | GAA | 2897 |
| Ala | Ala | Asp | Lys | Arg | Val | His | Arg | Ile | Arg | Glu | Ala | Tyr | Leu | Pro | Glu | |
| | | 920 | | | | | 925 | | | | | 930 | | | | |
| TTA | TCC | GTT | ATC | CCA | GGT | GTA | AAT | GCG | GAC | ATT | TTT | GAA | GAA | TTA | GAA | 2945 |
| Leu | Ser | Val | Ile | Pro | Gly | Val | Asn | Ala | Asp | Ile | Phe | Glu | Glu | Leu | Glu | |
| | 935 | | | | | 940 | | | | | 945 | | | | | |
| GGT | CTT | ATT | TTC | ACT | GCA | TTC | TCC | CTA | TAT | GAT | GCG | AGA | AAT | ATC | ATT | 2993 |
| Gly | Leu | Ile | Phe | Thr | Ala | Phe | Ser | Leu | Tyr | Asp | Ala | Arg | Asn | Ile | Ile | |
| 950 | | | | | 955 | | | | | 960 | | | | | 965 | |
| AAA | AAC | GGT | GAT | TTC | AAT | AAT | GGT | TTA | TCG | TGT | TGG | AAC | GTG | AAA | GGG | 3041 |
| Lys | Asn | Gly | Asp | Phe | Asn | Asn | Gly | Leu | Ser | Cys | Trp | Asn | Val | Lys | Gly | |

|  |  |  |  |  |  |  |  |  |  |  |  |  |  |  |  |  |
|---|---|---|---|---|---|---|---|---|---|---|---|---|---|---|---|---|
|  |  |  |  |  | 970 |  |  |  |  | 975 |  |  |  |  | 980 |  |
| CAT | GTA | GAT | ATA | CAA | CAG | AAT | GAT | CAT | CGT | TCT | GTC | CTC | GTT | GTC | CCG | 3089 |
| His | Val | Asp | Ile | Gln | Gln | Asn | Asp | His | Arg | Ser | Val | Leu | Val | Val | Pro |  |
|  |  |  | 985 |  |  |  |  | 990 |  |  |  |  | 995 |  |  |  |
| GAA | TGG | GAA | TCA | GAG | GTA | TCA | CAA | GAA | GTC | CGC | GTA | TGT | CCA | GGT | CGT | 3137 |
| Glu | Trp | Glu | Ser | Glu | Val | Ser | Gln | Glu | Val | Arg | Val | Cys | Pro | Gly | Arg |  |
|  |  |  | 1000 |  |  |  |  | 1005 |  |  |  |  | 1010 |  |  |  |
| GGC | TAT | ATT | CTT | CGT | GTC | ACA | GCG | TAC | AAA | GAG | GGC | TAC | GGA | GAA | GGA | 3185 |
| Gly | Tyr | Ile | Leu | Arg | Val | Thr | Ala | Tyr | Lys | Glu | Gly | Tyr | Gly | Glu | Gly |  |
|  |  |  | 1015 |  |  |  |  | 1020 |  |  |  |  | 1025 |  |  |  |
| TGC | GTA | ACG | ATC | CAT | GAG | ATC | GAA | GAC | AAT | ACA | GAC | GAA | TTG | AAG | TTT | 3233 |
| Cys | Val | Thr | Ile | His | Glu | Ile | Glu | Asp | Asn | Thr | Asp | Glu | Leu | Lys | Phe |  |
| 1030 |  |  |  |  | 1035 |  |  |  |  | 1040 |  |  |  |  | 1045 |  |
| AGT | AAC | TGC | ATA | GAA | GAG | GAA | GTC | TAT | CCA | ACG | GAT | ACA | GGT | AAT | GAT | 3281 |
| Ser | Asn | Cys | Ile | Glu | Glu | Glu | Val | Tyr | Pro | Thr | Asp | Thr | Gly | Asn | Asp |  |
|  |  |  |  | 1050 |  |  |  |  | 1055 |  |  |  |  | 1060 |  |  |
| TAT | ACT | GCA | CAC | CAA | GGT | ACA | ACA | GGA | TGC | GCA | GAT | GCA | TGT | AAT | TCC | 3329 |
| Tyr | Thr | Ala | His | Gln | Gly | Thr | Thr | Gly | Cys | Ala | Asp | Ala | Cys | Asn | Ser |  |
|  |  |  | 1065 |  |  |  |  | 1070 |  |  |  |  | 1075 |  |  |  |
| CGT | AAT | GTT | GGA | TAT | GAG | GAT | GGA | TAT | GAA | ATA | AAT | ACT | ACA | GCA | TCT | 3377 |
| Arg | Asn | Val | Gly | Tyr | Glu | Asp | Gly | Tyr | Glu | Ile | Asn | Thr | Thr | Ala | Ser |  |
|  |  |  | 1080 |  |  |  |  | 1085 |  |  |  |  | 1090 |  |  |  |
| GTT | AAT | TAC | AAA | CCG | ACT | TAT | GAA | GAA | GAA | ATG | TAT | ACA | GAT | GTA | CGA | 3425 |
| Val | Asn | Tyr | Lys | Pro | Thr | Tyr | Glu | Glu | Glu | Met | Tyr | Thr | Asp | Val | Arg |  |
|  | 1095 |  |  |  |  | 1100 |  |  |  |  | 1105 |  |  |  |  |  |
| AGA | GAT | AAT | CAT | TGT | GAA | TAT | GAC | AGA | GGA | TAT | GGG | AAC | CAT | ACA | CCG | 3473 |
| Arg | Asp | Asn | His | Cys | Glu | Tyr | Asp | Arg | Gly | Tyr | Gly | Asn | His | Thr | Pro |  |
| 1110 |  |  |  |  | 1115 |  |  |  |  | 1120 |  |  |  |  | 1125 |  |
| TTA | CCA | GCT | GGT | TAT | GTA | ACA | AAA | GAA | TTA | GAG | TAC | TTC | CCT | GAA | ACA | 3521 |
| Leu | Pro | Ala | Gly | Tyr | Val | Thr | Lys | Glu | Leu | Glu | Tyr | Phe | Pro | Glu | Thr |  |
|  |  |  | 1130 |  |  |  |  | 1135 |  |  |  |  | 1140 |  |  |  |
| GAT | ACA | GTA | TGG | ATA | GAG | ATT | GGA | GAA | ACG | GAA | GGA | ACA | TTC | ATC | GTA | 3569 |
| Asp | Thr | Val | Trp | Ile | Glu | Ile | Gly | Glu | Thr | Glu | Gly | Thr | Phe | Ile | Val |  |
|  |  |  | 1145 |  |  |  |  | 1150 |  |  |  |  | 1155 |  |  |  |
| GAT | AGT | GTG | GAA | TTA | CTC | CTC | ATG | GAG | GAA | TAAGATTGTA | CGAAATCGAC |  |  |  |  | 3619 |
| Asp | Ser | Val | Glu | Leu | Leu | Leu | Met | Glu | Glu |  |  |  |  |  |  |  |
|  |  |  | 1160 |  |  |  | 1165 |  |  |  |  |  |  |  |  |  |

TTTAAATGGC TCATTCTAAA CAAAAAGTAG TCGTCTAATC TCTGTAACAA ATAGAAAAGT 3679

AAATATTTGT AGAAAAAAGA AAAAGGACAT TACT 3713

( 2 ) INFORMATION FOR SEQ ID NO:2:

( i ) SEQUENCE CHARACTERISTICS:
        ( A ) LENGTH: 1167 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Ile | Asn | Asn | Gln | Lys | Gln | Cys | Ile | Pro | Tyr | Asn | Cys | Leu | Ser |
|---|---|---|---|---|---|---|---|---|---|---|---|---|---|---|---|
| 1 |  |  |  | 5 |  |  |  |  | 10 |  |  |  |  | 15 |  |
| Asn | Pro | Glu | Glu | Val | Leu | Leu | Asp | Gly | Glu | Arg | Ile | Leu | Pro | Asp | Ile |
|  |  |  | 20 |  |  |  |  | 25 |  |  |  |  | 30 |  |  |
| Asp | Pro | Leu | Glu | Val | Ser | Leu | Ser | Leu | Leu | Gln | Phe | Leu | Leu | Asn | Asn |
|  |  |  | 35 |  |  |  |  | 40 |  |  |  |  | 45 |  |  |
| Phe | Val | Pro | Gly | Gly | Gly | Phe | Ile | Ser | Gly | Leu | Val | Asp | Lys | Ile | Trp |
|  |  | 50 |  |  |  |  | 55 |  |  |  |  | 60 |  |  |  |
| Gly | Ala | Leu | Arg | Pro | Ser | Glu | Trp | Asp | Leu | Phe | Leu | Ala | Gln | Ile | Glu |
| 65 |  |  |  |  | 70 |  |  |  |  | 75 |  |  |  |  | 80 |

```
Arg  Leu  Ile  Asp  Gln  Arg  Ile  Glu  Ala  Thr  Val  Arg  Ala  Lys  Ala  Ile
               85                      90                     95

Thr  Glu  Leu  Glu  Gly  Leu  Gly  Arg  Asn  Tyr  Gln  Ile  Tyr  Ala  Glu  Ala
               100                     105                    110

Phe  Lys  Glu  Trp  Glu  Ser  Asp  Pro  Asp  Asn  Glu  Ala  Ala  Lys  Ser  Arg
               115                     120                    125

Val  Ile  Asp  Arg  Phe  Arg  Ile  Leu  Asp  Gly  Leu  Ile  Glu  Ala  Asn  Ile
          130                     135                    140

Pro  Ser  Phe  Arg  Ile  Ile  Gly  Phe  Glu  Val  Pro  Leu  Leu  Ser  Val  Tyr
145                          150                     155                     160

Val  Gln  Ala  Ala  Asn  Leu  His  Leu  Ala  Leu  Leu  Arg  Asp  Ser  Val  Ile
                    165                     170                    175

Phe  Gly  Glu  Arg  Trp  Gly  Leu  Thr  Thr  Lys  Asn  Val  Asn  Asp  Ile  Tyr
               180                     185                    190

Asn  Arg  Gln  Ile  Arg  Glu  Ile  His  Glu  Tyr  Ser  Asn  His  Cys  Val  Asp
          195                     200                    205

Thr  Tyr  Asn  Thr  Glu  Leu  Glu  Arg  Leu  Gly  Phe  Arg  Ser  Ile  Ala  Gln
     210                     215                    220

Trp  Arg  Ile  Tyr  Asn  Gln  Phe  Arg  Arg  Glu  Leu  Thr  Leu  Thr  Val  Leu
225                           230                    235                     240

Asp  Ile  Val  Ala  Leu  Phe  Pro  Asn  Tyr  Asp  Ser  Arg  Leu  Tyr  Pro  Ile
               245                     250                    255

Gln  Thr  Phe  Ser  Gln  Leu  Thr  Arg  Glu  Ile  Val  Thr  Ser  Pro  Val  Ser
               260                     265                    270

Glu  Phe  Tyr  Tyr  Gly  Val  Ile  Asn  Ser  Gly  Asn  Ile  Ile  Gly  Thr  Leu
          275                     280                    285

Thr  Glu  Gln  Gln  Ile  Arg  Arg  Pro  His  Leu  Met  Asp  Phe  Phe  Asn  Ser
     290                     295                    300

Met  Ile  Met  Tyr  Thr  Ser  Asp  Asn  Arg  Arg  Glu  His  Tyr  Trp  Ser  Gly
305                           310                    315                     320

Leu  Glu  Met  Thr  Ala  Tyr  Phe  Thr  Gly  Phe  Ala  Gly  Ala  Gln  Val  Ser
               325                     330                    335

Phe  Pro  Leu  Val  Gly  Thr  Arg  Gly  Glu  Ser  Ala  Pro  Pro  Leu  Thr  Val
               340                     345                    350

Arg  Ser  Val  Asn  Asp  Gly  Ile  Tyr  Arg  Ile  Leu  Ser  Ala  Pro  Phe  Tyr
          355                     360                    365

Ser  Ala  Pro  Phe  Leu  Gly  Thr  Ile  Val  Leu  Gly  Ser  Arg  Gly  Glu  Lys
     370                     375                    380

Phe  Asp  Phe  Ala  Leu  Asn  Asn  Ile  Ser  Pro  Pro  Pro  Ser  Thr  Ile  Tyr
385                           390                    395                     400

Arg  His  Pro  Gly  Thr  Val  Asp  Ser  Leu  Val  Ser  Ile  Pro  Pro  Gln  Asp
               405                     410                    415

Asn  Ser  Val  Pro  Pro  His  Arg  Gly  Ser  Ser  His  Arg  Leu  Ser  His  Val
               420                     425                    430

Thr  Met  Arg  Ala  Ser  Ser  Pro  Ile  Phe  His  Trp  Thr  His  Arg  Ser  Ala
          435                     440                    445

Thr  Thr  Thr  Asn  Thr  Ile  Asn  Pro  Asn  Ala  Ile  Ile  Gln  Ile  Pro  Leu
     450                     455                    460

Val  Lys  Ala  Phe  Asn  Leu  His  Ser  Gly  Ala  Thr  Val  Val  Arg  Gly  Pro
465                           470                    475                     480

Gly  Phe  Thr  Gly  Gly  Asp  Ile  Leu  Arg  Arg  Thr  Asn  Thr  Gly  Thr  Phe
               485                     490                    495

Ala  Asp  Met  Arg  Val  Asn  Ile  Thr  Gly  Pro  Leu  Ser  Gln  Arg  Tyr  Arg
```

|     |     |     | 500 |     |     |     | 505 |     |     |     | 510 |     |     |
| --- | --- | --- | --- | --- | --- | --- | --- | --- | --- | --- | --- | --- | --- |
| Val | Arg | Ile | Arg | Tyr | Ala | Ser | Thr | Thr | Asp | Leu | Gln | Phe | Phe | Thr | Arg |
|     |     | 515 |     |     |     | 520 |     |     |     | 525 |     |     |

```
Val Arg Ile Arg Tyr Ala Ser Thr Thr Asp Leu Gln Phe Phe Thr Arg
            515             520             525

Ile Asn Gly Thr Ser Val Asn Gln Gly Asn Phe Gln Arg Thr Met Asn
    530             535             540

Arg Gly Asp Asn Leu Glu Ser Gly Asn Phe Arg Thr Ala Gly Phe Ser
545             550             555                         560

Thr Pro Phe Ser Phe Ser Asn Ala Gln Ser Thr Phe Thr Leu Gly Thr
            565             570             575

Gln Ala Phe Ser Asn Gln Glu Val Tyr Ile Asp Arg Ile Glu Phe Val
            580             585                 590

Pro Ala Glu Val Thr Phe Glu Ala Glu Ser Asp Leu Glu Arg Ala Gln
        595             600             605

Lys Ala Val Asn Ala Leu Phe Thr Ser Thr Asn Gln Leu Gly Leu Lys
        610             615             620

Thr Asp Val Thr Asp Tyr Gln Ile Asp Gln Val Ser Asn Leu Val Glu
625             630             635                         640

Cys Leu Ser Asp Glu Phe Cys Leu Asp Glu Lys Arg Glu Leu Ser Glu
                645             650             655

Lys Val Lys His Ala Lys Arg Leu Ser Asp Lys Arg Asn Leu Leu Gln
            660             665             670

Asp Pro Asn Phe Thr Ser Ile Asn Arg Gln Leu Asp Arg Gly Trp Arg
        675             680             685

Gly Ser Thr Asp Ile Thr Ile Gln Gly Gly Asn Asp Val Phe Lys Glu
        690             695             700

Asn Tyr Val Thr Leu Pro Gly Thr Phe Asp Glu Cys Tyr Pro Thr Tyr
705             710             715                         720

Leu Tyr Gln Lys Ile Asp Glu Ser Lys Leu Lys Ala Tyr Thr Arg Tyr
                725             730             735

Glu Leu Arg Gly Tyr Ile Glu Asp Ser Gln Asp Leu Glu Val Tyr Leu
            740             745             750

Ile Arg Tyr Asn Ala Lys His Glu Thr Val Asn Val Pro Gly Thr Gly
        755             760             765

Ser Leu Trp Pro Leu Ser Val Glu Ser Pro Ile Gly Arg Cys Gly Glu
770             775             780

Pro Asn Arg Cys Val Pro His Ile Glu Trp Asn Pro Asp Leu Asp Cys
785             790             795                         800

Ser Cys Arg Asp Gly Glu Lys Cys Ala His His Ser His His Phe Ser
            805             810             815

Leu Asp Ile Asp Val Gly Cys Thr Asp Leu Asn Glu Asp Leu Gly Val
            820             825             830

Trp Val Ile Phe Lys Ile Lys Thr Gln Asp Gly His Ala Arg Leu Gly
        835             840             845

Asn Leu Glu Phe Leu Glu Glu Lys Pro Leu Leu Gly Glu Ala Leu Ala
850             855             860

Arg Val Lys Arg Ala Glu Lys Lys Trp Arg Asp Lys Arg Glu Gln Leu
865             870             875             880

Gln Phe Glu Thr Asn Ile Val Tyr Lys Glu Ala Lys Glu Ser Val Asp
            885             890             895

Ala Leu Phe Val Asp Ser His Tyr Asn Arg Leu Gln Ala Asp Thr Asn
            900             905             910

Ile Thr Met Ile His Ala Ala Asp Lys Arg Val His Arg Ile Arg Glu
        915             920             925
```

```
Ala Tyr Leu Pro Glu Leu Ser Val Ile Pro Gly Val Asn Ala Asp Ile
    930                 935                 940

Phe Glu Glu Leu Glu Gly Leu Ile Phe Thr Ala Phe Ser Leu Tyr Asp
945                 950                 955                 960

Ala Arg Asn Ile Ile Lys Asn Gly Asp Phe Asn Asn Gly Leu Ser Cys
                965                 970                 975

Trp Asn Val Lys Gly His Val Asp Ile Gln Gln Asn Asp His Arg Ser
            980                 985                 990

Val Leu Val Val Pro Glu Trp Glu Ser Glu Val Ser Gln Glu Val Arg
        995                 1000                1005

Val Cys Pro Gly Arg Gly Tyr Ile Leu Arg Val Thr Ala Tyr Lys Glu
    1010                1015                1020

Gly Tyr Gly Glu Gly Cys Val Thr Ile His Glu Ile Glu Asp Asn Thr
1025                1030                1035                1040

Asp Glu Leu Lys Phe Ser Asn Cys Ile Glu Glu Val Tyr Pro Thr
                1045                1050                1055

Asp Thr Gly Asn Asp Tyr Thr Ala His Gln Gly Thr Thr Gly Cys Ala
            1060                1065                1070

Asp Ala Cys Asn Ser Arg Asn Val Gly Tyr Glu Asp Gly Tyr Glu Ile
        1075                1080                1085

Asn Thr Thr Ala Ser Val Asn Tyr Lys Pro Thr Tyr Glu Glu Glu Met
    1090                1095                1100

Tyr Thr Asp Val Arg Arg Asp Asn His Cys Glu Tyr Asp Arg Gly Tyr
1105                1110                1115                1120

Gly Asn His Thr Pro Leu Pro Ala Gly Tyr Val Thr Lys Glu Leu Glu
                1125                1130                1135

Tyr Phe Pro Glu Thr Asp Thr Val Trp Ile Glu Ile Gly Glu Thr Glu
            1140                1145                1150

Gly Thr Phe Ile Val Asp Ser Val Glu Leu Leu Leu Met Glu Glu
        1155                1160                1165
```

( 2 ) INFORMATION FOR SEQ ID NO:3:

( i ) SEQUENCE CHARACTERISTICS:
        ( A ) LENGTH: 3934 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 67..3756

( i x ) FEATURE:
        ( A ) NAME/KEY: misc_feature
        ( B ) LOCATION: 2253..2272

( x i ) SEQUENCE DESCRIPTION: SEQ ID NO:3:

```
AAACTATTCA ATGGAGAAAA ATTGAATAGT TGTAATGTAA GCACACCGAA AAAAGGAGGA        60

GTTATA TTG ACT TCA AAT AGG AAA AAT GAG AAT GAA ATT ATA AAT GCT          108
       Leu Thr Ser Asn Arg Lys Asn Glu Asn Glu Ile Ile Asn Ala
         1               5                   10

TTA TCG ATT CCA ACG GTA TCG AAT CCT TCC ACG CAA ATG AAT CTA TCA         156
Leu Ser Ile Pro Thr Val Ser Asn Pro Ser Thr Gln Met Asn Leu Ser
 15              20                  25                  30

CCA GAT GCT CGT ATT GAA GAT AGC TTG TGT GTA GCC GAG GTG AAC AAT         204
Pro Asp Ala Arg Ile Glu Asp Ser Leu Cys Val Ala Glu Val Asn Asn
             35                  40                  45
```

| | | | | | | | | | | | | | | | | |
|---|---|---|---|---|---|---|---|---|---|---|---|---|---|---|---|---|
| ATT | GAT | CCA | TTT | GTT | AGC | GCA | TCA | ACA | GTC | CAA | ACG | GGT | ATA | AAC | ATA | 252 |
| Ile | Asp | Pro | Phe | Val | Ser | Ala | Ser | Thr | Val | Gln | Thr | Gly | Ile | Asn | Ile | |
| | | | 50 | | | | 55 | | | | | 60 | | | | |
| GCT | GGT | AGA | ATA | TTG | GGC | GTA | TTA | GGT | GTG | CCG | TTT | GCT | GGA | CAA | CTA | 300 |
| Ala | Gly | Arg | Ile | Leu | Gly | Val | Leu | Gly | Val | Pro | Phe | Ala | Gly | Gln | Leu | |
| | | 65 | | | | | 70 | | | | | 75 | | | | |
| GCT | AGT | TTT | TAT | AGT | TTT | CTT | GTT | GGG | GAA | TTA | TGG | CCT | AGT | GGC | AGA | 348 |
| Ala | Ser | Phe | Tyr | Ser | Phe | Leu | Val | Gly | Glu | Leu | Trp | Pro | Ser | Gly | Arg | |
| | 80 | | | | | 85 | | | | | 90 | | | | | |
| GAT | CCA | TGG | GAA | ATT | TTC | CTG | GAA | CAT | GTA | GAA | CAA | CTT | ATA | AGA | CAA | 396 |
| Asp | Pro | Trp | Glu | Ile | Phe | Leu | Glu | His | Val | Glu | Gln | Leu | Ile | Arg | Gln | |
| 95 | | | | | 100 | | | | | 105 | | | | | 110 | |
| CAA | GTA | ACA | GAA | AAT | ACT | AGG | AAT | ACG | GCT | ATT | GCT | CGA | TTA | GAA | GGT | 444 |
| Gln | Val | Thr | Glu | Asn | Thr | Arg | Asn | Thr | Ala | Ile | Ala | Arg | Leu | Glu | Gly | |
| | | | | 115 | | | | 120 | | | | | 125 | | | |
| CTA | GGA | AGA | GGC | TAT | AGA | TCT | TAC | CAG | CAG | GCT | CTT | GAA | ACT | TGG | TTA | 492 |
| Leu | Gly | Arg | Gly | Tyr | Arg | Ser | Tyr | Gln | Gln | Ala | Leu | Glu | Thr | Trp | Leu | |
| | | | 130 | | | | | 135 | | | | | 140 | | | |
| GAT | AAC | CGA | AAT | GAT | GCA | AGA | TCA | AGA | AGC | ATT | ATT | CTT | GAG | CGC | TAT | 540 |
| Asp | Asn | Arg | Asn | Asp | Ala | Arg | Ser | Arg | Ser | Ile | Ile | Leu | Glu | Arg | Tyr | |
| | | 145 | | | | | 150 | | | | | 155 | | | | |
| GTT | GCT | TTA | GAA | CTT | GAC | ATT | ACT | ACT | GCT | ATA | CCG | CTT | TTC | AGA | ATA | 588 |
| Val | Ala | Leu | Glu | Leu | Asp | Ile | Thr | Thr | Ala | Ile | Pro | Leu | Phe | Arg | Ile | |
| | 160 | | | | | 165 | | | | | 170 | | | | | |
| CGA | AAT | GAA | GAA | GTT | CCA | TTA | TTA | ATG | GTA | TAT | GCT | CAA | GCT | GCA | AAT | 636 |
| Arg | Asn | Glu | Glu | Val | Pro | Leu | Leu | Met | Val | Tyr | Ala | Gln | Ala | Ala | Asn | |
| 175 | | | | | 180 | | | | | 185 | | | | | 190 | |
| TTA | CAC | CTA | TTA | TTA | TTG | AGA | GAC | GCA | TCC | CTT | TTT | GGT | AGT | GAA | TGG | 684 |
| Leu | His | Leu | Leu | Leu | Leu | Arg | Asp | Ala | Ser | Leu | Phe | Gly | Ser | Glu | Trp | |
| | | | | 195 | | | | 200 | | | | | 205 | | | |
| GGG | ATG | GCA | TCT | TCC | GAT | GTT | AAC | CAA | TAT | TAC | CAA | GAA | CAA | ATC | AGA | 732 |
| Gly | Met | Ala | Ser | Ser | Asp | Val | Asn | Gln | Tyr | Tyr | Gln | Glu | Gln | Ile | Arg | |
| | | | 210 | | | | | 215 | | | | | 220 | | | |
| TAT | ACA | GAG | GAA | TAT | TCT | AAC | CAT | TGC | GTA | CAA | TGG | TAT | AAT | ACA | GGG | 780 |
| Tyr | Thr | Glu | Glu | Tyr | Ser | Asn | His | Cys | Val | Gln | Trp | Tyr | Asn | Thr | Gly | |
| | | 225 | | | | | 230 | | | | | 235 | | | | |
| CTA | AAT | AAC | TTA | AGA | GGG | ACA | AAT | GCT | GAA | AGT | TGG | TTG | CGG | TAT | AAT | 828 |
| Leu | Asn | Asn | Leu | Arg | Gly | Thr | Asn | Ala | Glu | Ser | Trp | Leu | Arg | Tyr | Asn | |
| | 240 | | | | | 245 | | | | | 250 | | | | | |
| CAA | TTC | CGT | AGA | GAC | CTA | ACG | TTA | GGG | GTA | TTA | GAT | TTA | GTA | GCC | CTA | 876 |
| Gln | Phe | Arg | Arg | Asp | Leu | Thr | Leu | Gly | Val | Leu | Asp | Leu | Val | Ala | Leu | |
| 255 | | | | | 260 | | | | | 265 | | | | | 270 | |
| TTC | CCA | AGC | TAT | GAT | ACT | CGC | ACT | TAT | CCA | ATC | AAT | ACG | AGT | GCT | CAG | 924 |
| Phe | Pro | Ser | Tyr | Asp | Thr | Arg | Thr | Tyr | Pro | Ile | Asn | Thr | Ser | Ala | Gln | |
| | | | | 275 | | | | 280 | | | | | 285 | | | |
| TTA | ACA | AGA | GAA | ATT | TAT | ACA | GAT | CCA | ATT | GGG | AGA | ACA | AAT | GCA | CCT | 972 |
| Leu | Thr | Arg | Glu | Ile | Tyr | Thr | Asp | Pro | Ile | Gly | Arg | Thr | Asn | Ala | Pro | |
| | | | 290 | | | | | 295 | | | | | 300 | | | |
| TCA | GGA | TTT | GCA | AGT | ACG | AAT | TGG | TTT | AAT | AAT | AAT | GCA | CCA | TCG | TTT | 1020 |
| Ser | Gly | Phe | Ala | Ser | Thr | Asn | Trp | Phe | Asn | Asn | Asn | Ala | Pro | Ser | Phe | |
| | | 305 | | | | | 310 | | | | | 315 | | | | |
| TCT | GCC | ATA | GAG | GCT | GCC | ATT | TTC | AGG | CCT | CCG | CAT | CTA | CTT | GAT | TTT | 1068 |
| Ser | Ala | Ile | Glu | Ala | Ala | Ile | Phe | Arg | Pro | Pro | His | Leu | Leu | Asp | Phe | |
| | 320 | | | | | 325 | | | | | 330 | | | | | |
| CCA | GAA | CAA | CTT | ACA | ATT | TAC | AGT | GCA | TCA | AGC | CGT | TGG | AGT | AGC | ACT | 1116 |
| Pro | Glu | Gln | Leu | Thr | Ile | Tyr | Ser | Ala | Ser | Ser | Arg | Trp | Ser | Ser | Thr | |
| 335 | | | | | 340 | | | | | 345 | | | | | 350 | |
| CAA | CAT | ATG | AAT | TAT | TGG | GTG | GGA | CAT | AGG | CTT | AAC | TTC | CGC | CCA | ATA | 1164 |
| Gln | His | Met | Asn | Tyr | Trp | Val | Gly | His | Arg | Leu | Asn | Phe | Arg | Pro | Ile | |
| | | | | 355 | | | | | 360 | | | | | 365 | | |

| | | | | | | | | | | | | | | | | |
|---|---|---|---|---|---|---|---|---|---|---|---|---|---|---|---|---|
| GGA | GGG | ACA | TTA | AAT | ACC | TCA | ACA | CAA | GGA | CTT | ACT | AAT | AAT | ACT | TCA | 1212 |
| Gly | Gly | Thr | Leu 370 | Asn | Thr | Ser | Thr | Gln 375 | Gly | Leu | Thr | Asn | Asn 380 | Thr | Ser | |
| ATT | AAT | CCT | GTA | ACA | TTA | CAG | TTT | ACG | TCT | CGA | GAC | GTT | TAT | AGA | ACA | 1260 |
| Ile | Asn | Pro 385 | Val | Thr | Leu | Gln | Phe 390 | Thr | Ser | Arg | Asp | Val 395 | Tyr | Arg | Thr | |
| GAA | TCA | AAT | GCA | GGG | ACA | AAT | ATA | CTA | TTT | ACT | ACT | CCT | GTG | AAT | GGA | 1308 |
| Glu | Ser 400 | Asn | Ala | Gly | Thr | Asn 405 | Ile | Leu | Phe | Thr | Thr 410 | Pro | Val | Asn | Gly | |
| GTA | CCT | TGG | GCT | AGA | TTT | AAT | TTT | ATA | AAC | CCT | CAG | AAT | ATT | TAT | GAA | 1356 |
| Val 415 | Pro | Trp | Ala | Arg | Phe 420 | Asn | Phe | Ile | Asn | Pro 425 | Gln | Asn | Ile | Tyr | Glu 430 | |
| AGA | GGC | GCC | ACT | ACC | TAC | AGT | CAA | CCG | TAT | CAG | GGA | GTT | GGG | ATT | CAA | 1404 |
| Arg | Gly | Ala | Thr | Thr 435 | Tyr | Ser | Gln | Pro | Tyr 440 | Gln | Gly | Val | Gly | Ile 445 | Gln | |
| TTA | TTT | GAT | TCA | GAA | ACT | GAA | TTA | CCA | CCA | GAA | ACA | ACA | GAA | CGA | CCA | 1452 |
| Leu | Phe | Asp | Ser 450 | Glu | Thr | Glu | Leu | Pro 455 | Pro | Glu | Thr | Thr 460 | Glu | Arg | Pro | |
| AAT | TAT | GAA | TCA | TAT | AGT | CAT | AGA | TTA | TCT | CAT | ATA | GGA | CTA | ATC | ATA | 1500 |
| Asn | Tyr | Glu 465 | Ser | Tyr | Ser | His | Arg 470 | Leu | Ser | His | Ile | Gly 475 | Leu | Ile | Ile | |
| GGA | AAC | ACT | TTG | AGA | GCA | CCA | GTC | TAT | TCT | TGG | ACG | CAT | CGT | AGT | GCA | 1548 |
| Gly | Asn 480 | Thr | Leu | Arg | Ala | Pro 485 | Val | Tyr | Ser | Trp | Thr 490 | His | Arg | Ser | Ala | |
| GAT | CGT | ACG | AAT | ACG | ATT | GGA | CCA | AAT | AGA | ATT | ACA | CAA | ATA | CCA | TTG | 1596 |
| Asp 495 | Arg | Thr | Asn | Thr | Ile 500 | Gly | Pro | Asn | Arg | Ile 505 | Thr | Gln | Ile | Pro | Leu 510 | |
| GTA | AAA | GCA | CTG | AAT | CTT | CAT | TCA | GGT | GTT | ACT | GTT | GTT | GGA | GGG | CCA | 1644 |
| Val | Lys | Ala | Leu | Asn 515 | Leu | His | Ser | Gly | Val 520 | Thr | Val | Val | Gly | Gly 525 | Pro | |
| GGA | TTT | ACA | GGT | GGG | GAT | ATC | CTT | CGT | AGA | ACA | AAT | ACG | GGT | ACA | TTT | 1692 |
| Gly | Phe | Thr | Gly 530 | Gly | Asp | Ile | Leu | Arg 535 | Arg | Thr | Asn | Thr 540 | Gly | Thr | Phe | |
| GGA | GAT | ATA | CGA | TTA | AAT | ATT | AAT | GTG | CCA | TTA | TCC | CAA | AGA | TAT | CGC | 1740 |
| Gly | Asp | Ile | Arg 545 | Leu | Asn | Ile | Asn | Val 550 | Pro | Leu | Ser | Gln | Arg 555 | Tyr | Arg | |
| GTA | AGG | ATT | CGT | TAT | GCT | TCT | ACT | ACA | GAT | TTA | CAA | TTT | TTC | ACG | AGA | 1788 |
| Val | Arg 560 | Ile | Arg | Tyr | Ala | Ser 565 | Thr | Thr | Asp | Leu | Gln 570 | Phe | Phe | Thr | Arg | |
| ATT | AAT | GGA | ACC | ACT | GTT | AAT | ATT | GGT | AAT | TTC | TCA | AGA | ACT | ATG | AAT | 1836 |
| Ile | Asn | Gly | Thr | Thr 580 | Val | Asn | Ile | Gly | Asn 585 | Phe | Ser | Arg | Thr | Met 590 | Asn | |
| | | | | | | | | | | | | | | | | |
| Ile 575 | | | | | | | | | | | | | | | | |
| AGG | GGG | GAT | AAT | TTA | GAA | TAT | AGA | AGT | TTT | AGA | ACT | GCA | GGA | TTT | AGT | 1884 |
| Arg | Gly | Asp | Asn | Leu 595 | Glu | Tyr | Arg | Ser | Phe 600 | Arg | Thr | Ala | Gly | Phe 605 | Ser | |
| ACT | CCT | TTT | AAT | TTT | TTA | AAT | GCC | CAA | AGC | ACA | TTC | ACA | TTG | GGT | GCT | 1932 |
| Thr | Pro | Phe | Asn 610 | Phe | Leu | Asn | Ala | Gln 615 | Ser | Thr | Phe | Thr 620 | Leu | Gly | Ala | |
| CAG | AGT | TTT | TCA | AAT | CAG | GAA | GTT | TAT | ATA | GAT | AGA | GTC | GAA | TTT | GTT | 1980 |
| Gln | Ser | Phe | Ser 625 | Asn | Gln | Glu | Val | Tyr 630 | Ile | Asp | Arg | Val 635 | Glu | Phe | Val | |
| CCA | GCA | GAG | GTA | ACA | TTT | GAG | GCA | GAA | TAT | GAT | TTA | GAA | AGA | GCA | CAA | 2028 |
| Pro | Ala | Glu 640 | Val | Thr | Phe | Glu | Ala 645 | Glu | Tyr | Asp | Leu 650 | Glu | Arg | Ala | Gln | |
| AAG | GCG | GTG | AAT | GCT | CTG | TTT | ACT | TCT | ACA | AAT | CCA | AGA | AGA | TTG | AAA | 2076 |
| Lys 655 | Ala | Val | Asn | Ala | Leu 660 | Phe | Thr | Ser | Thr | Asn 665 | Pro | Arg | Arg | Leu | Lys 670 | |
| ACA | GAT | GTG | ACA | GAT | TAT | CAT | ATT | GAC | CAA | GTG | TCC | AAT | ATG | GTG | GCA | 2124 |
| Thr | Asp | Val | Thr | Asp 675 | Tyr | His | Ile | Asp | Gln 680 | Val | Ser | Asn | Met | Val 685 | Ala | |

| | | | | | | | | | | | | | | | | |
|---|---|---|---|---|---|---|---|---|---|---|---|---|---|---|---|---|
| TGT | TTA | TCA | GAT | GAA | TTT | TGC | TTG | GAT | GAG | AAG | CGA | GAA | TTA | TTT | GAG | 2172 |
| Cys | Leu | Ser | Asp<br>690 | Glu | Phe | Cys | Leu | Asp<br>695 | Glu | Lys | Arg | Glu | Leu<br>700 | Phe | Glu | |
| AAA | GTG | AAA | TAT | GCG | AAG | CGA | CTC | AGT | GAT | GAA | AGA | AAC | TTA | CTC | CAA | 2220 |
| Lys | Val | Lys<br>705 | Tyr | Ala | Lys | Arg | Leu<br>710 | Ser | Asp | Glu | Arg | Asn<br>715 | Leu | Leu | Gln | |
| GAT | CCA | AAC | TTC | ACA | TTC | ATC | AGT | GGG | CAA | TTA | AGT | TTC | GCA | TCC | ATC | 2268 |
| Asp | Pro | Asn<br>720 | Phe | Thr | Phe | Ile | Ser<br>725 | Gly | Gln | Leu | Ser | Phe<br>730 | Ala | Ser | Ile | |
| GAT | GGA | CAA | TCA | AAC | TTC | CCC | TCT | ATT | AAT | GAG | CTA | TCT | GAA | CAT | GGA | 2316 |
| Asp<br>735 | Gly | Gln | Ser | Asn | Phe<br>740 | Pro | Ser | Ile | Asn | Glu<br>745 | Leu | Ser | Glu | His | Gly<br>750 | |
| TGG | TGG | GGA | AGT | GCG | AAT | GTT | ACC | ATT | CAG | GAA | GGG | AAT | GAC | GTA | TTT | 2364 |
| Trp | Trp | Gly | Ser | Ala<br>755 | Asn | Val | Thr | Ile | Gln<br>760 | Glu | Gly | Asn | Asp | Val<br>765 | Phe | |
| AAA | GAG | AAT | TAC | GTC | ACA | CTA | CCG | GGT | ACT | TTT | AAT | GAG | TGT | TAT | CCA | 2412 |
| Lys | Glu | Asn | Tyr<br>770 | Val | Thr | Leu | Pro | Gly<br>775 | Thr | Phe | Asn | Glu | Cys<br>780 | Tyr | Pro | |
| AAT | TAT | TTA | TAT | CAA | AAA | ATA | GGA | GAG | TCA | GAA | TTA | AAA | GCT | TAT | ACG | 2460 |
| Asn | Tyr | Leu<br>785 | Tyr | Gln | Lys | Ile | Gly<br>790 | Glu | Ser | Glu | Leu | Lys<br>795 | Ala | Tyr | Thr | |
| CGC | TAT | CAA | TTA | AGA | GGG | TAT | ATT | GAA | GAT | AGT | CAA | GAT | CTA | GAG | ATT | 2508 |
| Arg | Tyr<br>800 | Gln | Leu | Arg | Gly | Tyr<br>805 | Ile | Glu | Asp | Ser | Gln<br>810 | Asp | Leu | Glu | Ile | |
| TAT | TTA | ATT | CGT | TAC | AAT | GCA | AAG | CAT | GAA | ACA | TTG | GAT | GTT | CCA | GGT | 2556 |
| Tyr<br>815 | Leu | Ile | Arg | Tyr | Asn<br>820 | Ala | Lys | His | Glu | Thr<br>825 | Leu | Asp | Val | Pro | Gly<br>830 | |
| ACC | GAT | TCC | CTA | TGG | CCG | CTT | TCA | GTT | GAA | AGC | CCA | ATC | GGA | AGG | TGC | 2604 |
| Thr | Asp | Ser | Leu | Trp<br>835 | Pro | Leu | Ser | Val | Glu<br>840 | Ser | Pro | Ile | Gly | Arg<br>845 | Cys | |
| GGA | GAA | CCA | AAT | CGA | TGC | GCA | CCA | CAT | TTT | GAA | TGG | AAT | CCT | GAT | CTA | 2652 |
| Gly | Glu | Pro | Asn | Arg<br>850 | Cys | Ala | Pro | His | Phe<br>855 | Glu | Trp | Asn | Pro | Asp<br>860 | Leu | |
| GAT | TGT | TCC | TGC | AGA | GAT | GGA | GAA | AGA | TGT | GCG | CAT | CAT | TCC | CAT | CAT | 2700 |
| Asp | Cys | Ser<br>865 | Cys | Arg | Asp | Gly | Glu<br>870 | Arg | Cys | Ala | His | His<br>875 | Ser | His | His | |
| TTC | ACT | TTG | GAT | ATT | GAT | GTT | GGG | TGC | ACA | GAC | TTG | CAT | GAG | AAC | CTA | 2748 |
| Phe | Thr | Leu<br>880 | Asp | Ile | Asp | Val | Gly<br>885 | Cys | Thr | Asp | Leu | His<br>890 | Glu | Asn | Leu | |
| GGC | GTG | TGG | GTG | GTA | TTC | AAG | ATT | AAG | ACG | CAG | GAA | GGT | TAT | GCA | AGA | 2796 |
| Gly | Val<br>895 | Trp | Val | Val | Phe<br>900 | Lys | Ile | Lys | Thr | Gln<br>905 | Glu | Gly | Tyr | Ala | Arg<br>910 | |
| TTA | GGA | AAT | CTG | GAA | TTT | ATC | GAA | GAG | AAA | CCA | TTA | ATT | GGA | GAA | GCA | 2844 |
| Leu | Gly | Asn | Leu | Glu<br>915 | Phe | Ile | Glu | Glu | Lys<br>920 | Pro | Leu | Ile | Gly | Glu<br>925 | Ala | |
| CTG | TCT | CGT | GTG | AAG | AGA | GCG | GAA | AAA | AAA | TGG | AGA | GAC | AAA | CGG | GAA | 2892 |
| Leu | Ser | Arg<br>930 | Val | Lys | Arg | Ala | Glu<br>935 | Lys | Lys | Trp | Arg | Asp<br>940 | Lys | Arg | Glu | |
| AAA | CTA | CAA | TTG | GAA | ACA | AAA | CGA | GTA | TAT | ACA | GAG | GCA | AAA | GAA | GCT | 2940 |
| Lys | Leu | Gln<br>945 | Leu | Glu | Thr | Lys | Arg<br>950 | Val | Tyr | Thr | Glu | Ala<br>955 | Lys | Glu | Ala | |
| GTG | GAT | GCT | TTA | TTC | GTA | GAT | TCT | CAA | TAT | GAT | CAA | TTA | CAA | GCG | GAT | 2988 |
| Val | Asp | Ala<br>960 | Leu | Phe | Val | Asp | Ser<br>965 | Gln | Tyr | Asp | Gln | Leu<br>970 | Gln | Ala | Asp | |
| ACA | AAC | ATT | GGC | ATG | ATT | CAT | GCG | GCA | GAT | AAA | CTT | GTT | CAT | CGA | ATT | 3036 |
| Thr | Asn | Ile<br>975 | Gly | Met | Ile | His<br>980 | Ala | Ala | Asp | Lys | Leu<br>985 | Val | His | Arg | Ile<br>990 | |
| CGA | GAG | GCG | TAT | CTT | TCA | GAA | TTA | CCT | GTT | ATC | CCA | GGT | GTA | AAT | GCG | 3084 |
| Arg | Glu | Ala | Tyr<br>995 | Leu | Ser | Glu | Leu | Pro<br>1000 | Val | Ile | Pro | Gly | Val<br>1005 | Asn | Ala | |

| | | | | | | | | | | | | | | | | |
|---|---|---|---|---|---|---|---|---|---|---|---|---|---|---|---|---|
| GAA | ATT | TTT | GAA | GAA | TTA | GAA | GGT | CAC | ATT | ATC | ACT | GCA | ATG | TCC | TTA | 3132 |
| Glu | Ile | Phe | Glu | Glu | Leu | Glu | Gly | His | Ile | Ile | Thr | Ala | Met | Ser | Leu | |
| | | | 1010 | | | | | 1015 | | | | | 1020 | | | |
| TAC | GAT | GCG | AGA | AAT | GTC | GTT | AAA | AAT | GGT | GAT | TTT | AAT | AAT | GGA | TTA | 3180 |
| Tyr | Asp | Ala | Arg | Asn | Val | Val | Lys | Asn | Gly | Asp | Phe | Asn | Asn | Gly | Leu | |
| | | | 1025 | | | | 1030 | | | | | 1035 | | | | |
| ACA | TGT | TGG | AAT | GTA | AAA | GGG | CAT | GTA | GAT | GTA | CAA | CAG | AGC | CAT | CAT | 3228 |
| Thr | Cys | Trp | Asn | Val | Lys | Gly | His | Val | Asp | Val | Gln | Gln | Ser | His | His | |
| | 1040 | | | | | 1045 | | | | | 1050 | | | | | |
| CGT | TCT | GAC | CTT | GTT | ATC | CCA | GAA | TGG | GAA | GCA | GAA | GTG | TCA | CAA | GCA | 3276 |
| Arg | Ser | Asp | Leu | Val | Ile | Pro | Glu | Trp | Glu | Ala | Glu | Val | Ser | Gln | Ala | |
| 1055 | | | | | 1060 | | | | | 1065 | | | | | 1070 | |
| GTT | CGC | GTC | TGT | CCG | GGG | CGT | GGC | TAT | ATC | CTT | CGT | GTC | ACA | GCG | TAC | 3324 |
| Val | Arg | Val | Cys | Pro | Gly | Arg | Gly | Tyr | Ile | Leu | Arg | Val | Thr | Ala | Tyr | |
| | | | | 1075 | | | | | 1080 | | | | | 1085 | | |
| AAA | GAG | GGA | TAT | GGA | GAG | GGC | TGC | GTA | ACG | ATC | CAT | GAA | ATC | GAG | AAC | 3372 |
| Lys | Glu | Gly | Tyr | Gly | Glu | Gly | Cys | Val | Thr | Ile | His | Glu | Ile | Glu | Asn | |
| | | | 1090 | | | | | 1095 | | | | | 1100 | | | |
| AAT | ACA | GAC | GAA | CTA | AAA | TTT | AAA | AAC | TGT | GAA | GAA | GAG | GAA | GTG | TAT | 3420 |
| Asn | Thr | Asp | Glu | Leu | Lys | Phe | Lys | Asn | Cys | Glu | Glu | Glu | Glu | Val | Tyr | |
| | | | 1105 | | | | 1110 | | | | | 1115 | | | | |
| CCA | ACG | GAT | ACA | GGA | ACG | TGT | AAT | GAT | TAT | ACT | GCA | CAC | CAA | GGT | ACA | 3468 |
| Pro | Thr | Asp | Thr | Gly | Thr | Cys | Asn | Asp | Tyr | Thr | Ala | His | Gln | Gly | Thr | |
| | | 1120 | | | | | 1125 | | | | | 1130 | | | | |
| GCA | GCA | TGT | AAT | TCC | CGT | AAT | GCT | GGA | TAT | GAG | GAT | GCA | TAT | GAA | GTT | 3516 |
| Ala | Ala | Cys | Asn | Ser | Arg | Asn | Ala | Gly | Tyr | Glu | Asp | Ala | Tyr | Glu | Val | |
| 1135 | | | | | 1140 | | | | | 1145 | | | | | 1150 | |
| GAT | ACT | ACA | GCA | TCT | GTT | AAT | TAC | AAA | CCG | ACT | TAT | GAA | GAA | GAA | ACG | 3564 |
| Asp | Thr | Thr | Ala | Ser | Val | Asn | Tyr | Lys | Pro | Thr | Tyr | Glu | Glu | Glu | Thr | |
| | | | | 1155 | | | | | 1160 | | | | | 1165 | | |
| TAT | ACA | GAT | GTA | CGA | AGA | GAT | AAT | CAT | TGT | GAA | TAT | GAC | AGA | GGG | TAT | 3612 |
| Tyr | Thr | Asp | Val | Arg | Arg | Asp | Asn | His | Cys | Glu | Tyr | Asp | Arg | Gly | Tyr | |
| | | | 1170 | | | | | 1175 | | | | | 1180 | | | |
| GTG | AAT | TAT | CCA | CCA | GTA | CCA | GCT | GGT | TAT | GTG | ACA | AAA | GAA | TTA | GAA | 3660 |
| Val | Asn | Tyr | Pro | Pro | Val | Pro | Ala | Gly | Tyr | Val | Thr | Lys | Glu | Leu | Glu | |
| | | | 1185 | | | | | 1190 | | | | | 1195 | | | |
| TAC | TTC | CCA | GAA | ACA | GAT | ACA | GTA | TGG | ATT | GAG | ATT | GGA | GAA | ACG | GAA | 3708 |
| Tyr | Phe | Pro | Glu | Thr | Asp | Thr | Val | Trp | Ile | Glu | Ile | Gly | Glu | Thr | Glu | |
| | | | 1200 | | | | | 1205 | | | | | 1210 | | | |
| GGA | AAG | TTT | ATT | GTA | GAT | AGC | GTG | GAA | CTA | CTC | CTC | ATG | GAA | GAA | TAGGATCA | 3763 |
| Gly | Lys | Phe | Ile | Val | Asp | Ser | Val | Glu | Leu | Leu | Leu | Met | Glu | Glu | | |
| 1215 | | | | | 1220 | | | | | 1225 | | | | | 123 | |
| CAAGTATAGC | AGTTTAATAA | ATATTAATTA | AAATAGTAGT | CTAACTTCCG | TTCCAATTAA | | | | | | | | | | | 3823 |
| ATAAGTAAAT | TACAGTTGTA | AAAAGAAAAC | GGACATCACT | CTTCAGAGAG | CGATGTCCGT | | | | | | | | | | | 3883 |
| TTTTTATATG | GTGTGTGCTA | ATGATAAATG | TGCACGAAAT | TATATTGTCA | A | | | | | | | | | | | 3934 |

( 2 ) INFORMATION FOR SEQ ID NO:4:

( i ) SEQUENCE CHARACTERISTICS:
        ( A ) LENGTH: 1229 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Leu | Thr | Ser | Asn | Arg | Lys | Asn | Glu | Asn | Glu | Ile | Ile | Asn | Ala | Leu | Ser |
| 1 | | | | 5 | | | | | 10 | | | | | 15 | |
| Ile | Pro | Thr | Val | Ser | Asn | Pro | Ser | Thr | Gln | Met | Asn | Leu | Ser | Pro | Asp |
| | | | 20 | | | | | 25 | | | | | 30 | | |

| | | | | | | | | | | | | | | |
|---|---|---|---|---|---|---|---|---|---|---|---|---|---|---|
|Ala|Arg|Ile|Glu|Asp|Ser|Leu|Cys|Val|Ala|Glu|Val|Asn|Asn|Ile|Asp|
| | |35| | | |40| | | |45| | | | |
|Pro|Phe|Val|Ser|Ala|Ser|Thr|Val|Gln|Thr|Gly|Ile|Asn|Ile|Ala|Gly|
| |50| | | |55| | | |60| | | | | |
|Arg|Ile|Leu|Gly|Val|Leu|Gly|Val|Pro|Phe|Ala|Gly|Gln|Leu|Ala|Ser|
|65| | | |70| | | |75| | | | | |80|
|Phe|Tyr|Ser|Phe|Leu|Val|Gly|Glu|Leu|Trp|Pro|Ser|Gly|Arg|Asp|Pro|
| | | |85| | | |90| | | | |95| | |
|Trp|Glu|Ile|Phe|Leu|Glu|His|Val|Glu|Gln|Leu|Ile|Arg|Gln|Gln|Val|
| | |100| | | |105| | | |110| | | | |
|Thr|Glu|Asn|Thr|Arg|Asn|Thr|Ala|Ile|Ala|Arg|Leu|Glu|Gly|Leu|Gly|
| |115| | | |120| | | |125| | | | | |
|Arg|Gly|Tyr|Arg|Ser|Tyr|Gln|Gln|Ala|Leu|Glu|Thr|Trp|Leu|Asp|Asn|
| |130| | | |135| | | |140| | | | | |
|Arg|Asn|Asp|Ala|Arg|Ser|Arg|Ser|Ile|Ile|Leu|Glu|Arg|Tyr|Val|Ala|
|145| | | |150| | | |155| | | | | |160|
|Leu|Glu|Leu|Asp|Ile|Thr|Thr|Ala|Ile|Pro|Leu|Phe|Arg|Ile|Arg|Asn|
| | | |165| | | |170| | | | |175| | |
|Glu|Glu|Val|Pro|Leu|Leu|Met|Val|Tyr|Ala|Gln|Ala|Ala|Asn|Leu|His|
| | |180| | | |185| | | |190| | | | |
|Leu|Leu|Leu|Leu|Arg|Asp|Ala|Ser|Leu|Phe|Gly|Ser|Glu|Trp|Gly|Met|
| | |195| | | |200| | | |205| | | | |
|Ala|Ser|Ser|Asp|Val|Asn|Gln|Tyr|Tyr|Gln|Glu|Gln|Ile|Arg|Tyr|Thr|
|210| | | |215| | | |220| | | | | | |
|Glu|Glu|Tyr|Ser|Asn|His|Cys|Val|Gln|Trp|Tyr|Asn|Thr|Gly|Leu|Asn|
|225| | | |230| | | |235| | | | | | 240|
|Asn|Leu|Arg|Gly|Thr|Asn|Ala|Glu|Ser|Trp|Leu|Arg|Tyr|Asn|Gln|Phe|
| | | |245| | | |250| | | | |255| | |
|Arg|Arg|Asp|Leu|Thr|Leu|Gly|Val|Leu|Asp|Leu|Val|Ala|Leu|Phe|Pro|
| | |260| | | |265| | | |270| | | | |
|Ser|Tyr|Asp|Thr|Arg|Thr|Tyr|Pro|Ile|Asn|Thr|Ser|Ala|Gln|Leu|Thr|
| |275| | | |280| | | |285| | | | | |
|Arg|Glu|Ile|Tyr|Thr|Asp|Pro|Ile|Gly|Arg|Thr|Asn|Ala|Pro|Ser|Gly|
| |290| | | |295| | | |300| | | | | |
|Phe|Ala|Ser|Thr|Asn|Trp|Phe|Asn|Asn|Asn|Ala|Pro|Ser|Phe|Ser|Ala|
|305| | | |310| | | |315| | | | | |320|
|Ile|Glu|Ala|Ala|Ile|Phe|Arg|Pro|Pro|His|Leu|Leu|Asp|Phe|Pro|Glu|
| | | |325| | | |330| | | | |335| | |
|Gln|Leu|Thr|Ile|Tyr|Ser|Ala|Ser|Ser|Arg|Trp|Ser|Ser|Thr|Gln|His|
| | |340| | | |345| | | |350| | | | |
|Met|Asn|Tyr|Trp|Val|Gly|His|Arg|Leu|Asn|Phe|Arg|Pro|Ile|Gly|Gly|
| |355| | | |360| | | |365| | | | | |
|Thr|Leu|Asn|Thr|Ser|Thr|Gln|Gly|Leu|Thr|Asn|Asn|Thr|Ser|Ile|Asn|
|370| | | |375| | | |380| | | | | | |
|Pro|Val|Thr|Leu|Gln|Phe|Thr|Ser|Arg|Asp|Val|Tyr|Arg|Thr|Glu|Ser|
|385| | | |390| | | |395| | | | | |400|
|Asn|Ala|Gly|Thr|Asn|Ile|Leu|Phe|Thr|Thr|Pro|Val|Asn|Gly|Val|Pro|
| | | |405| | | |410| | | | |415| | |
|Trp|Ala|Arg|Phe|Asn|Phe|Ile|Asn|Pro|Gln|Asn|Ile|Tyr|Glu|Arg|Gly|
| | |420| | | |425| | | |430| | | | |
|Ala|Thr|Thr|Tyr|Ser|Gln|Pro|Tyr|Gln|Gly|Val|Gly|Ile|Gln|Leu|Phe|
| |435| | | |440| | | |445| | | | | |
|Asp|Ser|Glu|Thr|Glu|Leu|Pro|Pro|Glu|Thr|Thr|Glu|Arg|Pro|Asn|Tyr|
|450| | | |455| | | |460| | | | | | |

-continued

| | | | | | | | | | | | | | | | |
|---|---|---|---|---|---|---|---|---|---|---|---|---|---|---|---|
| Glu | Ser | Tyr | Ser | His | Arg | Leu | Ser | His | Ile | Gly | Leu | Ile | Ile | Gly | Asn |
| 465 | | | | 470 | | | | | 475 | | | | | | 480 |
| Thr | Leu | Arg | Ala | Pro | Val | Tyr | Ser | Trp | Thr | His | Arg | Ser | Ala | Asp | Arg |
| | | | | 485 | | | | | 490 | | | | | 495 | |
| Thr | Asn | Thr | Ile | Gly | Pro | Asn | Arg | Ile | Thr | Gln | Ile | Pro | Leu | Val | Lys |
| | | | 500 | | | | | 505 | | | | | 510 | | |
| Ala | Leu | Asn | Leu | His | Ser | Gly | Val | Thr | Val | Val | Gly | Gly | Pro | Gly | Phe |
| | | | 515 | | | | | 520 | | | | | 525 | | |
| Thr | Gly | Gly | Asp | Ile | Leu | Arg | Arg | Thr | Asn | Thr | Gly | Thr | Phe | Gly | Asp |
| | | 530 | | | | | 535 | | | | | 540 | | | |
| Ile | Arg | Leu | Asn | Ile | Asn | Val | Pro | Leu | Ser | Gln | Arg | Tyr | Arg | Val | Arg |
| 545 | | | | | 550 | | | | | 555 | | | | | 560 |
| Ile | Arg | Tyr | Ala | Ser | Thr | Thr | Asp | Leu | Gln | Phe | Phe | Thr | Arg | Ile | Asn |
| | | | | 565 | | | | | 570 | | | | | 575 | |
| Gly | Thr | Thr | Val | Asn | Ile | Gly | Asn | Phe | Ser | Arg | Thr | Met | Asn | Arg | Gly |
| | | | 580 | | | | | 585 | | | | | 590 | | |
| Asp | Asn | Leu | Glu | Tyr | Arg | Ser | Phe | Arg | Thr | Ala | Gly | Phe | Ser | Thr | Pro |
| | | 595 | | | | | 600 | | | | | 605 | | | |
| Phe | Asn | Phe | Leu | Asn | Ala | Gln | Ser | Thr | Phe | Thr | Leu | Gly | Ala | Gln | Ser |
| 610 | | | | | 615 | | | | | 620 | | | | | |
| Phe | Ser | Asn | Gln | Glu | Val | Tyr | Ile | Asp | Arg | Val | Glu | Phe | Val | Pro | Ala |
| 625 | | | | | 630 | | | | | 635 | | | | | 640 |
| Glu | Val | Thr | Phe | Glu | Ala | Glu | Tyr | Asp | Leu | Glu | Arg | Ala | Gln | Lys | Ala |
| | | | | 645 | | | | | 650 | | | | | 655 | |
| Val | Asn | Ala | Leu | Phe | Thr | Ser | Thr | Asn | Pro | Arg | Arg | Leu | Lys | Thr | Asp |
| | | | 660 | | | | | 665 | | | | | 670 | | |
| Val | Thr | Asp | Tyr | His | Ile | Asp | Gln | Val | Ser | Asn | Met | Val | Ala | Cys | Leu |
| | | 675 | | | | | 680 | | | | | 685 | | | |
| Ser | Asp | Glu | Phe | Cys | Leu | Asp | Glu | Lys | Arg | Glu | Leu | Phe | Glu | Lys | Val |
| | 690 | | | | | 695 | | | | | 700 | | | | |
| Lys | Tyr | Ala | Lys | Arg | Leu | Ser | Asp | Glu | Arg | Asn | Leu | Leu | Gln | Asp | Pro |
| 705 | | | | | 710 | | | | | 715 | | | | | 720 |
| Asn | Phe | Thr | Phe | Ile | Ser | Gly | Gln | Leu | Ser | Phe | Ala | Ser | Ile | Asp | Gly |
| | | | | 725 | | | | | 730 | | | | | 735 | |
| Gln | Ser | Asn | Phe | Pro | Ser | Ile | Asn | Glu | Leu | Ser | Glu | His | Gly | Trp | Trp |
| | | | 740 | | | | | 745 | | | | | 750 | | |
| Gly | Ser | Ala | Asn | Val | Thr | Ile | Gln | Glu | Gly | Asn | Asp | Val | Phe | Lys | Glu |
| | | 755 | | | | | 760 | | | | | 765 | | | |
| Asn | Tyr | Val | Thr | Leu | Pro | Gly | Thr | Phe | Asn | Glu | Cys | Tyr | Pro | Asn | Tyr |
| 770 | | | | | 775 | | | | | 780 | | | | | |
| Leu | Tyr | Gln | Lys | Ile | Gly | Glu | Ser | Glu | Leu | Lys | Ala | Tyr | Thr | Arg | Tyr |
| 785 | | | | | 790 | | | | | 795 | | | | | 800 |
| Gln | Leu | Arg | Gly | Tyr | Ile | Glu | Asp | Ser | Gln | Asp | Leu | Glu | Ile | Tyr | Leu |
| | | | | 805 | | | | | 810 | | | | | 815 | |
| Ile | Arg | Tyr | Asn | Ala | Lys | His | Glu | Thr | Leu | Asp | Val | Pro | Gly | Thr | Asp |
| | | | 820 | | | | | 825 | | | | | 830 | | |
| Ser | Leu | Trp | Pro | Leu | Ser | Val | Glu | Ser | Pro | Ile | Gly | Arg | Cys | Gly | Glu |
| | | | 835 | | | | | 840 | | | | | 845 | | |
| Pro | Asn | Arg | Cys | Ala | Pro | His | Phe | Glu | Trp | Asn | Pro | Asp | Leu | Asp | Cys |
| | 850 | | | | | 855 | | | | | 860 | | | | |
| Ser | Cys | Arg | Asp | Gly | Glu | Arg | Cys | Ala | His | His | Ser | His | His | Phe | Thr |
| 865 | | | | | 870 | | | | | 875 | | | | | 880 |
| Leu | Asp | Ile | Asp | Val | Gly | Cys | Thr | Asp | Leu | His | Glu | Asn | Leu | Gly | Val |

|        |        |        |        | 885    |        |        |        | 890    |        |        |        | 895    |        |        |
|--------|--------|--------|--------|--------|--------|--------|--------|--------|--------|--------|--------|--------|--------|--------|

Trp Val Val Phe Lys Ile Lys Thr Gln Glu Gly Tyr Ala Arg Leu Gly
            900                 905                 910

Asn Leu Glu Phe Ile Glu Glu Lys Pro Leu Ile Gly Glu Ala Leu Ser
            915                 920                 925

Arg Val Lys Arg Ala Glu Lys Lys Trp Arg Asp Lys Arg Glu Lys Leu
    930                 935                 940

Gln Leu Glu Thr Lys Arg Val Tyr Thr Glu Ala Lys Glu Ala Val Asp
945                 950                 955                 960

Ala Leu Phe Val Asp Ser Gln Tyr Asp Gln Leu Gln Ala Asp Thr Asn
            965                 970                 975

Ile Gly Met Ile His Ala Ala Asp Lys Leu Val His Arg Ile Arg Glu
            980                 985                 990

Ala Tyr Leu Ser Glu Leu Pro Val Ile Pro Gly Val Asn Ala Glu Ile
            995                 1000                1005

Phe Glu Glu Leu Glu Gly His Ile Ile Thr Ala Met Ser Leu Tyr Asp
            1010                1015                1020

Ala Arg Asn Val Val Lys Asn Gly Asp Phe Asn Asn Gly Leu Thr Cys
1025                1030                1035                1040

Trp Asn Val Lys Gly His Val Asp Val Gln Gln Ser His His Arg Ser
            1045                1050                1055

Asp Leu Val Ile Pro Glu Trp Glu Ala Glu Val Ser Gln Ala Val Arg
            1060                1065                1070

Val Cys Pro Gly Arg Gly Tyr Ile Leu Arg Val Thr Ala Tyr Lys Glu
            1075                1080                1085

Gly Tyr Gly Glu Gly Cys Val Thr Ile His Glu Ile Glu Asn Asn Thr
            1090                1095                1100

Asp Glu Leu Lys Phe Lys Asn Cys Glu Glu Glu Glu Val Tyr Pro Thr
1105                1110                1115                1120

Asp Thr Gly Thr Cys Asn Asp Tyr Thr Ala His Gln Gly Thr Ala Ala
            1125                1130                1135

Cys Asn Ser Arg Asn Ala Gly Tyr Glu Asp Ala Tyr Glu Val Asp Thr
            1140                1145                1150

Thr Ala Ser Val Asn Tyr Lys Pro Thr Tyr Glu Glu Glu Thr Tyr Thr
            1155                1160                1165

Asp Val Arg Arg Asp Asn His Cys Glu Tyr Asp Arg Gly Tyr Val Asn
            1170                1175                1180

Tyr Pro Pro Val Pro Ala Gly Tyr Val Thr Lys Glu Leu Glu Tyr Phe
1185                1190                1195                1200

Pro Glu Thr Asp Thr Val Trp Ile Glu Ile Gly Glu Thr Glu Gly Lys
            1205                1210                1215

Phe Ile Val Asp Ser Val Glu Leu Leu Leu Met Glu Glu
            1220                1225

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:5:

AAGTTTCGCA TCCATCGATG    20